US006962992B2

(12) United States Patent
Martin et al.

(10) Patent No.: US 6,962,992 B2
(45) Date of Patent: Nov. 8, 2005

(54) CROWN ETHER DERIVATIVES

(75) Inventors: Vladimir V. Martin, Eugene, OR (US); Kyle R. Gee, Springfield, OR (US); Richard P. Haugland, Eugene, OR (US); Zhenjun Diwu, Sunnyvale, CA (US)

(73) Assignee: Molecullar Probes, Inc., Eugene, OR (US)

( * ) Notice: Subject to any disclaimer, the term of this patent is extended or adjusted under 35 U.S.C. 154(b) by 142 days.

(21) Appl. No.: 10/026,302

(22) Filed: Dec. 19, 2001

(65) Prior Publication Data
US 2002/0164616 A1 Nov. 7, 2002

Related U.S. Application Data
(60) Provisional application No. 60/258,266, filed on Dec. 20, 2000.

(51) Int. Cl.[7] .................... C07D 413/04; C07D 273/00; C07D 273/08; C07D 317/28
(52) U.S. Cl. ....................... 540/451; 540/452; 540/454; 540/455; 540/469
(58) Field of Search ................................ 540/451, 452, 540/454, 455, 469

(56) References Cited

U.S. PATENT DOCUMENTS

| | | |
|---|---|---|
| 4,367,072 A | 1/1983 | Vögtle et al. |
| 4,603,209 A | 7/1986 | Tsien et al. |
| 4,774,339 A | 9/1988 | Haugland et al. |
| 4,810,636 A | 3/1989 | Corey |
| 4,812,409 A | 3/1989 | Babb et al. |
| 4,843,158 A | 6/1989 | Smith |
| 4,849,362 A | 7/1989 | DeMarinis et al. |
| 4,859,606 A | 8/1989 | Cram et al. |
| 4,945,171 A | 7/1990 | Haugland et al. |
| 4,994,395 A | 2/1991 | Chapoteau et al. |
| 5,049,673 A | 9/1991 | Tsien et al. |
| 5,096,831 A | 3/1992 | Chapoteau et al. |
| 5,132,432 A | 7/1992 | Haugland et al. |
| 5,134,232 A | 7/1992 | Tsien et al. |
| 5,136,033 A | 8/1992 | Masilamani et al. |
| 5,162,525 A | 11/1992 | Masilamani et al. |
| 5,187,288 A | 2/1993 | Kang et al. |
| 5,208,148 A | 5/1993 | Haugland et al. |
| 5,227,487 A | 7/1993 | Haugland et al. |
| 5,248,782 A | 9/1993 | Haugland et al. |
| 5,268,486 A | 12/1993 | Waggoner et al. |
| 5,274,113 A | 12/1993 | Kang et al. |
| 5,338,854 A | 8/1994 | Kang et al. |
| 5,405,975 A | 4/1995 | Kuhn et al. |
| 5,433,896 A | 7/1995 | Kang et al. |
| 5,453,517 A | 9/1995 | Kuhn et al. |
| 5,459,276 A | 10/1995 | Kuhn et al. |
| 5,501,980 A | 3/1996 | Katerinopoulos et al. |
| 5,696,157 A | 12/1997 | Wang et al. |
| 5,714,327 A | 2/1998 | Houthoff et al. |
| 5,773,227 A | 6/1998 | Kuhn et al. |
| 5,830,912 A | 11/1998 | Gee et al. |
| 5,958,782 A | 9/1999 | Bentsen et al. |
| 5,981,746 A | 11/1999 | Wolfbeis et al. |
| 6,001,999 A | 12/1999 | Wolfbeis et al. |
| 6,124,135 A | 9/2000 | Leiner et al. |
| 6,130,101 A | 10/2000 | Leung et al. |
| 6,162,931 A | 12/2000 | Gee et al. |

FOREIGN PATENT DOCUMENTS

GB    0223613 A2    5/1987

OTHER PUBLICATIONS de Saliva, et al., *Signaling Recognition Events with Fluorescent Sensors and Switches*, Chem. Rev., 1997. 97: p. 1515–1566.

Formanovskii, et al., Synthesis of macroheterocycles— analogs of dibenzocrowns, Khi. Geterotsikl. Soedin, vol. 5, 691–696 (1990), Abstract.

Poddubnykh, et al. Selective extraction and determination of silver by using nitrogen–, oxygen– and sulfur–containing macroyclic extractants, Zh. Anal. Khim, vol. 43(2), 255–260 (1988), Abstract.

Zolotov, et al., Sulfur–containing analogs of dibenzo–15–crown–5 as reagents for selective extraction of mercury, Zh. Anal. Khim., vol. 41(6), 1046–1050 (1986), Abstract.

Wang, et al., J. Wuhan Univ 2, 73–77 (1991).

(Continued)

*Primary Examiner*—Bruck Kifle
(74) *Attorney, Agent, or Firm*—Koren J. Anderson

(57) ABSTRACT

The invention describes crown ether chelators, including crown ethers having the formula

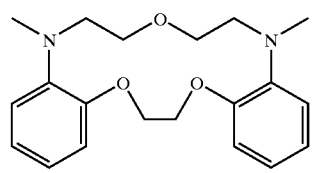

and aza-substituted and thia-substituted analogs thereof. These crown ethers are substituted by a dye moiety, a chemically reactive group, a conjugated substance, or a combination thereof.

Chelators that are substituted by fluorescent dyes are particularly useful as indicators for metal cations, particularly $Na^+$ and $K^+$ ions, and particularly where binding of the target ion results in a change in the fluorescence properties of the indicator that can be correlated with the ion concentration. Methods are provided for utilizing reactive groups on the chelators for conjugation to dyes, lipids and polymers and methods for enhancing entry of the indicators into living cells.

48 Claims, 3 Drawing Sheets

OTHER PUBLICATIONS

R. Haugland Molecular Probes Handbook of Fluorescent Probes and Research Chemicals, $8^{TH}$ Edition, on CD–ROM.

Haugland, Handbook of Fluorescent Probes and Research Chemicals, 1996 pp., 503–544.

Lockhart, et al., Ligands for the Alkali Metals. Part 3. Further Examples of Nitrogen–containing 'Crown' Compounds. J.C.S. Perkin I, 202–204 (1977).

Smith, et al., Design of an indicator of intracellular free Na+ concentration using $^{19}$F–NMR, Biochim. Biophys. ACTA 889,72–83 (1986).

Smith, et al., A New $^{19}$F–NMR Indicator for Intracellular Sodium, J.Chem.Soc. Perkin Trans. 2, 1205–1209 (1993).

de Silva, et al., Signaling Recognition Events with Fluorescent Sensors and Switches, Chem.Rev. 97, 1515–1566 (1997).

CROWN ETHER DERIVATIVES

This application claims benefit of 60/258,266 filed Dec. 20, 2000.

FIELD OF THE INVENTION

The invention relates to derivatives of crown ether chelators, including chromophoric and fluorescent derivatives, that are useful for chelating metal cations. Where the chelator is labeled with a fluorophore, it is an indicator useful for the detection, discrimination and quantification of metal cations. The chelators are optionally substituted one or more times with a chemically reactive group or a conjugated substance, such as a biological or nonbiological polymer, or a lipid.

BACKGROUND

Metal ions play an important role in biological systems. Cells utilize metal ions for a wide variety of functions, such as regulating enzyme activity, protein structure, cellular signaling, as catalysts, as templates for polymer formation and as regulatory elements for gene transcription. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. When bound to a fluorophore, ion chelators are typically used as optical indicators of ions and are useful in the analysis of cellular microenvironments or dynamic properties of proteins, membranes and nucleic acids.

Such indicators are also useful for measuring ions in extracellular spaces; in vesicles; in vascular tissue of plants and animals; biological fluids such as blood and urine; in fermentation media; in environmental samples such as water, soil, waste water and seawater; and in chemical reactors. Optical indicators for ions are important for qualitative and quantitative determination of ions, particularly in living cells. Fluorescent indicators for metal cations also permit the continuous or intermittent optical determination of these ions in living cells, and in solutions containing the ions.

A variety of fluorescent indicators that are useful for the detection of biologically relevant soluble free metal ions (such as $Ca^{2+}$, $Mg^{2+}$ and $Zn^{2+}$) have been described that utilize oxygen-containing anionic or polyanionic chelators to bind to metal ions. In particular, fluorescent indicators utilizing a polycarboxylate BAPTA chelator have been previously described (U.S. Pat. No. 4,603,209 to Tsien et al. (1986); U.S. Pat. No. 5,049,673 to Tsien et al. (1991); U.S. Pat. No. 4,849,362 to DeMarinis et al. (1989); U.S. Pat. No. 5,453,517 to Kuhn et al. (1995); U.S. Pat. No. 5,501,980 to Katerinopoulos et al. (1996); U.S. Pat. No. 5,459,276 to Kuhn et al. (1995) (all incorporated by reference). Some fluorescent indicators selective for $Li^+$, $Na^+$ and $K^+$ in aqueous or organic solution have also been described, based on the chemical modification of crown ethers (U.S. Pat. No. 5,134,232 to Tsien et al. (1992); U.S. Pat. No. 5,405,975 to Kuhn et al. (1995); both incorporated by reference.

In general, a useful property for metal ion indicators is the ability to detect and/or quantify a selected metal ion in the presence of other metal ions. Discrimination of $Ca^{2+}$, $Na^+$ and $K^+$ ions in the presence of other metal ions is particularly useful for certain biological or environmental samples. For most biological applications, it is essential that the indicators be effective in aqueous solutions. It is also useful that indicators for biological applications be relatively insensitive to pH changes over the physiological range (pH 6–8) and sensitive to ion concentrations in the physiological range (for sodium, a $K_d$ of about 5 mM to about 20 mM). It is also beneficial if the indicator absorbs and emits light in the visible spectrum where biological materials have low intrinsic absorbance or fluorescence.

Also useful are chelators that possess a chemically reactive functional group, so that the chelating group can be attached to polymers for use in remote sensing of ions or enhancing the solubility or localization of the optical sensor. Many chelators bind to intracellular proteins, altering the chelator's metal binding properties. In addition, due to their relatively small size, they are readily sequestered non-selectively in intracellular vesicles, further limiting their effectiveness. One means of circumventing these problems is to attach the desired crown ether to a large, water-soluble polysaccharide, such as dextran or FICOL, by means of modification of the polysaccharide to allow covalent attachment of the indicator. Dextrans and FICOLs are especially suitable for this application, as they are low cost, optically transparent above about 250 nm and available in multiple ranges of molecular weights. Furthermore, polysaccharides and their conjugates are reasonably compatible with most biological materials and do not interact significantly with intracellular components. Although fluorescent polysaccharides have been previously described, as have indicator conjugates of dextrans, none possess the advantageous properties of the indicator conjugates of the current invention.

The crown ether chelators of the invention show significant ability to discriminate between metal ions under physiological conditions, particularly $Ca^{2+}$, $Na^+$ and $K^+$ ions. This selectivity can be tailored by careful selection of crown ether substituents. The compounds of the invention are typically soluble in aqueous solutions.

The compounds of the invention that act as indicators for target ions absorb and emit light in the visible spectrum and possess significant utility as a means of detecting and quantifying certain metal ion levels in living cells, biological fluids or aqueous solutions. Upon binding the target ion in the chelating moiety of the indicator, the optical properties of the attached fluorophore are generally affected in a detectable way, and this change is correlated with the presence of the ion according to a defined standard. Compounds having relatively long wavelength excitation and emission bands can be used with a variety of optical devices and require no specialized (quartz) optics, such as are required by indicators that are excited or that emit at shorter wavelengths. These indicators are suitable for use in fluorescence microscopy, flow cytometry, fluoroscopy, or any other application that currently utilize fluorescent metal ion indicators.

SUMMARY OF THE INVENTION AND DESCRIPTION OF THE PREFERRED EMBODIMENTS

Figure 1:
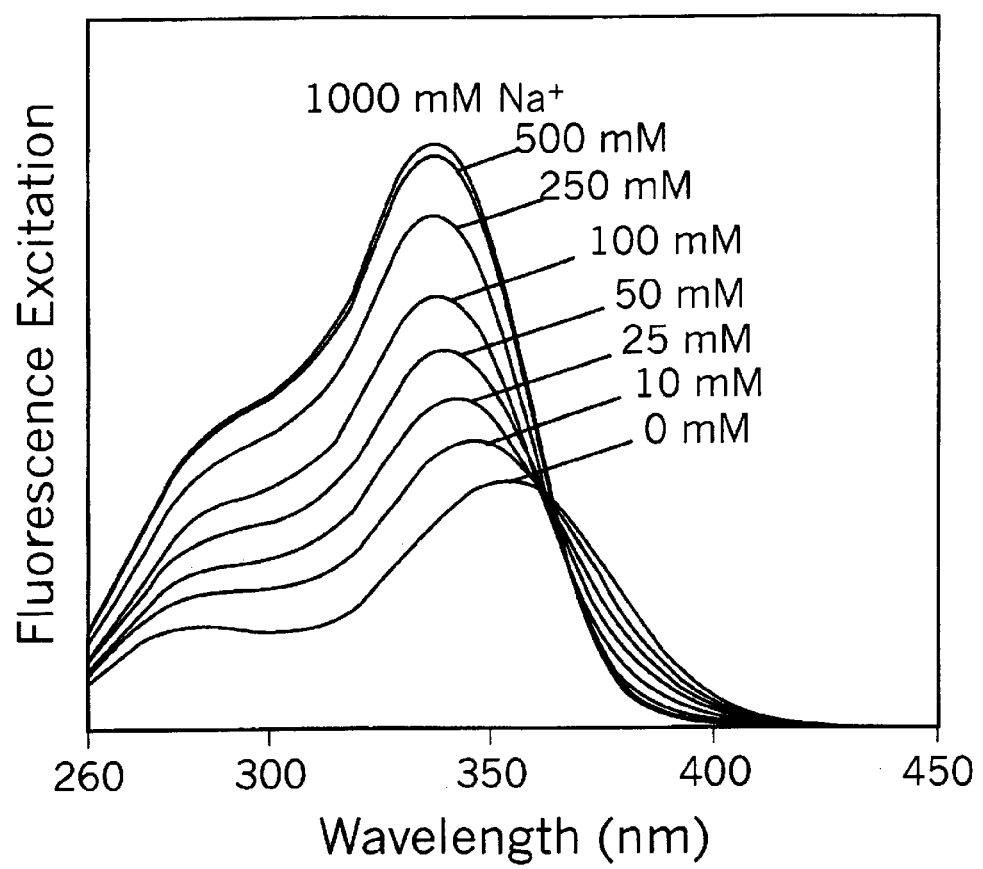
FIG. 1. The $Na^+$-dependent fluorescence excitation spectra of Compound 167 in a series of solutions containing 0 to 1000 mM free $Na^+$, with fluorescence emission monitored at 510 nm (as described in Example 71).
Figure 2:
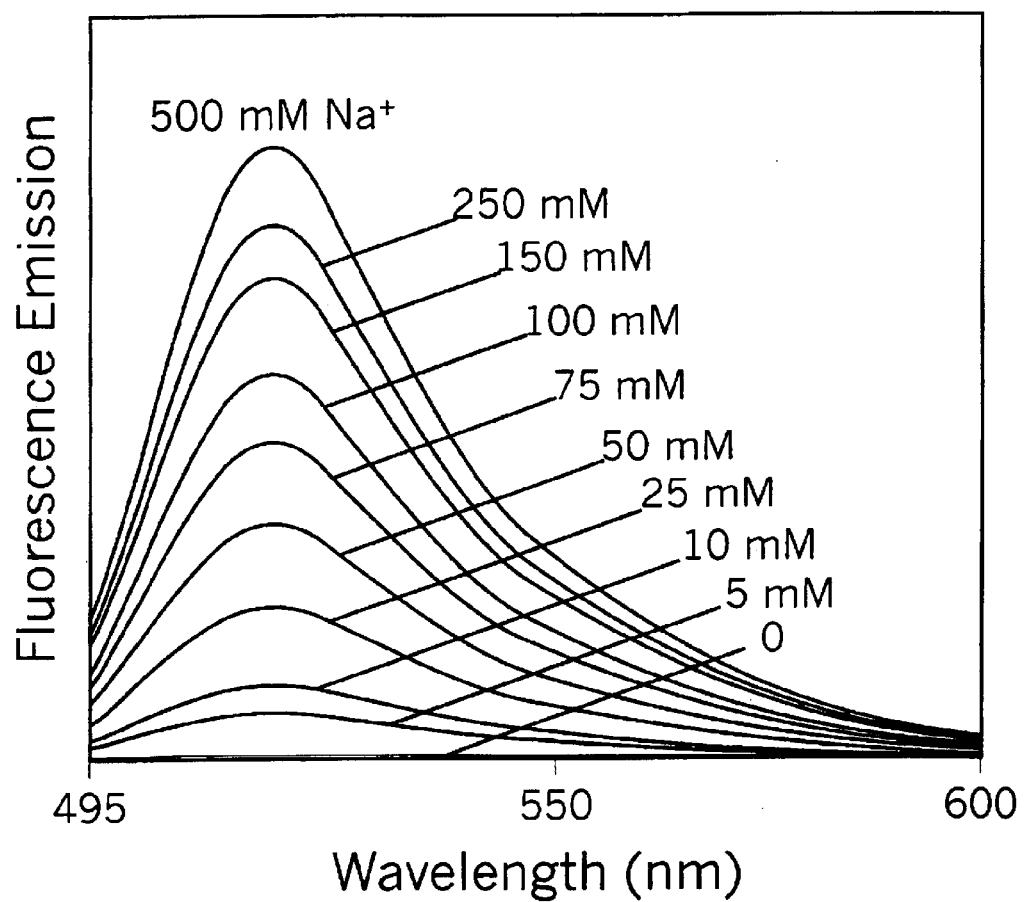
FIG. 2. The $Na^+$-dependent fluorescence emission spectra of Compound 132 in a series of solutions containing 0 to 500 mM free $Na^+$, with excitation at 488 nm (as described in Example 71).

The compounds of the invention have the formula

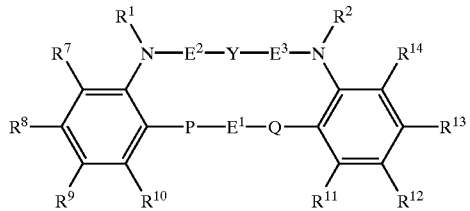

The heteroatoms P and Q are independently selected from O, S, or $NR^3$, where each $R^3$ is independently H or an alkyl having 1–6 carbons. In one aspect of the invention P and Q are both O.

The heteroatom Y is O, S, or $NR^4$, where $R^4$ is H, a $C_1$–$C_{18}$ alkyl, or an aryl or heteroaryl ring system. The $R^4$ alkyl or ring system substituent is optionally substituted one or more times by halogen, azido, nitro, nitroso, amino, alkylamino having 1–6 carbons, dialkylamino having 2–12 carbons, cyano, or $R^4$ is substituted one or more times by a $C_1$–$C_6$ alkyl or $C_1$–$C_6$ alkoxy that is itself optionally substituted one or more times by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. Alternatively, $R^4$ is, or ifs substituted by -L-$R_X$, -L-$S_C$, or -L-DYE.

Each $R^{15}$ is independently H or $C_1$–$C_6$ alkyl. Each $R^{16}$ is H, a $C_1$–$C_6$ alkyl, a benzyl, or forms an ester (e.g., $R^{16}$ is an alpha-acyloxyalkyl, a t-butyldimethylsilyl, or any other biologically compatible esterifying group). Additionally, any $R^{16}$ is a biologically compatible salt. $R^{17}$ and $R^{18}$ are independently H or $C_1$–$C_6$ alkyl or $C_1$–$C_6$ carboxyalkyl, or an alpha-acyloxyalkyl, a t-butyldimethylsilyl, or any other biologically compatible esterifying group, or a biologically compatible salt; or $R^{17}$ and $R^{18}$ when taken in combination form a 5- or 6-membered aliphatic ring that optionally incorporates an oxygen atom. In addition, one or more of a $R^{15}$, $R^{16}$, $R^{17}$, or $R^{18}$ is permitted to be -L-$R_X$, -L-$S_C$, or -L-DYE.

Each L is independently a covalent linkage. Each $R_X$ is independently a reactive functional group. Each $S_C$ is independently a conjugated substance. Each DYE is independently a moiety that maximally absorbs light at a wavelength greater than 320 nm.

In one aspect of the invention, P and Q are O, and Y is $NR^4$. In another aspect of the invention, P, Q, and Y are each O. Careful selection of the nature of the P, Q, and Y heteroatoms permits the moderation of the selectivity and binding affinity of the resulting crown ether.

$E^1$, $E^2$, and $E^3$ each independently have the formula —($CR^5_2$)$_n$—, or —[C(O)$CH_2$]$_n$—, where n=2–4. Each $R^5$ is independently H or methyl, or the $R^5$ moieties on adjacent carbon atoms of each chain, when taken in combination, form a 5- or 6-membered aliphatic ring. For a given E moiety, each $R^5$ s is typically H and n is 2. Where n is 2 for each E moiety, the resulting compound is known as a 15-crown-5 crown ether, having 15 atoms in the chelating ring itself, of which 5 are heteroatoms.

The amine substituents $R^1$ and $R^2$ are independently H, $C_1$–$C_{18}$ alkyl, or $C_7$–$C_{18}$ arylalkyl. Where $R^1$ or $R^2$ is alkyl or arylalkyl, it is optionally substituted one or more times by halogen, azido, nitro, nitroso, amino, hydroxy, $C_1$–$C_6$ alkylamino, $C_2$–$C_{12}$ dialkylamino, cyano, or by an aryl or heteroaryl ring system, or by —($SO_2$)—$R^{15}$, —($SO_2$)—O—$R^{15}$, —(C=O)—$R^{15}$, —(C=O)—O—$R^{16}$, or —(C=O)—$NR^{17}R^{18}$, where $R^{15}$, $R^{16}$, $R^{17}$, and $R^{18}$ are as defined above; or by a $C_1$–$C_6$ alkyl or $C_1$–$C_6$ alkoxy that is itself optionally substituted one or more times by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. Alternatively, $R^1$ and $R^2$ are optionally -L-$R_X$, -L-$S_C$, or -L-DYE.

For purposes of this invention, an aryl or aromatic ring system means a substituent containing 1 to 4 unsaturated rings (each ring containing 6 conjugated carbon atoms and no heteroatoms) that are optionally fused to each other or bonded to each other by carbon-carbon single bonds, and is optionally substituted as described below. Specific examples of an aryl ring system include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Preferably an aryl substituent is phenyl, substituted phenyl, naphthyl or substituted naphthyl.

For purposes of this invention, a heteroaryl or heteroaromatic ring system means a 5- or 6-membered unsaturated ring that is optionally fused to an additional six-membered aromatic ring(s), or is fused to one 5- or 6-membered unsaturated ring containing one or more heteroatoms, and is optionally substituted as defined below. Each heteroaromatic ring contains at least 1 and as many as 3 heteroatoms that are selected from the group consisting of O, N or S in any combination. Specific examples of a heteroaryl ring system include, but are not limited to, substituted or unsubstituted derivatives of 2- or 3-furanyl; 2- or 3-thienyl; N-, 2- or 3-pyrrolyl; 2- or 3-benzofuranyl; 2- or 3-benzothienyl; N-, 2- or 3-indolyl; 2-, 3- or 4-pyridyl; 2-, 3- or 4-quinolyl; 1-, 3-, or 4-isoquinolyl; 2-, 4-, or 5-(1,3-oxazolyl); 2-benzoxazolyl; 2-, 4-, or 5-(1,3-thiazolyl); 2-benzothiazolyl; 3-, 4-, or 5-isoxazolyl; N—, 2-, or 4-imidazolyl; N-, or 2-benzimidazolyl; 1- or 2-naphthofuranyl; 1- or 2-naphthothienyl; N-, 2- or 3-benzindolyl; 2-, 3-, or 4-benzoquinolyl; 1-, 2-, 3-, or 4-acridinyl. Preferably the heteroaryl substituent is substituted or unsubstituted 4-pyridyl, 2-thienyl, 2-pyrrolyl, 2-indolyl, 2-oxazolyl, 2-benzothiazolyl or 2-benzoxazolyl. More preferably, the heteroaryl substituent is 2-thienyl or 2-pyrrolyl.

Any aryl or heteroaryl ring system is unsubstituted or optionally and independently substituted by any synthetically accessible and chemically stable combination of substituents that are independently H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, typically the alkyl portions of which contain 18 or fewer carbons.

Where the $R^1$ and $R^2$ substituents are not -L-$R_X$, -L-$S_C$, or -L-DYE, they are typically both alkyl that is substituted one or more times by carboxylic acids, by carboxylic acid esters, by carboxylic acid amides, or by cyano. Where $R^1$ and $R^2$ incorporate carboxylic acid esters, they are optionally selected to be esters that are readily cleaved by intracellular esterase enzymes, such as alpha-acyloxyalkyl esters (typically acetoxymethyl esters). Alternatively, $R^1$ and $R^2$ incorporate carboxylic acid esters that are typically not cleaved, such as esters of lower alcohols (for example methyl or ethyl esters). In one embodiment, at least one of $R^1$, $R^2$, and $R^7$–$R^{14}$ incorporates multiple carboxylic acids or carboxylic acid esters. Selection of the precise nature of $R^1$ and $R^2$ can greatly affect the selectivity and binding selectivity and affinity of the resulting compound (see Table 1).

The benzo substituents $R^7$–$R^{14}$ are independently H, halogen, azido, nitro, nitroso, amino, cyano; or -L-$R_X$, -L-$S_C$, or -L-DYE; or $C_1$–$C_6$ alkyl or $C_1$–$C_6$ alkoxy that is itself optionally substituted one or more times by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$.

Alternatively, two adjacent substituents of $R^7$–$R^{14}$, when taken in combination, form a fused six-membered benzo moiety, which is optionally substituted one or more times by a halogen, azido, nitro, nitroso, amino, cyano, -L-$R_X$, -L-$S_C$, or -L-DYE; or by a $C_1$–$C_6$ alkyl or $C_1$–$C_6$ alkoxy, which is itself optionally substituted one or more times by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$.

In one aspect of the invention, two adjacent substituents of $R^7$–$R^{14}$, when taken in combination with each other, and with the aromatic ring they are bound to, form a fused DYE.

The compounds of the invention are substituted by at least one -L-DYE, -L-$R_X$ or -L-$S_C$ at one or more of $R^1$, $R^2$, $R^4$, and $R^7$–$R^{14}$; or two of $R^7$–$R^{14}$, taken in combination, form a fused DYE. In one embodiment, the compound of the invention is substituted by exactly one -L-DYE moiety, which is bound at $R^1$, $R^2$, an $R^4$, or one of $R^7$–$R^{14}$, or is a fused DYE moiety at two adjacent substituents of $R^7$–$R^{14}$. The DYE moiety is typically bound at one of $R^7$–$R^{11}$, preferably at $R^9$, or is bound at $R^4$ where Y is $NR^4$. In one embodiment, compounds that are substituted by exactly one -L-DYE moiety are optionally further substituted by -L-$R_X$ or -L- —$S_C$, typically at $R^1$, $R^2$, $R^4$, or one of $R^7$–$R^{14}$.

In another embodiment, the compound of the invention is substituted by exactly two DYE moieties, which may be the same or different, and may be bound by a covalent linkage L or fused to the crown ether chelate. In one embodiment of the invention, a first -L-DYE moiety is bound at one of $R^7$–$R^{10}$, while the second -L-DYE moiety is bound at one of $R^{11}$–$R^{14}$. Typically, the first -L-DYE moiety is bound at $R^9$, while the second -L-DYE moiety is bound at $R^{12}$, or a DYE moiety is fused at $R^8$ and $R^9$ and additionally at $R^{12}$ and $R^{13}$.

In one aspect of the invention, the compound of the invention has the formula

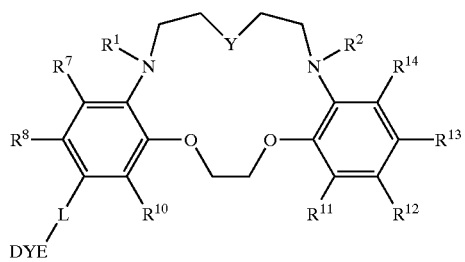

where Y is either O or $NR^4$; and the DYE moiety is an indole, a coumarin, a stilbene, a xanthene, or a polyazaindacene. In this embodiment, preferably the DYE moiety is a xanthene, a polyazaindacene, or an oxazine.

In one aspect of the invention, the compounds of the invention are fluorescent indicators having the following structure:

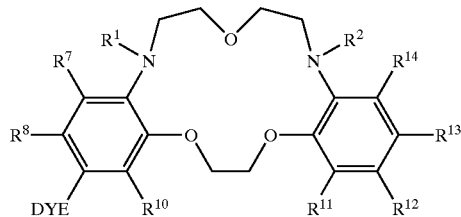

These indicators typically exhibit a low fluorescence quantum efficiency in the absence of metal ions. However, in the presence of increasing metal ion concentration the fluorescence quantum efficiency rises dramatically. For example, selected indicators of this family exhibit a fluorescence signal increase of over 100-times between zero and a saturating sodium concentration. Other selected indicators of the invention exhibit a shift of the wavelength of the absorption (excitation) maximum, emission maximum, or both, upon binding the target ion.

In one embodiment of this aspect, $R^1$ and $R^2$ are $C_1$–$C_6$ alkyl that are substituted one or more times by cyano, an aryl or heteroaryl ring system, or by —(C=O)—O—$R^{16}$ or —(C=O)—$NR^{17}R^{18}$, where $R^{16}$ is H, a $C_1$–$C_6$ alkyl, a benzyl, a biologically compatible esterifying group, or a biologically compatible salt; and $R^{17}$ and $R^{18}$ are independently H, $C_1$–$C_6$ alkyl, $C_1$–$C_6$ carboxyalkyl, an alpha-acyloxymethyl, or a biologically compatible salt. The substituents $R^7$ $R^8$, $R^{10}$, and $R^{11}$–$R^{14}$, are independently H, chloro, bromo, fluoro, nitro, amino, or cyano; or $C_1$–$C_6$ alkyl or $C_1$–$C_6$ alkoxy that is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. The DYE moiety is a polyazaindacene, an oxazine, or a xanthene, which is optionally substituted one or more times by halogen, nitro, sulfo, cyano, an aryl or heteroaryl ring system, or benzo, or alkyl, perfluoroalkyl, alkoxy, alkenyl, alkynyl, cycloalkyl, arylalkyl, acyl, or carboxylic acids or carboxylic acid esters, the alkyl portions of which contain fewer than 20 carbons.

In another aspect of the invention, the compounds of the invention are fluorescent indicators having the following structure:

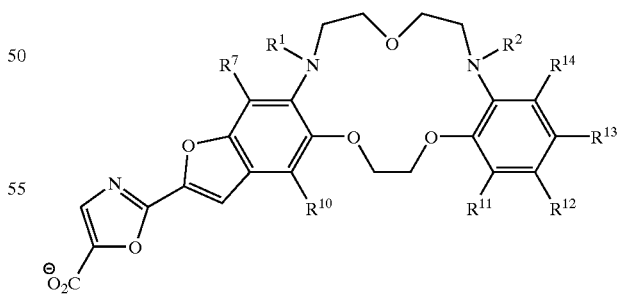

This class of indicators, in which at least one of the aromatic rings of the crown ether portion of the indicator is also incorporated in the DYE moiety, typically exhibit ratiometric fluorescence excitation changes in response to changing metal ion concentration. That is, there is a shift in the excitation maximum wavelength in the presence of increasing metal ion concentrations.

In one embodiment of this aspect, $R^1$ and $R^2$ are $C_1$–$C_6$ alkyl that are substituted one or more times by cyano, an aryl or heteroaryl ring system, or by —(C=O)—O—$R^{16}$ or —(C=O)—$NR^{17}R^{18}$, where $R^{16}$ is H, a $C_1$–$C_6$ alkyl, a benzyl, a biologically compatible esterifying group, or a biologically compatible salt; and $R^{17}$ and $R^{18}$ are independently H, $C_1$–$C_6$ alkyl, $C_1$–$C_6$ carboxyalkyl, an alpha-acyloxymethyl, or a biologically compatible salt. The substituents $R^7$, $R^{10}$, and $R^{11}$–$R^{14}$, are independently H, chloro, bromo, fluoro, nitro, amino, or cyano; or $C_1$–$C_6$ alkyl or $C_1$–$C_6$ alkoxy that is itself optionally substituted by halogen, amino, hydroxy, —(SO$_2$)—$R^{15}$, —(SO$_2$)—O—$R^{15}$, —(C=O)—$R^{15}$, —(C=O)—O—$R^{16}$, or —(C=O)—$NR^{17}R^{18}$.

The nature of the $R^1$ and $R^2$ substituents in large part determines the response of the indicators to particular target ions. For example, where the crown ether derivatives have the formula

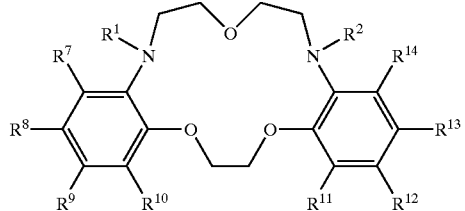

where $R^1$ and $R^2$ are each methoxycarbonylmethyl selectively typically bind sodium ions with a dissociation constant ($K_d$) of approximately 20–100 mM, and are relatively insensitive to the presence of potassium ions. In particular, the sodium ion $K_d$ values typically rise less than about 10% when measured in the presence of 100 mM potassium ion.

An additional selected embodiment of the invention has the formula

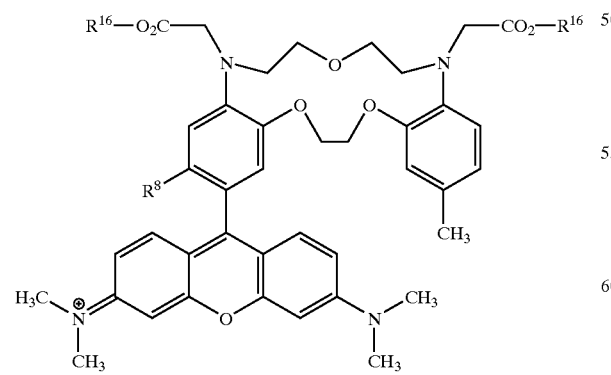

where $R^8$ and $R^{16}$ are defined as above.

An additional selected embodiment of the invention has the formula

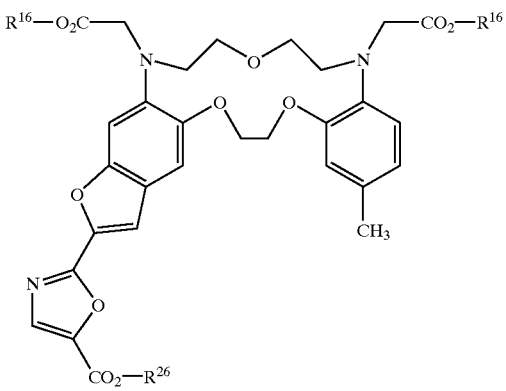

or the formula

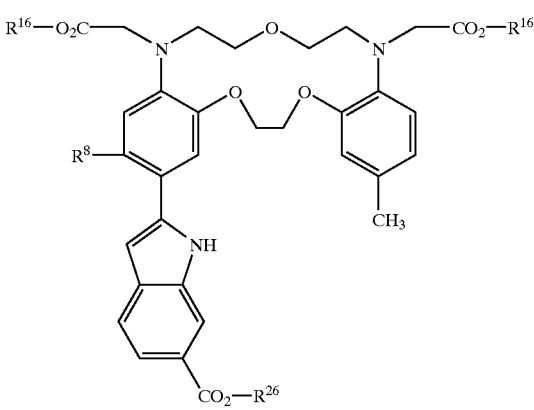

where $R^8$ and $R^{16}$ are defined as above, and $R^{26}$ is H, a $C_1$–$C_6$ alkyl, a benzyl, or is an alpha-acyloxyalkyl or a t-butyldimethylsilyl or other biologically compatible esterifying group, or is a biologically compatible salt.

An additional selected embodiment of the invention has the formula

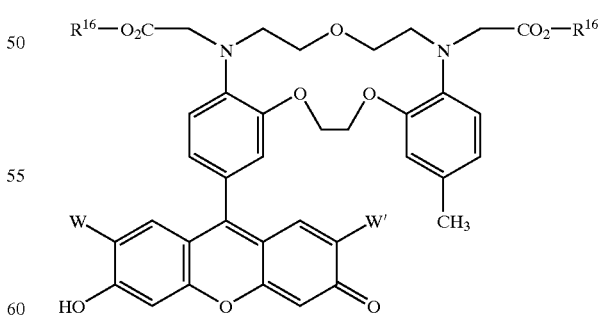

where $R^{16}$ is defined as above, and W and W' are independently F or Cl.

An additional selected embodiment of the invention has the formula

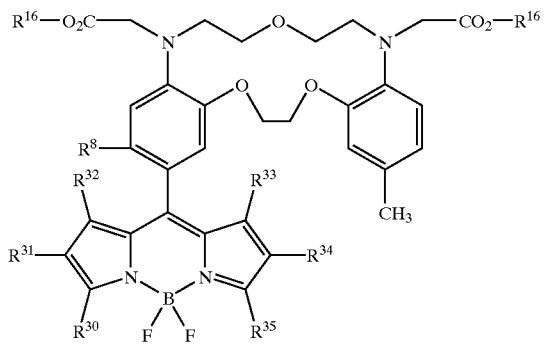

where $R^8$ and $R^{16}$ are defined as above, and $R^{30}$–$R^{35}$ are independently hydrogen, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons; or aryl or heteroaryl ring system; or adjacent substituents $R^{31}$ and $R^{32}$, and adjacent substituents $R^{33}$ and $R^{34}$, when taken in combination form a fused benzo ring that is optionally substituted one or more times by hydrogen, halogen, nitro, sulfo, cyano, alkyl, perfluoroalkyl, alkoxy, alkenyl, alkynyl, cycloalkyl, alkylthio, alkylamido, amino, monoalkylamino or dialkylamino wherein the alkyl portions of each contain fewer than 20 carbons.

In an additional aspect of the invention, the compound of the invention further comprises a metal ion that is associated and/or complexes within the crown ether chelate portion of the compound. The metal ion is optionally a monocation (such as $Li^+$, $Na^+$, $K^+$, $Rb^+$, or $Cs^+$), a dication (such as $Ca^{2+}$, $Zn^{2+}$, or $Mg^{2+}$), or a polycation (such as $Tb^{3+}$ or $Eu^{3+}$).

The DYE Moiety

The DYE moiety is any chemical moiety that exhibits an absorption maximum beyond 320 nm, that is bound to the crown ether chelate by a covalent linkage L, or that is fused to the crown ether chelate. The covalent linkage L is either a single covalent bond, or a combination of stable chemical bonds, as described in greater detail below. The covalent linkage binding the DYE moiety to the crown ether chelator is typically a single bond, but optionally incorporates 1–20 nonhydrogen atoms selected from the group consisting of C, N, O, P, and S. In one embodiment, L is or incorporates a phenylene or a 2-carboxy-substituted phenylene.

Typically the DYE moiety contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

In one aspect of the invention, the DYE moiety has an absorption maximum beyond 480 nm. In a particularly useful embodiment, the DYE moiety absorbs at or near 488 nm to 514 nm (particularly suitable for excitation by the output of the argon-ion laser excitation source) or near 546 nm (particularly suitable for excitation by a mercury arc lamp). The DYE moiety may be a chromophore, resulting in a compound that acts as a chromogenic indicator, or more preferably, DYE is additionally a fluorophore, resulting in a compound that is a fluorescent indicator. Preferably, binding a target ion within the crown ether chelate results in a detectable optical response. As used herein, a detectable optical response means a change in, or occurrence of, an optical signal that is detectable either by observation or instrumentally, such a change in absorption (excitation) wavelength, fluorescence emission wavelength, or fluorescence emission intensity.

Where the detectable response is a fluorescence response, it is typically a change in fluorescence, such as a change in the intensity, excitation or emission wavelength distribution of fluorescence, fluorescence lifetime, fluorescence polarization, or a combination thereof. Preferably, the detectable optical response upon binding the target metal ion is a change in fluorescence intensity that is greater than approximately 10-fold, more preferably greater than 50-fold. In another aspect, the detectable optical response upon binding the target metal ion is a shift in maximal excitation or emission wavelength that is greater than about 20 nm, more preferably greater than about 30 nm. Sodium and potassium indicators of the type that exhibit significant emission shifts have not been previously described.

A wide variety of chemically reactive fluorescent dyes that may be suitable for incorporation into the compounds of the invention are already known in the art (see for example MOLECULAR PROBES HANDBOOK OF FLUORESCENT PROBES AND RESEARCH CHEMICALS, Sixth Ed., Richard P. Haugland, ed. (1996), and Seventh Ed., Richard P. Haugland, ed. (1999) on CD-ROM; BIO-PROBES 32 (December 1999); BIOPROBES 33 (February 2000); BIOPROBES 34 (May 2000); and BIOPROBES 35 (November 2000)). The spectral properties of candidate dyes in solution or when conjugated to proteins such as IgG are known or are readily measured using an absorption spectrometer or a spectrofluorometer.

In one aspect of the invention, the DYE moiety is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated derivatives thereof (as described in U.S. Pat. No. 5,830,912 (1998), incorporated by reference), a polyazaindacene (e.g., U.S. Pat. No. 4,774,339 to Haugland, et al. (1988); U.S. Pat. No. 5,187,288 to Kang, et al. (1993); U.S. Pat. No. 5,248, 782 to Haugland, et al. (1993); U.S. Pat. No. 5,274,113 to Kang, et al. (1993); and U.S. Pat. No. 5,433,896 to Kang, et al. (1995), all incorporated by reference), a xanthene, an oxazine or a benzoxazine, a carbazine (U.S. Pat. No. 4,810, 636 to Corey (1989), incorporated by reference), or a phenalenone or benzphenalenone (U.S. Pat. No. 4,812,409 Babb et al. (1989), incorporated by reference). In another aspect of the invention, the DYE moiety is a carbazine, an oxazine, a coumarin, a pyrene, a xanthene, a naphthalene, a phenalenone, or a polyazaindacene. As used herein, oxazines include resorufins, aminooxazinones, diaminooxazines, and their benzo-substituted analogs.

Where the DYE moiety is a xanthene, the synthetic dye is optionally a fluorescein, a rhodol (U.S. Pat. No. 5,227,487 to Haugland, et al. (1993), incorporated by reference), or a rhodamine. As used herein, fluorescein includes benzo- or dibenzofluoresceins, seminaphthofluoresceins, or naphthofluoresceins. Similarly, as used herein rhodol includes semi-naphthorhodafluors (U.S. Pat. No. 4,945,171 to Haugland, et al. (1990), incorporated by reference). Fluorinated xanthene dyes have been described previously as possessing particularly useful fluorescence properties (Int. Publ. No. WO 97/39064, Molecular Probes, Inc. (1997), U.S. Pat. No. 6,162,931 to Gee et al. (2000), incorporated by reference).

Alternatively, the DYE moiety is a xanthene that is bound via an L that is a single covalent bond at the 9-position of the xanthene. Preferred xanthenes include derivatives of 3H-xanthen-6-ol-3-one bound at the 9-position, derivatives of 6-amino-3H-xanthen-3-one bound at the 9-position, or derivatives of 6-amino-3H-xanthen-3-imine bound at the 9-position.

Selected sulfonated DYE moieties also exhibit advantageous properties, and include sulfonated pyrenes, coumarins, carbocyanines, and xanthenes (as described in U.S. Pat. No. 5,132,432 to Haugland et al., (1992); U.S. Pat. No. 5,696,157 to Wang et al. (1997); U.S. Pat. No. 5,268,486 patent to Waggoner et al. (1993); U.S. Pat. No. 6,130,101 to Mao et al. (2000); all incorporated by reference). Sulfonated pyrenes and coumarins are typically excited at wavelengths below about 450 nm.

As described above, in one aspect of the invention, two adjacent substituents of $R^7$–$R^{14}$, when taken in combination with each other, and with the aromatic ring they are bound to, form a fused DYE. In one aspect of the invention, the fused DYE is a carbocyanine dye (as in Wang et al., J. WUHAN UNIV 2, 73 (1991)). In another embodiment, two adjacent ring substituents taken in combination form DYE moiety that is a fused benzofuran or heteroaryl- or carboxyheteroaryl-substituted benzofuran fluorophore, or a fused 6-membered unsaturated lactone, or benzazole-substituted lactone. Where the DYE moiety is fused to the compound of the invention, it is preferably fused $R^8$ and $R^9$, or at $R^{12}$ and $R^{13}$.

Selected embodiments of the invention are given in Table 1, showing a variety of distinct DYE moieties and crown ether substituents useful in the invention.

TABLE 1

Selected embodiments of the invention.

| Compound | | Dissociation Constant (target ion) |
|---|---|---|
| 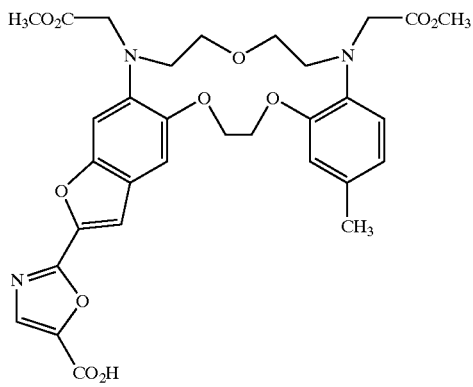 | Compound 167 | $K_d(Na^+)$ = ~52 mM<br>$K_d(K^+)$ = ~330 mM |
| 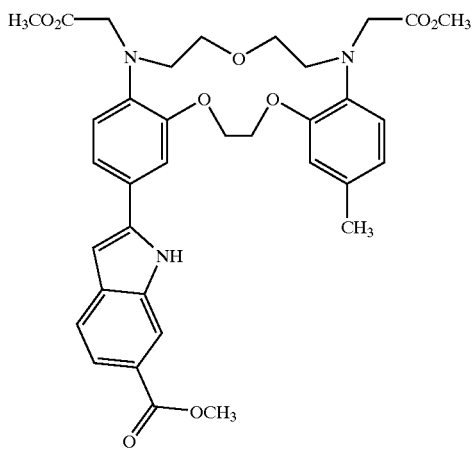 | Compound 148 | $K_d(Na^+)$ = ~30 mM<br>$K_d(K^+)$ = ~115 mM |

TABLE 1-continued

Selected embodiments of the invention.

| Compound | | Dissociation Constant (target ion) |
|---|---|---|
| [structure] | Compound 180 | $K_d(Na^+) = \sim 220$ mM |
| [structure] | Compound 174 | $K_d(Na^+) = \sim 52$ mM<br>$K_d(K^+) = \sim 250$ mM |
| [structure] | Compound 132 | $K_d(Na^+) = \sim 60$ mM<br>$K_d(K^+) = \sim 205$ mM |
| [structure] | Compound 145 | $K_d(Na^+) = \sim 42$ mM |

TABLE 1-continued

Selected embodiments of the invention.

| Compound | | Dissociation Constant (target ion) |
|---|---|---|
| [structure of Compound 164: BODIPY-based crown ether with dimethyl-substituted aryl group, H3CO2C-N and CO2CH3 groups, HO2C-O linker] | Compound 164 | $K_d(Na^+)$ = ~28 mM<br>$K_d(K^+)$ = ~130 mM |
| [structure of Compound with rhodamine-based xanthene core, methoxy-substituted aryl, H3CO2C-N-CO2CH3 diaza-crown] | | |
| [structure of Compound 138: rhodamine-based xanthene with methyl-substituted aryl group, H3CO2C-N-CO2CH3 diaza-crown] | Compound 138 | $K_d(Na^+)$ = ~95 mM<br>$K_d(K^+)$ = ~300 mM |
| [structure of Compound 152: rhodamine-based xanthene with methyl-substituted aryl, H3CO2C-N-CO2CH3 diaza-crown, with ⊖O2C-O carboxylate group] | Compound 152 | $K_d(Na^+)$ = ~92 mM<br>$K_d(K^+)$ = ~705 mM |

TABLE 1-continued

Selected embodiments of the invention.

| Compound | | Dissociation Constant (target ion) |
|---|---|---|
| [chemical structure] | Compound 177 | $K_d(Na^+) = \sim70$ mM<br>$K_d(Zn^{2+}) = \sim100$ nM |
| [chemical structure] | | $K_d(Na^+) = \sim85$ mM<br>$K_d(K^+) = \sim255$ nM |
| [chemical structure] | Compound 156 | $K_d(Na^+) = \sim14$ mM |
| [chemical structure] | Compound 143 | $K_d(Na^+) = \sim103$ mM<br>$K_d(K^+) = \sim205$ mM |

TABLE 1-continued

Selected embodiments of the invention.

| Compound | | Dissociation Constant (target ion) |
|---|---|---|
| [structure] | Compound 139 | $K_d(Zn^{2+}) = \sim 300$ nM<br>$K_d(Ca^{2+}) = \sim 4$ μM<br>$K_d(Na^+) = \sim 38$ mM<br>$K_d(K^+) = \sim 270$ mM |
| [structure] | Compound 144 | $K_d(Zn^{2+}) = \sim 8$ μM<br>$K_d(Ca^{2+}) = \sim 7$ μM |
| [structure] | Compound 133 | $K_d(Na^+) = \sim 36$ mM<br>$K_d(K^+) = \sim 215$ mM<br>$K_d(Zn^{2+}) = \sim 300$ nM<br>$K_d(Ca^{2+}) = \sim 5$ μM |

TABLE 1-continued

Selected embodiments of the invention.

| Compound | Dissociation Constant (target ion) |
|---|---|
| | $K_d(Na^+)$ = ~2.0M<br>$K_d(Zn^{2+})$ = ~600 μM |
| Compound 182 | $K_d(Na^+)$ = ~500 mM<br>$K_d(Zn^{2+})$ = ~650 μM |
| Compound 171 | $K_d(Ca^{2+})$ = ~400 nM<br>$K_d(Na^+)$ = ~160 mM |

TABLE 1-continued

Selected embodiments of the invention.

| Compound | Dissociation Constant (target ion) |
|---|---|

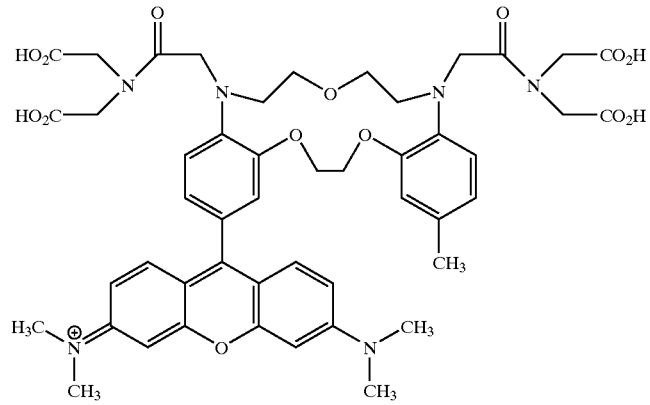

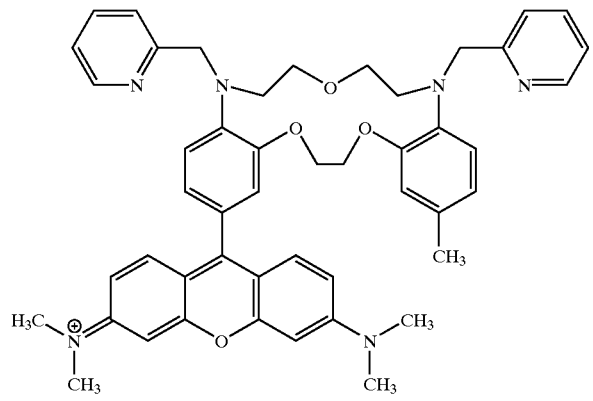

Reactive Functional Groups and Conjugated Substances

In one embodiment, the compound of the invention is substituted one or more times by an -L-$R_X$ moiety, where $R_X$ is the reactive group that is bound by an additional covalent linkage L, that may be the same or different from the covalent linkage that binds the DYE moiety to the crown ether chelator. In certain embodiments, the covalent linkage contains multiple intervening atoms that serve as a spacer. Compounds incorporating a reactive group ($R_X$) can be coupled to a wide variety of organic or inorganic substances that contain or are modified to contain functional groups with suitable reactivity, resulting in chemical attachment of the conjugated substance ($S_C$), represented by -L-$S_C$. The reactive group and functional group are typically an electrophile and a nucleophile that can generate a covalent linkage. Alternatively, the reactive group is a photoactivatable group, and becomes chemically reactive only after illumination with light of an appropriate wavelength. Typically, the conjugation reaction between the reactive group and the substance to be conjugated results in one or more atoms of the reactive group $R_X$ to be incorporated into a new linkage L attaching the compound of the invention to the conjugated substance $S_C$. Selected examples of functional groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |

TABLE 2-continued

Examples of some routes to useful covalent linkages

| Electrophilic Group | Nucleophilic Group | Resulting Covalent Linkage |
| --- | --- | --- |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —CO$\Omega$, where $\Omega$ is a good leaving group (e.g., succinimidyloxy (—OC$_4$H$_4$O$_2$) sulfosuccinimidyloxy (—OC$_4$H$_3$O$_2$—SO$_3$H),-1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to formactivated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$–C$_6$ alkyl, C$_1$–C$_6$ perfluoroalkyl, or C$_1$–C$_6$ alkoxy; or cyclohexyl, 3-dimethylaminopropyl, or N-morpholinoethyl).
**Acyl azides can also rearrange to isocyanates The covalent linkage L binds the reactive group R$_X$ or conjugated substance S$_C$ to the compound of the invention, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds, carbon-sulfur bonds, carbon-phosphorus bonds, phosphorus-oxygen bonds, phosphorus-nitrogen bonds, nitrogen-platinum bonds, and carbon-silicon bonds. L typically includes ether, thioether, carboxamide, sulfonamide, urea, urethane or hydrazine moieties. In one embodiment, the covalent linkage incorporates a platinum atom, such as described in U.S. Pat. No. 5,714,327 (incorporated by reference).

Preferred L moieties have 1–20 nonhydrogen atoms selected from the group consisting of C, N, O, P, and S; and are composed of any combination of ether, thioether, amine, ester, carboxamide, sulfonamide, hydrazide bonds and aromatic or heteroaromatic bonds. Preferably L is a combination of single carbon-carbon bonds and carboxamide or thioether bonds. The longest linear segment of the linkage L preferably contains 4–10 nonhydrogen atoms, including one or two heteroatoms. Examples of L include substituted or unsubstituted polymethylene, arylene, alkylarylene, arylenealkyl, or arylthio.

In one embodiment, L contains 1–6 carbon atoms; in another, L comprises a thioether linkage. In another embodiment, L is or incorporates the formula —(CH$_2$)$_d$(CONH(CH$_2$)$_e$)$_z$— or —O(CH2)$_d$(CONH(CH$_2$)$_e$)$_z$—, where d is an integer from 0–5, e is an integer from 1–5 and z is 0 or 1. In a further embodiment, L is or incorporates the formula —O—(CH$_2$)—. In yet another embodiment, L is or incorporates a phenylene or a 2-carboxy-substituted phenylene.

Choice of the reactive group used to attach the compound of the invention to the substance to be conjugated typically depends on the functional group on the substance to be conjugated and the type or length of covalent linkage desired. The types of functional groups typically present on the organic or inorganic substances include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins. A conjugated substance may be conjugated to more than one dye, which may be the same or different, or to a substance that is additionally modified by a hapten, such as biotin. Although some selectivity can be obtained by careful control of the reaction conditions, selectivity of labeling is best obtained by selection of an appropriate reactive functional group.

Typically, R$_X$ will react with an amine, an alcohol, an aldehyde, a ketone, or with silica. Preferably R$_X$ reacts with an amine or a thiol functional group, or with silica. In one embodiment, R$_X$ is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327 (incorporated by reference).

Where R$_X$ is an activated ester of a carboxylic acid, the resulting compound is particularly useful for preparing conjugates of proteins, nucleotides, oligonucleotides, or haptens. Where R$_X$ is a maleimide or haloacetamide the resulting compound is particularly useful for conjugation to thiol-containing substances. Where R$_X$ is a hydrazide, the resulting compound is particularly useful for conjugation to periodate-oxidized carbohydrates and glycoproteins, and in addition is an aldehyde-fixable polar tracer for cell microinjection. Where R$_X$ is a silyl halide, the resulting compound is particularly useful for conjugation to silica surfaces, particularly where the silica surface is incorporated into a fiber optic probe subsequently used for remote ion detection or quantitation.

Preferably, R$_X$ is a succinimidyl ester of a carboxylic acid, a haloacetamide, a hydrazine, an isothiocyanate, a maleimide group, an aliphatic amine, a silyl halide, or a psoralen. More preferably, R$_X$ is a succinimidyl ester of a carboxylic acid, a maleimide, an iodoacetamide, or a silyl halide. In a particular embodiment R$_X$ is a silyl halide or an isothiocyanate.

The compounds of the invention that possess a reactive functional group are useful for conjugation to any substance that possesses a suitable functional group for covalent attachment of the chelate. Examples of particularly useful conjugates include, among others, conjugates of antigens, steroids, vitamins, drugs, haptens, metabolites, toxins, environmental pollutants, amino acids, peptides, proteins, nucleic acids, nucleic acid polymers, carbohydrates, lipids, and non-biological polymers. Alternatively, these are conjugates of cells, cellular systems, cellular fragments, or subcellular particles. Examples include, among others, virus particles, bacterial particles, virus components, biological cells (such as animal cells, plant cells, bacteria, yeast, or protists), or cellular components.

Preferably the conjugated substance is a protein, polysaccharide, lipid, lipid assembly, non-biological polymer, or polymeric microparticle. Another class of preferred conjugated substances includes particles or fibers composed of silica or other glasses, useful for preparing optical devices for remote sensing.

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates (AntiVirals, Inc., Corvallis Oreg.), or peptide nucleic acids such as N-(2-aminoethyl)glycine units.

In a preferred embodiment, the conjugated substance ($S_C$) is a carbohydrate that is typically a polysaccharide, such as a dextran, FICOLL, heparin, glycogen, amylopectin, mannan, inulin, starch, agarose and cellulose. Alternatively, the carbohydrate is a polysaccharide that is a lipopolysaccharide. Preferred polysaccharide conjugates are dextran, FICOLL, or lipopolysaccharide conjugates.

In another embodiment, the conjugated substance ($S_C$), is a lipid moiety (typically having 6–60 carbons), including glycolipids, phospholipids, sphingolipids, and steroids. Alternatively, the conjugated substance is a lipid assembly, such as a liposome. The lipid moiety may be used to retain the conjugated substances in cells, as described in U.S. Pat. No. 5,208,148 (incorporated by reference).

Other conjugates of non-biological materials include conjugates of organic or inorganic polymers, polymeric films, polymeric wafers, polymeric membranes, polymeric particles, or polymeric microparticles, including magnetic and non-magnetic microspheres, conducting and non-conducting metals and non-metals, and glass and plastic surfaces and particles. Conjugates are optionally prepared by copolymerization of a compound of the invention that contains an appropriate functionality while preparing the polymer, or by chemical modification of a polymer that contains functional groups with suitable chemical reactivity. Other types of reactions that are useful for preparing conjugates of polymers include catalyzed polymerizations or copolymerizations of alkenes and reactions of dienes with dienophiles, transesterifications or transaminations. In another embodiment, the conjugated substance is a glass or silica, which may be formed into an optical fiber or other structure.

Conjugates typically result from mixing appropriate reactive dyes and the substance to be conjugated in a suitable solvent in which both are soluble. Labeling of insoluble polymers or silica can be performed in a suspension of the insoluble polymer in a suitable solvent. For those reactive groups that are photoactivated, conjugation requires illumination of the reaction mixture to activate the reactive group.

Synthesis

There are typically three components to the methodology used to prepare the compounds of the invention. The first involves the formation of the crown ether chelate itself, the second involves the appropriate derivatization of the secondary amine nitrogen atoms of the crown ether chelate, and the third involves modification of the crown ether chelate by forming a reactive functional group, covalently attaching a conjugate, or covalently attaching a DYE moiety to form an indicator. Although these synthetic components are typically performed in the order given, they may be carried out in any other suitable sequence. For example, a portion of the chelate may be derivatized with a fluorescent dye prior to formation of the complete chelate ring.

Where the P and Q moieties are both oxygen, and $E^1$ is ethylene, the crown ether chelate is typically prepared by acylation of a bis-(2-aminophenoxy)ethane with a bis-(acid chloride), such as diglycolyl chloride, followed by reduction of the resulting bis-amide to the corresponding bis-secondary amine. Selection of the appropriate bis-acid chloride results in the particular desired crown ether (as in Examples 64–69 and 70).

The secondary amine nitrogen atoms present in the crown ether are typically derivatized with an alkylating agent. As the metal binding ability of the resulting crown ether is significantly influenced by the nature of the amine substituents, careful selection of the alkylating agent may be necessary to prepare a reporter for a particular target ion. Where the crown nitrogens are alkylated by methyl bromoacetate, the resulting bis-aza-crown ether is typically selective for sodium ions. If the alkylating agent is 2-picolyl chloride, the resulting crown ether is typically selective for zinc ions. As discussed above, the presence of esters vs. carboxylic acids on the amine nitrogen substituents may influence the relative binding affinity of selected target ions. Selection of an alkylating agent that incorporates a precursor to a reactive functional group is useful for producing chemically reactive compounds of the invention, as well as acting as a useful intermediate for preparing conjugates, as described above. Additionally, an alkylating agent that incorporates a reporter DYE results in a crown ether compound that functions as an indicator for selected target ions.

More typically, the crown ether chelate is derivatized at the benzo ring of the crown ether. As described above, typically a suitable crown ether is prepared, and then bound to a DYE moiety. In one aspect of the invention, an ortho-hydroxy aromatic aldehyde is treated with a chloromethyl heterocycle to yield a fused reporter (as described in Example 46). In another aspect of the invention, derivatization with a DYE moiety is carried out by modifying a crown ether that possesses an aldehyde or ketone functional group.

In one aspect of the invention, the crown ether is substituted by an aldehyde and the fluorophore precursors and the crown ether are combined under anaerobic or non-oxidative conditions (e.g., under nitrogen), and subsequently oxidized using a mild oxidant (e.g., a quinone oxidant, preferably DDQ or chloranil). Where xanthene fluorophore precursors are condensed under anaerobic conditions, the resulting fluorophore is the non-fluorescent dihydro species, which may be utilized without prior oxidation as a sensor for oxidative subenvironments, e.g., in cells.

In yet another aspect of the invention, the crown ether is substituted by a carboxylic acid or by an aldehyde that is converted to the carboxylic acid in the course of synthesis of the crown ether. The chelating moiety is then condensed with the fluorophore precursors to yield the resulting indicator directly.

Synthesis of conventional xanthene dyes such as fluoresceins, rhodamines and rhodols typically involve the condensation of two equivalents of resorcinol (for fluoresceins), aminophenol (for rhodamines) or a mixture of a resorcinol and an aminophenol (for rhodols) with a carbonyl-containing moiety such as a phthalic acid derivative or benzaldehyde. In the synthesis of the xanthene indicators of the invention, the desired resorcinol or aminophenol is condensed with the substituted crown ether, yielding either the reduced xanthene (where the crown ether contains an aldehyde) or the oxidized xanthene (where the crown ether contains a carboxylic acid or acyl halide) bound directly to the chelating moiety.

An oxidation step is typically required after condensation of a formyl-substituted crown ether with the fluorophore precursors. Optionally, the dihydro condensation product is isolated and subsequently oxidized with air or by standard chemical oxidants, such as chloranil. For some fluorophores, the oxidation reaction is enhanced by acidic reaction conditions. These mild oxidation reaction conditions tolerate a wide variety of substituents on the fluorophore and/or crown ether of the resulting indicators.

Unsymmetrical xanthene dyes are typically constructed by statistical methods, using a 1:1 mixture of the desired resorcinols or aminophenols in the condensation reaction, and purifying the desired product from the statistical mix of products using methods known in the art.

The synthesis of polyazaindacene dyes, particularly dipyrrometheneboron difluoride dyes, has been well documented (U.S. Pat. Nos. 4,774,339, 5,187,288, 5,248,782, 5,274,113, 5,338,854 and 5,433,896, all incorporated by reference). The procedure typically consists of an acid-catalyzed condensation of a benzaldehyde with a pyrrole that has a hydrogen at the 2-position, followed by in situ oxidation of the condensed intermediate by air, oxygen or a chemical oxidant such as 2,3-dichloro-5,6-dicyano-1,4-benzoquinone. The condensation of two appropriately substituted pyrroles, each having a hydrogen at the 2-position, with a formyl-substituted crown ether, followed by in situ oxidation of the condensed intermediate and treatment with a boron trifluoride etherate yields the dipyrrometheneboron difluoride indicators of the invention. Alternatively, the indicators are formed via the direct condensation of a carboxyl- or chlorocarbonyl-substituted crown ether with two equivalents of appropriately substituted pyrroles, which may be the same of different, provided each has a hydrogen at the 2-position. The latter procedure does not require oxidation.

Post-condensation modifications of both the crown ether and the fluorophore moiety are typically strictly analogous to known methods of indicator modification. For example, the reduction of nitro substituents to amino groups, the conversion of carboxy substituents to cyano groups, and the preparation of esters of carboxylic acids, including acetoxymethyl esters. Additionally, salts and counterions of the indicators of the invention are readily converted to other salts by treatment with ion-exchange resins, selective precipitation, and basification, as is well-known in the art.

Post-condensation modifications of xanthylium dyes are well known. For instance, the xanthenone portion of the dye can be halogenated by treatment with the appropriate halogenating agent, such as liquid bromine. Xanthenes containing unsaturated fused rings can be hydrogenated to the saturated derivatives.

The reduced and oxidized versions of the xanthene indicators are freely interconvertible by well-known oxidation or reduction reagents, including borohydrides, aluminum hydrides, hydrogen/catalyst, and dithionites. Care must be exercised to select an oxidation or reducing agent that is compatible with the crown ether chelator. A variety of oxidizing agents mediate the oxidation of dihydroxanthenes, including molecular oxygen in the presence or absence of a catalyst, nitric oxide, peroxynitrite, dichromate, triphenyl-carbenium and chloranil. The dihydroxanthenes are also oxidized electrochemically, or by enzyme action, including horseradish peroxidase in combination with peroxides or by nitric oxide.

Rather than condensing the DYE moiety precursors directly with a substituted crown ether, the preformed DYE moiety may be covalently bound to the crown ether via a conventional cross-linking reaction. A wide variety of chemically reactive or potentially chemically reactive and fluorescent fluorescein, rhodamine, rhodol, benzoxanthenes, dibenzoxanthene and other xanthene oxygen heterocycles that absorb maximally beyond about 490 nm are commercially available as described by Haugland, HANDBOOK OF FLUORESCENT PROBES AND RESEARCH CHEMICALS (7th ed., 1999), as described above, or in other literature references. The nature of the bond that links DYE moiety to the crown ether chelate appears to have an effect on the optical response of the DYE moiety to ion binding, sometimes a significant effect. Acceptability of the linking chemistry can be determined by titration of the resultant indicator with the ion of interest over the target range of response (as described in Example 71).

Method of Use

The crown ether compounds of the invention are useful for any application where it is desirable to complex a target metal ion. Selected crown ether compounds of the invention may be useful as ionophores, that is, they facilitate the transport of selected target ions across cell membranes. Where the crown ether compound is bound to a conjugated substance that is a polymeric matrix, such as a microparticle, or agarose, the compounds are useful for depleting a sample solution of a selected target ion, particularly where the polymeric matrix is used to pack a chromatography column. Other crown ether compounds (those bound to a DYE moiety) are useful as colorimetric or fluorescent indicators for a selected target ion.

In order for a particular indicator of the present invention to be useful, it must exhibit a detectable change in spectral properties upon complexation of the desired metal ion (target ion) in the chelating moiety. Preferably the change in spectral properties is a change in fluorescence properties. More preferably, the instant indicators display an intensity increase or decrease in emission energy upon the complexation of the desired target ion.

The specific indicator used in an assay or experiment is selected based on the desired affinity for the target ion as determined by the expected concentration range in the sample, the desired spectral properties, and the desired selectivity. Initially, the suitability of a material as an indicator of ion concentration is commonly tested by mixing a constant amount of the indicating reagent with a measured amount of the target ion under the expected experimental conditions.

Preferred indicators display a high selectivity, that is, they show a sufficient rejection of non-target ions. The interference of a non-target ion is tested by a comparable titration of the indicator with that ion. Although preferred target ions for most indicators of the present invention are $Na^+$, and $K^+$, any ion that yields a detectable change in absorption wavelengths, emission wavelengths, fluorescence lifetimes or other measurable optical property over the concentration range of interest is potentially measured using one of the indicators of this invention. Modifications to the electronic structure of the crown ether or indicator to produce an indicator having the appropriate combination of binding affinity, ion selectivity and spectral response for a wide variety of metal ions.

In one embodiment of the invention, the target ions for the indicators of the present invention are selected from $Li^+$, $Na^+$, $K^+$, $Cs^+$, $Ca^{2+}$, $Zn^{2+}$, $Mg^{2+}$, $Rb^+$, $Tb^{3+}$ or $Eu^{3+}$. In another embodiment of the invention, the target ions are selected from $Li^+$, $Na^+$, $K^+$, $Ca^{2+}$, $Zn^{2+}$, and $Mg^{2+}$. Additional target ions for selected embodiments of the present indicators also include $Mn^{2+}$, $F^{2+}$, $Fe^{3+}$, $Co^{2+}$, $Ni^{2+}$, $Cu^{2+}$, $Cu^+$, $Zn^{2+}$, $Al^{3+}$, $Cd^{2+}$, $Ag^+$, $Au^+$, $Tl^+$, $Pd^{2+}$, $Hg^{2+}$, $Hg^+$, $Sn^{2+}$, $Pb^{2+}$, $Sr^{2+}$, $Ba^{2+}$, $Mo^{3+}$, $Ga^{3+}$, $In^{3+}$, $La^{3+}$, $Eu^{3+}$, $Tb^{3+}$, $Dy^{3+}$, $Ru^{3+}$, $Sc^{3+}$, $As^{3+}$, $Sb^{3+}$, $Cr^{3+}$, $Bi^{3+}$, $Ce^{3+}$, $Ce^{4+}$, $Pd^{2+}$, $Pt^{2+}$ and $Pt^{4+}$ ions. In yet another embodiment of the invention, the target ions of the instant indicators are $Fe^{2+}$, $Fe^{3+}$, $Co^{2+}$, $Ni^{2+}$, $Cu^{2+,}$ $^{Cu+}$, $Zn^{2+}$, $Al^{3+}$, $Cd^{2+}$, $Hg^{2+}$, $Pb^{2+}$, $Ba^{2+}$, $La^{3+}$, $Tb^{3+}$, $Cr^{3+}$ ions. In yet another embodiment, the target ions are selected from the group consisting of $Fe^{3+}$, $Ni^{2+}$, $Cu^{2+}$, $Cu^+$, $Hg^{2+}$, or $Pb^{2+}$.

The indicator is generally prepared for use as a detection reagent by dissolving the indicator in solution at a concentration that is optimal for detection of the indicator at the expected concentration of the target ion. Modifications that are designed to enhance permeability of the indicator through the membranes of living cells, such as acetoxymethyl esters and acetates, may require the indicator to be predissolved in an organic solvent such as dimethylsulfoxide (DMSO) before addition to a cell suspension, where the indicators then readily enter the cells. Intracellular enzymes cleave the esters to the more polar acids and phenols that are then well retained inside the cells. For applications where permeability of cell-membranes is required, the indicators of the invention are typically substituted by only one fluorophore.

A specific indicator of the present invention is useful for the detection and/or quantification of a desired target ion, when the binding of the target ion in the metal ion-binding moiety of the indicator results in a detectable change in spectral properties. Preferably, the change in spectral properties is a detectable fluorescence response.

A detectable fluorescence response, as used herein, is a change in a fluorescence property of the indicator that is capable of being perceived, either by direct visual observation or instrumentally, and the presence or magnitude of which is a function of the presence of a target metal ion in the test sample. This change in a fluorescence property is typically a change in fluorescence quantum yield, fluorescence polarization, fluorescence lifetime, a shift in excitation or emission wavelength or a combination of these effects. The detectable change in a given spectral property is generally an increase or a decrease. However, spectral changes that result in an enhancement of fluorescence intensity and/or a shift in the wavelength of fluorescence emission or excitation are also useful. The change in fluorescence on ion binding is usually due to conformational or electronic changes in the indicator that may occur in either the excited or ground state of the fluorophore, due to changes in electron density at the ion binding site, due to quenching of fluorescence by the bound target metal ion, or due to any combination of these or other effects.

A preferred indicator for a specific target ion is an indicator that shows at least a two-fold change in net fluorescence emission intensity (either higher or lower), or a 1 nanosecond difference in fluorescence lifetime (either shorter or longer), preferably a five-fold or greater change in net fluorescence emission intensity or a 100% change in fluorescence lifetime in response to the target ion. Alternatively, an indicator that exhibits a shift in excitation or emission wavelength of at least 10 nm (either to shorter or longer wavelength) is also preferred, more preferably exhibiting a shift of 25 nm or greater.

The response of an individual indicator to a specific metal ion is dependent on the properties of indicator in the presence and absence of the target ion, the relative electron densities of the dye and metal binding site and the ability of metal ions to quench fluorescence emission when in close proximity to a fluorophore (heavy atom quenching). In one embodiment of the invention, the indicator is essentially nonfluorescent or has low fluorescence in target ion-free solution and exhibits an increase in fluorescence intensity or fluorescence lifetime (or both) upon target metal ion binding. In yet another embodiment of the invention, the fluorescence intensity remains approximately the same but there is a shift in the excitation or emission spectrum, or both, upon metal ion binding.

The optical response of the indicating reagent is determined by changes in absorbance or fluorescence, preferably fluorescence. If absorbance measurements are used to determine ion concentrations, then it is usually optimal to adjust the optical density of the indicator in the sample over the range of analyte concentration to a value of approximately 0.02 to 2.5 (most preferably 0.1 to 1). For fluorescence measurements, the concentration of the indicator will depend mostly on the sensitivity of the equipment used for its detection.

If the optical response of the indicator will be determined using fluorescence measurements, samples are typically stained with indicator concentrations of $10^{-9}$ M to $10^{-2}$ M. The most useful range of analyte concentration is about one log unit above and below the dissociation constant of the ion-indicator complex. This dissociation constant is determined by titration of the indicator with a known concentrations of the target ion, usually over the range of virtually zero concentration to approximately 100 millimolar of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects need to be taken into account when calibrating an indicator.

The indicator is combined with a sample in a way that will facilitate detection of the target ion concentration in the sample. The sample is generally a fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors. Detection and quantitation of the target ion in a sample can help characterize the identity of an unknown sample, or facilitate quality control of a sample of known origin.

In one embodiment of the invention, the sample contains cells, and the indicator is combined with the sample in such a way that the indicator is present within the sample cells. By selection of the appropriate chelating moiety, fluorophore, and the substituents thereon, indicators are prepared that will selectively localize in desired organelles, and provide measurements of the target ion in those organelles. Conjugates of the indicators of the invention with organelle-targeting peptides are used to localize the indicator to the selected organelle, facilitating measurement of target ion presence or concentration within the organelle (as described in U.S. Pat. No. 5,773,227 to Kuhn et al., (1998), incorporated by reference). Alternatively, selection of a lipophilic fluorophore, or a fluorophore having predominantly lipophilic substituents will result in localization in lipophilic environments in the cell, such as cell membranes. Selection of cationic indicators will typically result in localization of the indicator in mitochondria.

In another aspect of the invention, a composition of matter comprises any of the compounds described above, and optionally includes a metal ion. In one embodiment, the compounds of the invention, in any of the embodiments described above, are associated, either covalently or noncovalently, with a surface such as a microfluidic chip, a silicon chip, a microscope slide, a microplate well, or another solid matrix, and is combined with the sample of interest as it flows over the surface. The detectable optical response is therefore detected on the matrix surface itself, typically by use of an instrumental. This embodiment of the invention is particularly suited to high-throughput screening using automated methods.

Quantification of target ion levels in samples is typically accomplished using the indicators of the present invention by methods known in the art (Haugland, HANDBOOK OF FLUORESCENT PROBES AND RESEARCH CHEMICALS, 1996, pp., 503–544). For example, the ratiometric measurement of ion concentration provides accurate measurement of ion concentrations by the treatment of the fluorescence data as the ratio of excitation or fluorescence intensities at two wavelengths, rather than the absolute intensity at a single wavelength. Using the ratio method, a number of variables that may perturb the ion concentration measurements are eliminated. In particular, ion-dependent factors that affect the signal intensity, such as nonuniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the indicators of the present invention, the shift in excitation energy upon binding metal ions makes observation of the excitation spectrum a more useful technique. In either case, to achieve maximal utility, the indicator must be calibrated (to compensate for variance in the dissociation constant of the indicator due to ionic strength, viscosity, or other conditions within the sample). To calibrate the indicator, ionophores such as A-23187, gramicidin, valinomycin, or ionomycin are used. Non-ratiometric analysis can also be accomplished by calibration with a second fluorescent dye present in the sample.

The optical response of the indicator to the ion can be detected by various means that include measuring absorbance or fluorescence changes with an instrument, visually, or by use of a fluorescence sensing device. Several examples of fluorescence sensing devices are known, such as fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator is covalently attached to the fiber optic probe material, typically glass or functionalized glass (e.g., aminopropyl glass) or the indicator is attached to the fiber optic probe via an intermediate polymer, such as polyacrylamide. The indicator solution is alternatively incorporated non-covalently within a fiber optic probe, as long as there is a means whereby the target ion can come into contact with the indicator solution.

Kits

Due to the advantageous properties and the simplicity of use of the instant crown ether compounds, they are particularly useful in the formulation of a kit for the complexation, detection, or quantification of selected target ions, comprising one or more compounds or compositions of the invention in any of the embodiments described above (optionally in a stock solution), instructions for the use of the crown ether compound to complex or detect a desired target ion, and optionally comprising additional components. In one aspect, the compounds of the invention are associated with a surface, such as a chip, microplate well, or other solid matrix, and the sample of interest flows over the surface. The detectable optical response is therefore detected on the matrix surface itself.

The additional kit components may be selected from, without limitation, calibration standards of a target ion, ionophores, fluorescence standards, aqueous buffers, and organic solvents. The additional kit components are present as pure compositions, or as aqueous solutions that incorporate one or more additional kit components. Any or all of the kit components optionally further comprise buffers.

The examples below are given so as to illustrate the practice of this invention. They are not intended to limit or define the entire scope of this invention.

EXAMPLES

The following numbering scheme is used throughout the following examples:

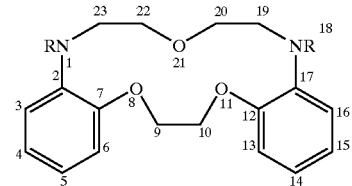

Example 1

Preparation of a tetraaza-crown ether.

2-Nitroaniline is acylated with diglycolyl chloride in anhydrous THF, using 0.5 equivalents of diglycolyl chloride in dilute solution. A 0.1 M THF solution of diglycolyl chloride is slowly added to a 0.1 M THF solution of 2-nitroaniline, containing two equivalents of triethylamine. After TLC indicates consumption of all starting 2-nitroaniline, volatiles are removed in vacuo and the residue is partitioned between water and ethyl acetate. The ethyl acetate layer is concentrated to give Compound 1.

Compound 1

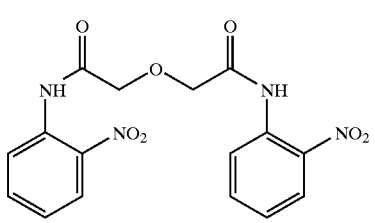

Compound 1 is dissolved in methanol and treated with 20% by weight of 10% palladium on carbon. The resulting mixture is shaken under 40 psi hydrogen until analysis by thin layer chromatography (TLC) indicates the reaction is complete. The reaction mixture is filtered and the bis-aniline 2 is isolated by concentration in vacuo of the filtrate.

Compound 2

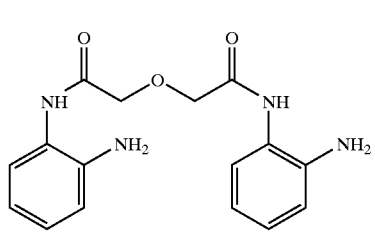

Compound 2 is dissolved in DMF to achieve a 0.1 M solution, then treated with 0.9 equivalents of 1,2-dibromoethane, two equivalents of diisopropylethylamine, and catalytic sodium iodide. The resulting solution is heated until most of 2 is consumed, as judged by TLC analysis. The volatiles are removed in vacuo, and the residue is partitioned between ethyl acetate and water. The ethyl acetate layer is concentrated in vacuo to give compound 3.

Compound 3

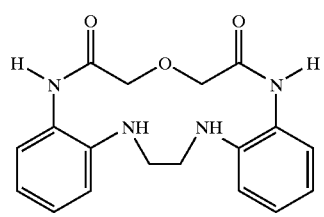

Compound 3 is dissolved in acetonitrile to achieve a 0.5 M concentration. Ten equivalents of formaldehyde, as a 37% aqueous solution, are added followed by 4 equivalents of sodium cyanoborohydride. The pH of the reaction mixture is adjusted to 7 with acetic acid, and the resulting solution is stirred until TLC analysis indicates consumption of 3 and formation of 4. Volatiles are removed in vacuo, and the residue is partitioned between ethyl acetate and water. The ethyl acetate layer is concentrated in vacuo to give compound 4.

Compound 4

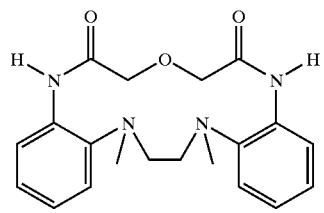

Compound 4 is dissolved in THF at 1 M concentration, and treated with 10 equivalents of borane-THF (1M). The resulting solution is heated at reflux until 4 is consumed and 5 is formed, as judged by TLC analysis. The reaction is quenched by addition of 5% aqueous sodium hydroxide, followed by extraction with ethyl acetate. The ethyl acetate layer is concentrated in vacuo to give 5.

Compound 5

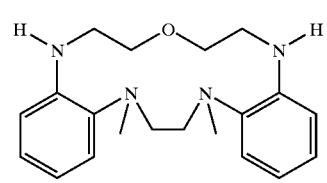

Compound 5 is dissolved in DMF at 0.5 M concentration. Ten equivalents of methyl bromoacetate and 4 equivalents of diisopropylethylamine are added, and the resulting solution is stirred at 100 degrees centigrade until TLC analysis indicates consumption of 5 and formation of 6. Volatiles are removed in vacuo, and the residue is partitioned between water and ethyl acetate. The ethyl acetate layer is concentrated in vacuo to give 6, which can be further purified by flash chromatography on silica gel using methanol in chloroform as eluant.

Compound 6

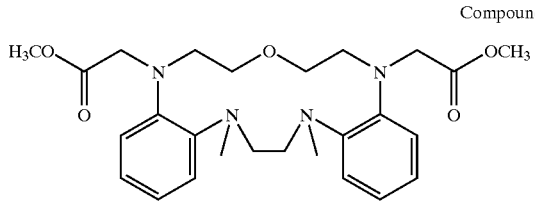

Example 2

Preparation of (2'-Nitrophenoxy)-2-chloroethane (102).

A suspension of 2-nitrophenol 101 (50.0 g, 0.36 mol), 1-bromo-2-chloroethane (45 mL, 0.54 mol), and $K_2CO_3$ (100.0 g, 0.72 mol) in DMF (200 mL) was stirred at 90° C. for 2 h, cooled to room temperature, poured into ice-water, filtered, washed with $H_2O$ and dried to give Compound 102, 70.3 g (96%) as a yellow solid.

Compound 102

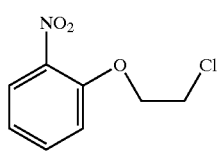

Example 3

Preparation of 1-(5'-methyl-2'-nitrophenoxy)-2-(2"-nitrophenoxy)ethane (104).

A suspension of Compound 102 (60.45 g, 0.30 mol), 5-methyl-2-nitrophenol (50.49 g, 0.33 mol), and $K_2CO_3$ (82.80 g, 0.60 mol) in DMF (450 mL) was stirred at 130° C. for 18 h, cooled to room temperature, poured into ice-water, filtered, washed with $H_2O$ and dried to give Compound 104, 89.50 g (93.5%) as an orange solid.

Compound 104

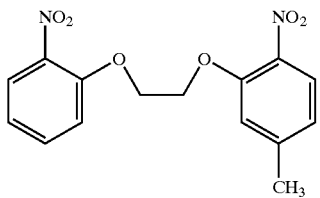

Example 4
Preparation of 1-(2'-amino-5'-methylphenoxy)-2-(2"-aminophenoxy)ethane (105).

Compound 104 (24.0 g, 75 mmol) was hydrogenated over 10% Pd/C (1.5 g) in DMF (250 mL) at 40 psi for 18 h. The mixture was filtered from catalyst through a CELITE pad on a fritted glass filter. The filtrate was evaporated and ether (50 mL) was added. The product was filtered, washed with ether and dried to give compound 105, 18.0 g (95%) as a brown solid.

Compound 105

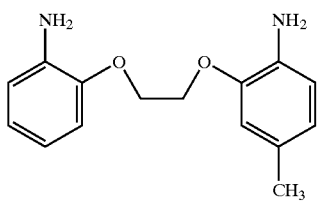

Example 5
Preparation of 5-methyl-19,23-dioxo-DDTCPD (106).

To a stirred mixture of diamine 105 (13.10 g, 50 mmol) and $Et_3N$ (20.8 mL, 150 mmol) in dry THF (2.5 L) was slowly added over 12 h a solution of diglycolyl dichloride (6.3 mL, 55 mmol) in dry THF (0.5 L). The reaction mixture was stirred for 6 h, filtered from the precipitated hydrochloride, and washed with THF. The combined organic filtrate was evaporated. The residue was dissolved in $CHCl_3$ (800 mL) and washed successively with 0.5 M HCl, $H_2O$, saturated $NaHCO_3$ then saturated NaCl. The organic layer was dried over $MgSO_4$ and evaporated. Ether (100 mL) was added and the precipitated product was filtered, washed with ether and dried to give Compound 106, 16.0 g (90%) as an off-white solid.

Compound 106

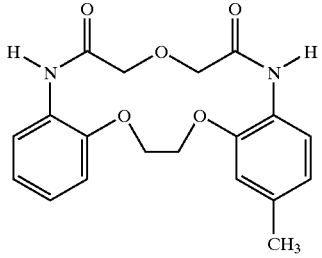

Example 6
Preparation of 5-methyl-DDTCPD (107).

To a suspension of diamide 106 (15.60 g, 44 mmol) in dry THF (400 mL) was added a 1 M solution of $BH_3$-THF complex in dry THF (390 mL, 390 mmol). The mixture was stirred at 70° C. for 16 h. Dry methanol (300 mL) was added dropwise over 1 h into a boiling mixture with strong gas evaluation. The mixture was heated at reflux for 2 h, cooled to room temperature, evaporated and co-evaporated with MeOH to destroy the borane complex. Ether (100 mL) was added. The solid product was filtered, washed with ether and dried to give Compound 107, 12.3 g (85%) as an off-white solid.

Compound 107

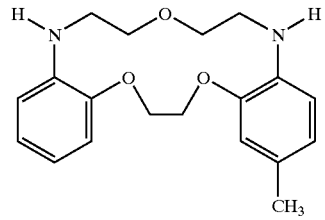

Example 7
Preparation of 1,18-bis(methoxycarbonylmethyl)-5-methyl-DDTCPD (108).

A mixture of diamine 107 (6.56 g, 20 mmol), methyl bromoacetate (38 mL, 400 mmol), diisopropylethylamine (DIPEA) (104 mL, 600 mmol), and NaI (1.50 g, 10 mmol) in MeCN (300 mL) was heated at reflux for 70 h. After cooling to room temperature, the MeCN was evaporated. The residue was dissolved in $CHCl_3$, washed with 1% AcOH then $H_2O$, dried and evaporated. The residual oily product was cooled to 0° C. and washed with cold hexane to remove most of the alkylating reagent. The crude product 108 was used immediately in the next step without further purification.

Compound 108

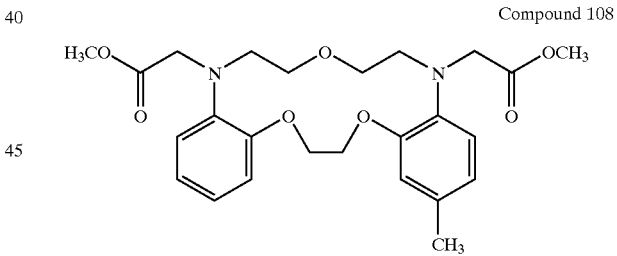

Example 8
Preparation of 1,18-bis(methoxycarbonylmethyl)-5-formyl-14-methyl-DDTCPD (109).

To a stirred solution of the Vilsmeier reagent prepared from $POCl_3$ (4.65 mL, 50 mmol) and 30 mL DMF was added over 5 min a solution of Compound 108 (4.8 g, 10 mmol) in DMF (20 mL). The mixture was stirred for 16 h, cooled by the addition of ice and neutralized with saturated $K_2CO_3$ to pH 7–8. The suspension was extracted with $CHCl_3$, washed successively with 0.1 M HCl, saturated NaCl, saturated $NaHCO_3$ and saturated NaCl, then evaporated. The residue was dissolved in $CHCl_3$ and chromatographed on $SiO_2$ with an EtOAc gradient in hexanes (20% to 30%) to give aldehyde 109, 2.60 g (52%) as colorless crystals.

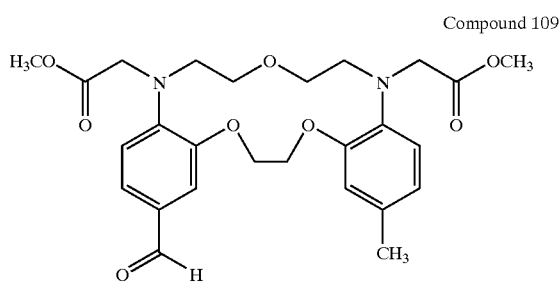

Compound 109

Example 9
Preparation of 1,18-bis(methoxycarbonylmethyl)-4-benzyloxy-5-formyl-14-methyl-DDTCPD (117).

Compound 117 was prepared analogously with Compound 109, starting with 5-methyl-2-nitrophenol in place of 2-nitrophenol, and utilizing 4-benzyloxy-2-nitrophenol in place of 5-methyl-2-nitrophenol.

Compound 117

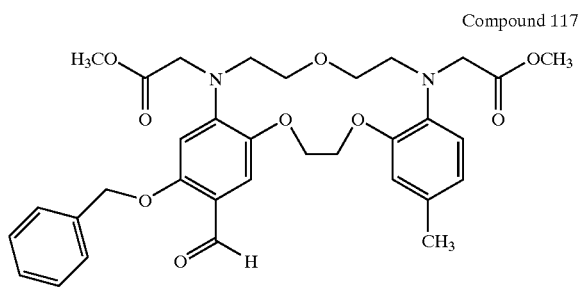

Example 10
Preparation of 1,18-bis(methoxycarbonylmethyl)-5-formyl-4-hydroxy-14-methyl-DDTCPD (118).

Compound 117 (3.06 g, 5.0 mmol) was hydrogenated over 10% Pd/C (0.50 g) in AcOH (100 mL) at 50 psi for 5 h. The mixture was filtered through a CELITE pad on a fritted glass filter. The filtrate was evaporated, ether (50 mL) was added, the product was filtered, washed with ether and dried to give Compound 118, 2.13 g (82%) as a colorless solid.

Compound 118

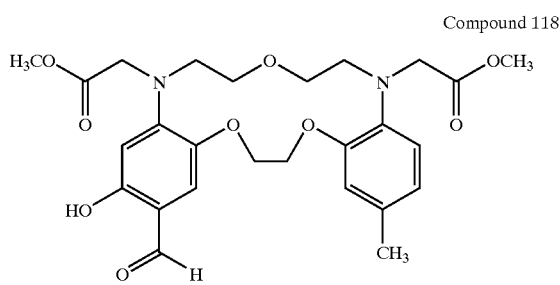

Example 11
Preparation of 1,18-bis(methoxycarbonylmethyl)-4-t-butoxycarbonylmethoxy-5-formyl-14-methyl-DDTCPD (119).

To a suspension of Compound 118 (0.800 g, 1.55 mmol), $K_2CO_3$ (1.04 g, 7.5 mmol) and NaI (0.03 g, 0.2 mmol, catalyst) in DMF (10 mL) was added dropwise t-butyl bromoacetate (0.45 mL, 3.0 mmol). The mixture was stirred for 16 h, diluted with $H_2O$, extracted with $CHCl_3$, dried over $MgSO_4$ and evaporated. The residue was dissolved in hexane: EtOAc (1:1) and chromatographed on silica gel with 40% EtOAc in hexanes to give aldehyde 119, 0.875 g (90%) as colorless crystals.

Compound 119

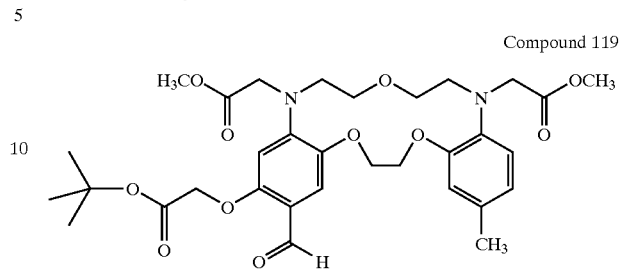

Example 12
Preparation of 1,18-bis(cyanomethyl)-5-methyl-DDTCPD (120).

A stirred mixture of diamine 107 (3.38 g, 10 mmol), bromoacetonitrile (14 mL, 200 mmol), DIPEA (26 mL, 150 mmol), NaI (1.5 g, 10 mmol; catalyst) in MeCN (150 mL) was heated at reflux for 70 h. After cooling to room temperature the MeCN was evaporated. The residue was dissolved in $CHCl_3$ (800 mL), washed with $H_2O$, dried over $MgSO_4$ and evaporated. The residue was chromatographed on $SiO_2$ with 40% EtOAc in hexanes to give Compound 120, 3.56 g (90%) as a colorless solid.

Compound 120

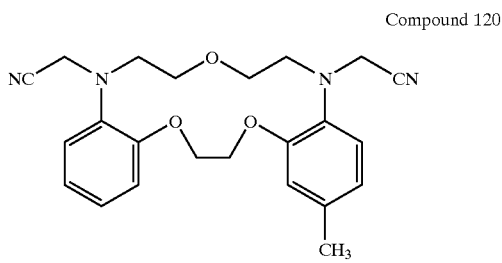

Example 13
Preparation of 1,18-bis(cyanomethyl)-5-formyl-14-methyl-DDTCPD (121).

To a stirred solution of the Vilsmeier reagent prepared from $POCl_3$ (9.5 mL, 102 mmol) and 60 mL DMF was added over 5 min to a solution of Compound 120. The mixture was stirred for 100 h at 40° C., cooled by the addition of ice and neutralized with saturated $K_2CO_3$ to pH 8. The suspension was extracted with $CHCl_3$, washed with $H_2O$, dried over $MgSO_4$ and evaporated. The residue was chromatographed over $SiO_2$ using $CHCl_3$ as eluant to give compound 121, 3.12 g (73%) as colorless crystals.

Compound 121

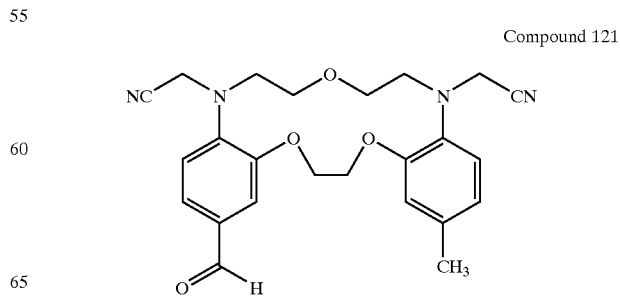

Example 14
Preparation of 1,18-bis(cyanomethyl)-5-(2',5'-dioxacyclopentyl)-14-methyl-DDTCPD (122).

A mixture of aldehyde 121 (3.08 g, 7.3 mmol), ethylene glycol (8 mL, 140 mmol), p-toluenesulphonic acid (0.20 g, catalyst) and benzene (80 mL) was refluxed with a Dean-Stark trap for 4 h. After cooling to room temperature the mixture was evaporated. The residue was dissolved in CHCl₃ (300 mL), washed with saturated NaHCO₃, dried over MgSO₄, and evaporated to give compound 122, 2.82 g (85%) as an orange solid. Compound 122 was pure on TLC and used in the next step without additional purification.

Compound 122

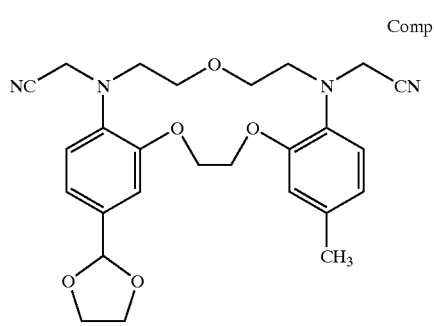

Example 15
Preparation of 1,18-bis(carbamoylmethyl)-5-formyl-14-methyl-DDTCPD (123).

To a solution of Compound 122 (0.200 g, 0.44 mmol) in MeOH (25 mL) and 1 M NaOH (15 mL, 15 mmol) was added over 5 min 30% H₂O₂ (5 mL, catalyst). The mixture was stirred for 1 h, then acidified with 1 M HCl to pH 1. The acidified mixture was stirred for 30 min, diluted with 3 M NaOAc (150 mL), extracted with CHCl₃, washed with saturated NaHCO₃, dried over MgSO₄ and evaporated to give aldehyde 123, 0.191 g (95%) as a colorless crystalline material, pure by TLC.

Compound 123

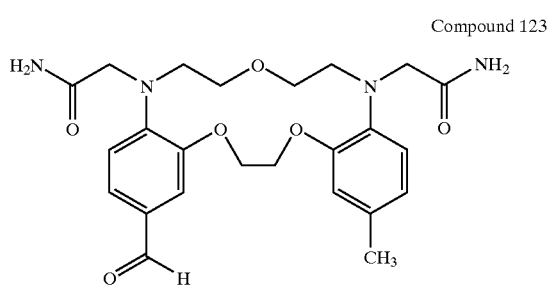

Example 16
Preparation of 1,18-bis(methoxycarbonylmethyl)-14-methyl-5-[2H-fluoro]-DDTCPD (131).

A mixture of aldehyde 109 (1.150 g, 2.3 mmol) and 4-fluororesorcinol (0.670 g, 5.2 mmol) in MeSO₃H (25 mL) was stirred overnight, then poured into 3 M NaOAc (300 mL). The precipitated solid was filtered, washed with H₂O and dried to give compound 131, 1.605 g (97%) as an off-white solid. Compound 131 was unstable to oxidation and was used in the next step without additional purification.

Compound 131

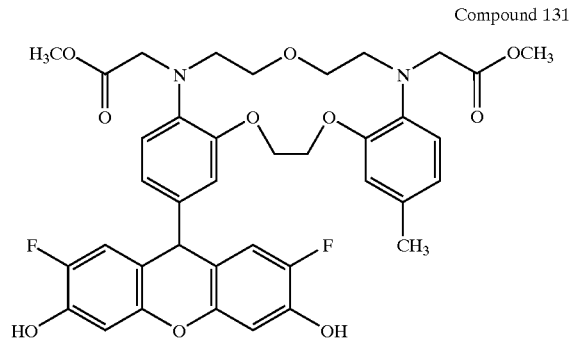

Example 17
Preparation of 1,18-bis(methoxycarbonylmethyl)-14-methyl-5-[fluoro]-DDTCPD (132).

A mixture of Compound 131 (150 mg, 0.21 mmol) and chloranil (246 mg, 1.0 mmol) in MeOH (5 mL) and CHCl₃ (5 mL) was refluxed for 50 h, then cooled to room temperature, filtered from excess oxidizer, and evaporated. The residue was purified by preparative TLC on two SiO₂ plates using CHCl₃:MeOH:AcOH (20:2:1) to give compound 132, 44 mg (20%) as a red-brown solid.

Compound 132

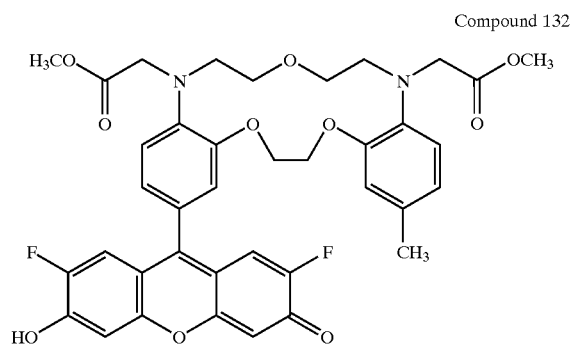

Example 18
Preparation of 1,18-bis(carboxymethyl)-14-methyl-5-[fluoro]-DDTCPD (133).

A mixture of Compound 132 (30 mg, 0.04 mmol) in MeOH (5 mL) and 1 M KOH (1 mL, 1.0 mmol) was stirred for 16 h, then neutralized with 1 M HCl to pH 7, and evaporated to dryness. The residue was purified by preparative TLC on two SiO₂ plates using CHCl₃:MeOH:AcOH (13:3:1) to give compound 133, 21 mg (74%) as a brown solid.

Compound 133

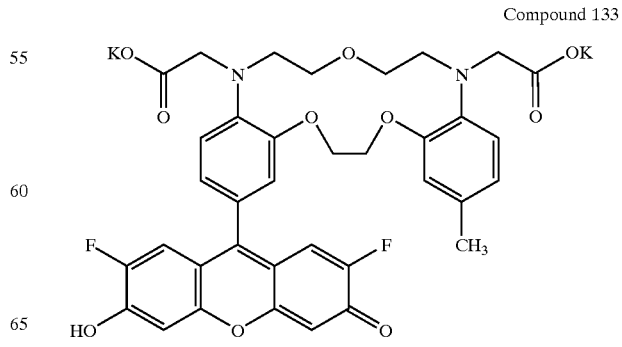

Example 19
Preparation of 1,18-bis(methoxycarbonylmethyl)-14-methyl-5-[fluoro-AM]-DDTCPD (134).

A mixture of Compound 132 (78 mg, 0.1 mmol), bromomethyl acetate (0.05 mL, 0.5 mmol), and DIPEA (0.175 mL, 1 mmol) in DMF (1 mL) was stirred for 2 h, then poured into 1% ACOH (200 mL). The suspension was extracted with CHCl$_3$, washed with H$_2$O, filtered and evaporated. The residue was purified by preparative TLC on two SiO$_2$ plates using 5% MeOH in CHCl$_3$: to give compound 134, 25 mg (32%) as a brown solid.

Example 20
Preparation of 1,18-bis(acetoxymethoxycarbonylmethyl)-14-methyl-5-[fluoro-AM]-DDTCPD (135).

A mixture of Compound 133 (69 mg, 0.1 mmol), bromomethyl acetate (0.05 mL, 0.5 mmol), and DIPEA (0.175 mL, 1 mmol) in DMF (1 mL) was stirred for 2 h, then poured into 1% AcOH (200 mL). The suspension was extracted with CHCl$_3$, washed with H$_2$O, filtered and evaporated. The residue was purified by preparative TLC on two SiO$_2$ plates using 5% MeOH in CHCl$_3$ to give Compound 135 as a brown solid.

Example 21
Preparation of 1,18-bis(methoxycarbonylmethyl)-14-methyl-5-[2H-TMR]-DDTCPD (137).

A mixture of aldehyde 109 (250 mg, 0.5 mmol), 3-dimethylaminophenol (157 mg, 1.1 mmol), and p-toluenesulphonic acid (10 mg, catalyst) in propionic acid (5 mL) was stirred overnight at 60° C., then cooled to room temperature and poured into 3 M NaOAc (100 mL). The precipitated solid was filtered, washed with H$_2$O and dried to give compound 137, 360 mg (97%) as a rose-colored solid. Compound 137 was unstable to oxidation and was used in subsequent reactions without additional purification.

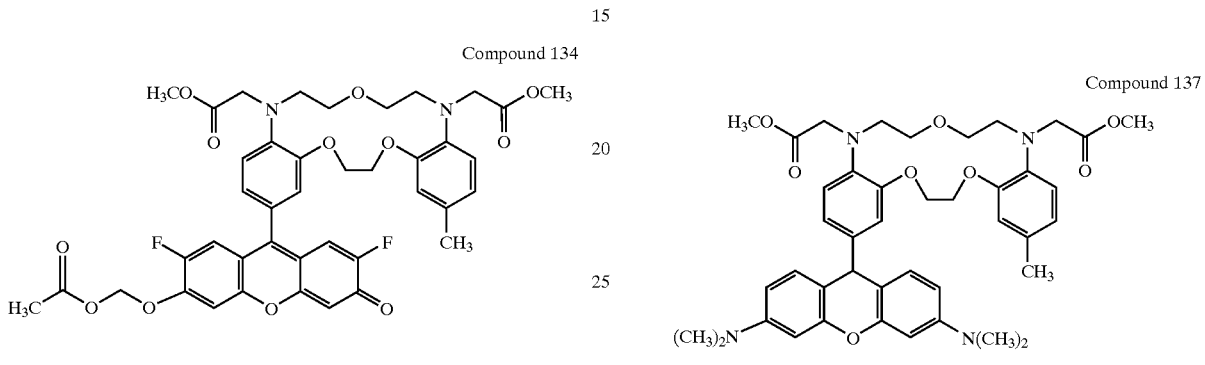

Compound 134

Compound 137

Example 22
Preparation of 1,18-bis(methoxycarbonylmethyl)-14-methyl-5-[TMR]-DDTCPD (138).

A mixture of Compound 137 (660 mg, 0.81 mmol) and chloranil (400 mg, 1.62 mmol) in MeOH (25 mL) and CHCl$_3$ (25 mL) was stirred for 2 h, filtered from excess oxidizer, and evaporated. The residue was purified by chromatography on SiO$_2$ using 9% MeOH and 1% AcOH in CHCl$_3$ as eluant to give the crude product, which was again chromatographed on SiO$_2$ using the same eluant to give Compound 138, 112 mg (19%) as crimson solid.

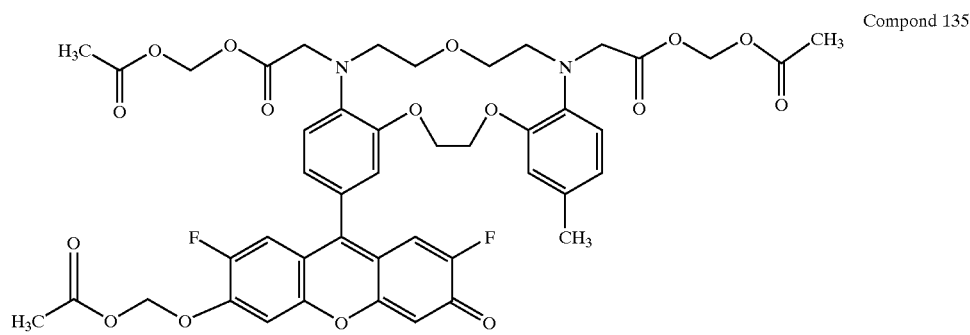

Compond 135

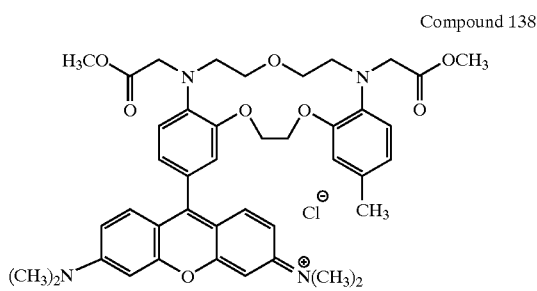

Compound 138

Example 23
Preparation of 1,18-bis(carboxymethyl)-14-methyl-5-[TMR]-DDTCPD potassium salt (139).

A mixture of Compound 138 (40 mg, 0.05 mmol) in MeOH (2 mL) and 1 M KOH (1 mL, 1.0 mmol) was stirred for 16 h, then evaporated to dryness. The residue was purified by chromatography on a SEPHADEX LH-20 column using $H_2O$ as eluant to give salt 139, 8 mg (21%) as red flakes after lyophilization.

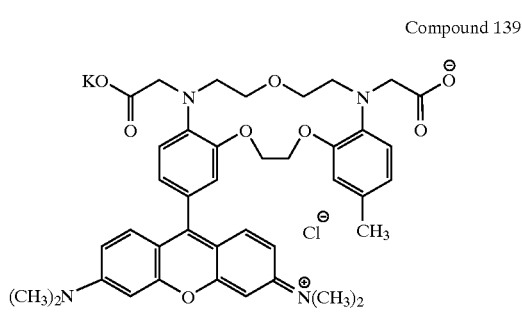

Compound 139

Example 24
Preparation of 1,18-bis(acetoxymethoxycarbonylmethyl)-14-methyl-5-[TMR]-DDTCPD (140).

A mixture of Compound 139 (75 mg, 0.1 mmol), bromomethyl acetate (0.1 mL, 1.0 mmol), and DIPEA (0.35 mL, 2 mmol) in DMF (2 mL) was stirred for 2 h, then poured into 1% AcOH (200 mL). The suspension is extracted with $CHCl_3$, washed with $H_2O$, filtered and evaporated. The residue was purified by preparative TLC on two $SiO_2$ plates using 5% MeOH in $CHCl_3$ to give Compound 140 as a red solid.

Example 25
Preparation of 1,18-bis(methoxycarbonylmethyl)-14-methyl-5-[X-Rhd]-DDTCPD (143).

Compound 143 was prepared analogously to Compound 138, using 8-hydroxyjulolidine rather than m-dimethylaminophenol.

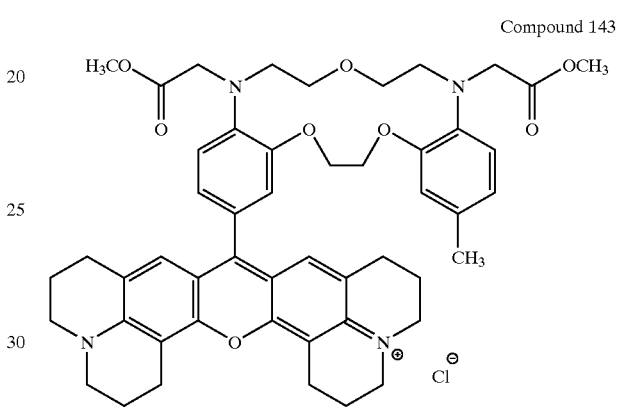

Compound 143

Example 26
Preparation of 1,18-bis(carboxymethyl)-14-methyl-5-[X-Rhd]-DDTCPD potassium salt (144).

Compound 144 was prepared form Compound 138 using the procedure for preparing Compound 139 from Compound 138.

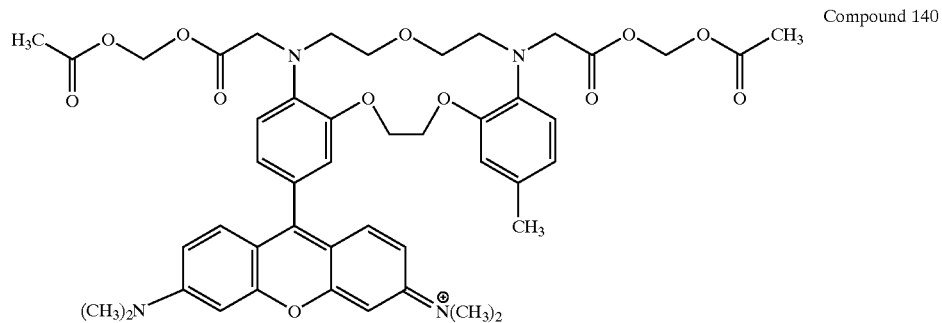

Compound 140

Compound 144

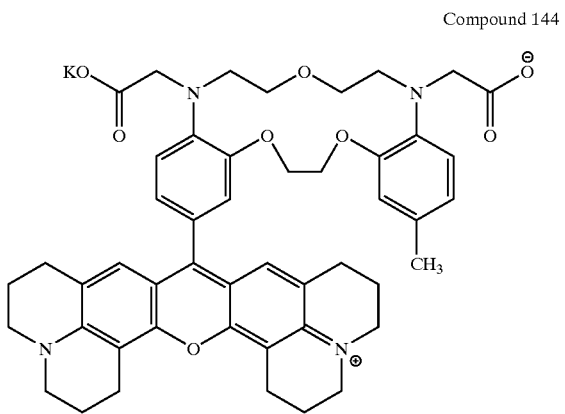

Example 27
Preparation of 1,18-bis(carboxymethyl)-14-methyl-5-[BODIPY]-DDTCPD (145).

To a solution of aldehyde 109 (250 mg, 0.5 mmol) in $CH_2Cl_2$ (20 mL) was added 2,4-dimethylpyrrole (0.125 mL, 1.2 mmol). The solution was stirred for 5 min, then TFA (0.046 mL, 0.6 mmol) is introduced. After 16 h, the mixture was diluted with $CHCl_3$ (150 mL), washed with 2% tetrabutylammonium hydroxide (150 mL) then $H_2O$ then evaporated. The residue was dissolved in toluene (20 mL) and stirred for 3 h with chloranil (148 mg, 0.6 mmol). DIPEA (0.87 mL, 5 mmol) was introduced, followed by $BF_3$ etherate (0.52 mL, 4 mmol). The mixture was evaporated and the residue was purified by chromatography on $SiO_2$ using a gradient of 0–2% MeOH in $CHCl_3$ to give compound 145, 102 mg (28%) as a brown solid.

Compound 145

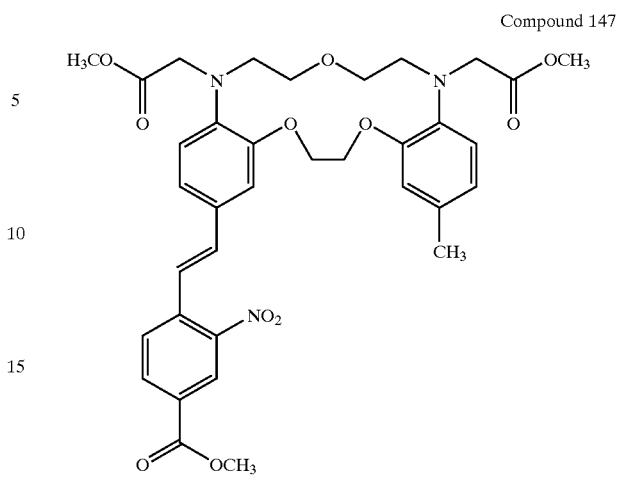

Example 28
Preparation of trans 1-[1',18'-bis-(methoxycarbonylmethyl)-14'-methyl-DDTCPD-5-yl]-2-[4"-methoxycarbonyl-2"-nitrophenyl] ethylene (147).

A mixture of aldehyde 109 (1.00 g, 2.0 mmol), the Wittig base (4-methoxycarbonyl-2-nitrobenzyl)triphenylphosphonium bromide (1.34 g, 2.5 mmol), and $K_2CO_3$ (1.38 g, 10 mmol) in DMF (20 mL) was stirred for 16 h at 95° C. More of the Wittig base (0.500 g, 0.93 mmol) was added and the mixture was stirred for an additional 6 h, then cooled to room temperature and poured into $H_2O$. The solution was acidified with 1 M HCl to pH 3, extracted with $CHCl_3$, dried over $MgSO_4$, and evaporated. The crude product was purified by chromatography on SiO2 using $CHCl_3$ then 2% MeOH in $CHCl_3$ to give compound 147, 0.915 g (68%) as an orange solid.

Compound 147

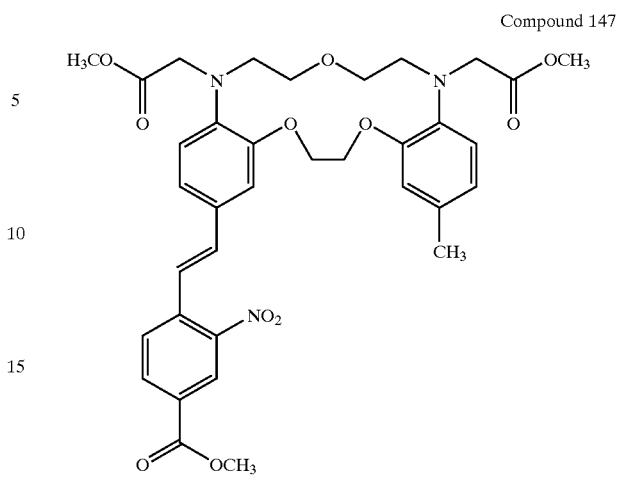

Example 29
Preparation of 1,18-bis(methoxycarbonylmethyl)-5-(6'-methoxycarbonylindolyl-2')-14-methyl-DDTCPD (148).

A mixture of the ethylene derivative 147 (70 mg, 0.1 mmol) and triethylphosphite (3 mL) was heated at 120° C. for 6 h, then evaporated and subsequently co-evaporated with DMF (3×10 mL). The residue was purified by preparative TLC on two $SiO_2$ plates using 7% MeOH in $CHCl_3$ as eluant to give compound 148, 52 mg (80%) as a slightly yellowish solid.

Compound 148

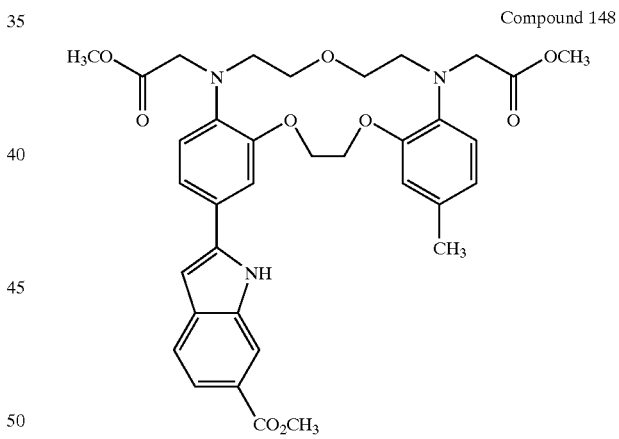

Example 30
Preparation of 1,18-bis(carboxymethyl)-5-(6'-carboxy indolyl-2')-14-methyl-DDTCPD (149).

A mixture of Compound 148 (300 mg, 0.46 mmol), and 1 M KOH (6 mL, 6 mmol) in MeOH (25 mL) was stirred for 16 h. More 1 M KOH (5 mL, 5 mmol) was added and the mixture was stirred for an additional 6 h, then evaporated to half its original volume, and acidified with 1 M HCl to pH 3. The suspension was extracted with $CHCl_3$ then with n-BuOH. The combined organic extract was filtered and was evaporated. Ether (20 mL) was added and the precipitated solid was filtered and washed with ether to give compound 149, 157 mg (57%) as an off-white solid.

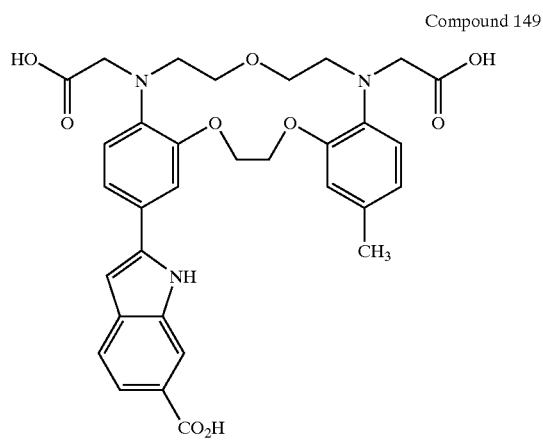

Compound 149

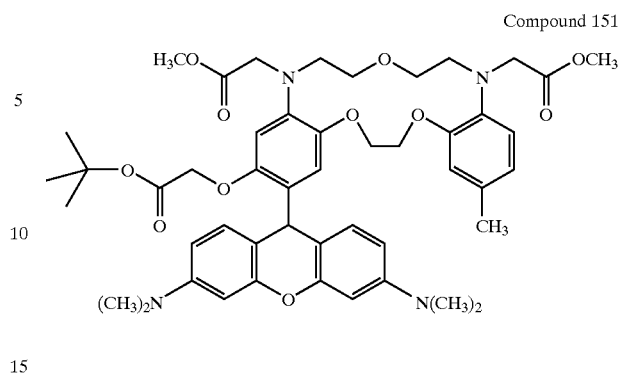

Compound 151

Example 33

Preparation of 4-(t-butoxycarbonylmethyloxy)-1,18-bis (methoxycarbonylmethyl)-14-methyl-5-[TMR]-DDTCPD (152).

A mixture of Compound 151 (2.50 g, 2.9 mmol) and chloranil (1.42 g, 5.8 mmol) in MeOH (100 mL) and $CHCl_3$ (100 mL) was stirred for 4 h, filtered from excess oxidizer, and evaporated. The residue was purified by chromatography on $SiO_2$ using a gradient of 6–10% MeOH and 1% AcOH in $CHCl_3$ to give compound 152, 1.13 g (45%) as a crimson solid.

Example 31
Preparation of 1,18-bis(acetoxymethoxycarboxymethyl)-5-(6'-acetoxymethoxycarboxyindolyl-2')-14-methyl-DDTCPD (150).

A mixture of Compound 149 (72 mg, 0.12 mmol), bromomethyl acetate (0.14 mL, 1.0 mmol), and DIPEA (0.35 mL, 2 mmol) in DMF (5 mL) was stirred for 16 h, poured into 1% AcOH (200 mL), extracted with $CHCl_3$, washed with $H_2O$ then evaporated. The residue was purified by preparative TLC on two $SiO_2$ plates using 5% MeOH in $CHCl_3$ to give Compound 150, 3 mg (3%) as a brown solid.

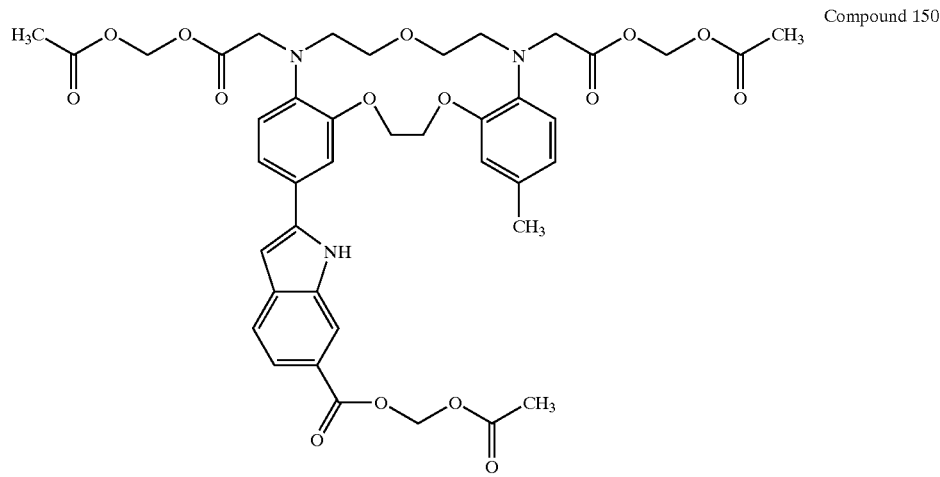

Compound 150

Example 32
Preparation of 4-(t-butoxycarbonylmethyloxy)-1,18-bis (methoxycarbonylmethyl)-14-methyl-5-[2H-TMR]-DDTCPD (151).

A mixture of aldehyde 119 (630 mg, 1.0 mmol), 3-dimethylaminophenol (330 mg, 2.4 mmol), and p-toluenesulphonic acid (20 mg, catalyst) in propionic acid (5 mL) was stirred for 16 h at 60° C., then cooled to room temperature and poured into 3 M NaOAc (150 mL). The precipitated solid was filtered, washed with $H_2O$ and dried to give Compound 151, 360 mg (97%) as a rose solid. Compound 151 is unstable to oxidation and was used in next step without additional purification.

Compound 152

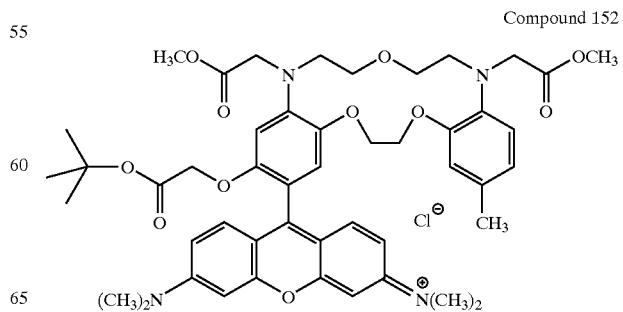

Example 34
Preparation of 4-carboxymethyloxy-1,18-bis(methoxycarbonylmethyl)-14-methyl-5-[TMR]-DDTCPD (153).

A mixture of Compound 152 (500 mg, 0.58 mmol) in CH$_2$Cl$_2$ (20 mL) and TFA (20 mL) was stirred for 4 h, then evaporated and co-evaporated with CHCl$_3$. Ether (25 mL) was added to the residue and the precipitated product was filtered and washed with ether to give Compound 153, 447 mg (95%) as a violet-red solid.

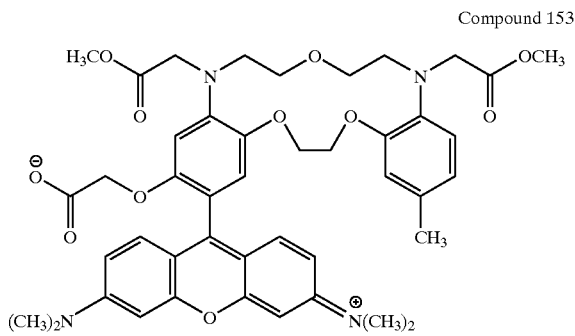

Compound 153

Example 35
Preparation of 4-acetoxymethoxycarbonylmethyloxy-1,18-bis(methoxycarbonylmethyl)-14-methyl-5-[TMR]-DDTCPD (154).

A mixture of Compound 153 (20 mg, 0.1 mmol), bromomethyl acetate (0.025 mL, 0.25 mmol), and DIPEA (0.08 mL, 0.5 mmol) in DMF (1 mL) was stirred for 3 h. More bromomethyl acetate (0.025 mL, 0.25 mmol) and DIPEA (0.08 mL, 0.5 mmol) were added and the mixture was stirred for an additional 3 h, diluted with CHCl$_3$ (100 mL), washed with 1% AcOH then H$_2$O then evaporated. The residue was purified by preparative TLC on two SiO$_2$ plates using 10% MeOH and 0.5% AcOH in CHCl$_3$ to give Compound 154, 12 mg (54%) as a dark red solid.

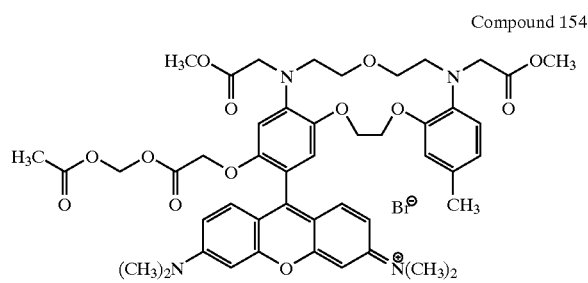

Compound 154

Example 36
Preparation of 4-carboxymethyloxy-1,18-bis(methoxycarbonylmethyl)-14-methyl-5-[TMR]-DDTCPD, succinimidyl ester (155).

To a stirred solution of Compound 153 (162 mg, 0.2 mmol) and pyridine (0.08 mL, 1 mmol) in DMF (5 mL), was added dry N-trifluoroacetoxysuccinimide (90 mg, 0.4 mmol). After 7 h more N-trifluoroacetoxysuccinimide (90 mg, 0.4 mmol) and pyridine (0.08 mL, 1 mmol) were added, and the mixture was stirred for 16 h more. Analytical TLC confirmed the formation of the single product, while starting material 153 was consumed. Compound 155 was very reactive and unstable towards isolation attempts. It was used in further transformations upon preparation in DMF solution without isolation and purification.

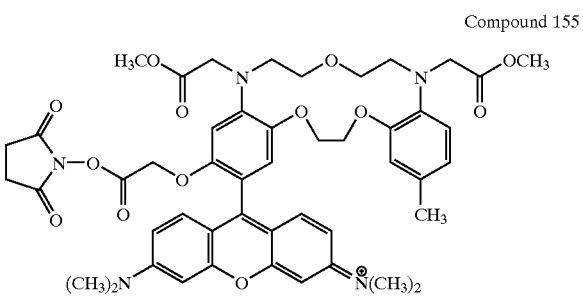

Compound 155

Example 37
Preparation of 4-(N-hexadecylaminocarbonylmethyloxy)-1,18-bis(methoxycarbonylmethyl)-14-methyl-5-[TMR]-DDTCPD (156).

To a stirred solution of succinimidyl ester 155 prepared as in Example 36 from compound 153 (81 mg, 0.1 mmol) in DMF (2 mL) was added dry hexadecylamine (135 mg, 0.5 mmol). The mixture was stirred for 16 h, diluted with CHCl$_3$ (150 mL), washed with 1% AcOH the H$_2$O, dried over MgSO$_4$, and evaporated. The residue was purified by preparative TLC on two SiO$_2$ plates using CHCl$_3$ as eluant to give Compound 156, 57 mg (54%) as a red oil.

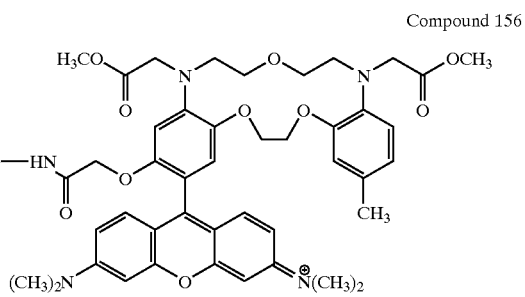

Compound 156

Example 38
Preparation of 4-(N-5'-carboxypentylaminocarbonylmethyloxy)-1,18-bis(methoxycarbonylmethyl)-14-methyl-5-[TMR]-DDTCPD (157).

To a stirred solution of succinimidyl ester 155 prepared as in Example 36 from Compound 153 (81 mg, 0.1 mmol) in DMF (2 mL) was quickly introduced a solution of 5-aminopentanoic acid (40 mg, 0.3 mmol) and 1 M methanolic tetrabutylammonium hydroxide (1 mL, 1 mmol) in H$_2$O (5 mL). The mixture was stirred for 4 h, then diluted with H$_2$O (100 mL), acidified with AcOH to pH 4, extracted with CHCl$_3$, dried over MgSO$_4$ and evaporated. The residue was purified by preparative TLC on two SiO$_2$ plates using 10% MeOH and 2.5% AcOH in CHCl$_3$ as the eluant to give Compound 157, 56 mg (61%) as a red solid.

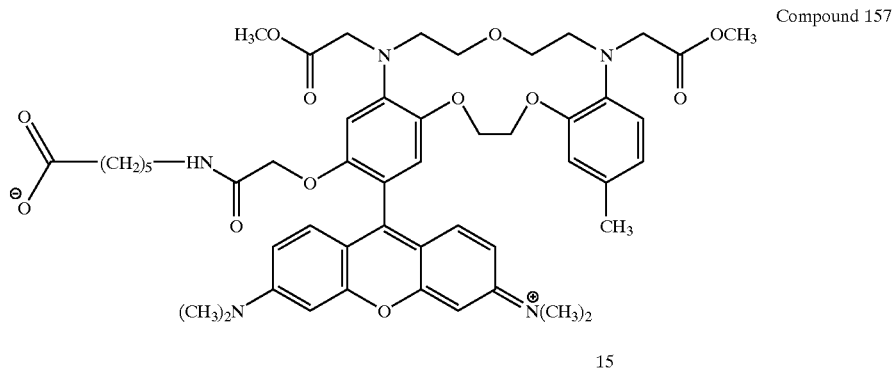

Compound 157

Example 39
Preparation of 4-(N-5'-Carboxypentylaminocarbonylmethyloxy)-1,18-bis(methoxycarbonylmethyl)-14-methyl-5-[TMR]-DDTCPD (157) succinimidyl ester (158).

To a stirred solution of Compound 157 (37 mg, 0.04 mmol) and pyridine (0.08 mL, 1 mmol) in DMF (1 mL), was added dry N-trifluoroacetoxysuccinimide (36 mg, 0.16 mmol). After 4 h, more N-trifluoroacetoxysuccinimide (36 mg, 0.4 mmol) and pyridine (0.08 mL, 1 mmol) are added, and the mixture was stirred for an additional 16 h. The mixture was diluted with $CHCl_3$ (100 mL), washed with 1% AcOH then $H_2O$ then evaporated. Hexanes (5 mL) were added to the residue. The precipitated solid was filtered, washed with hexanes and dried to give Compound 158, 15 mg (37%) as a dark red solid.

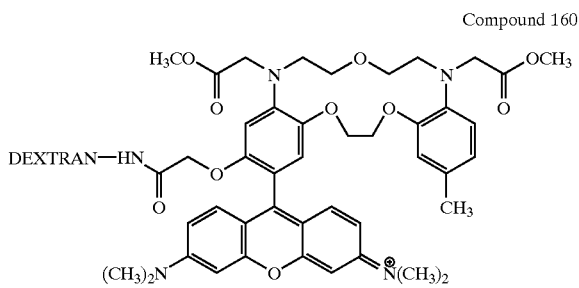

Compound 160

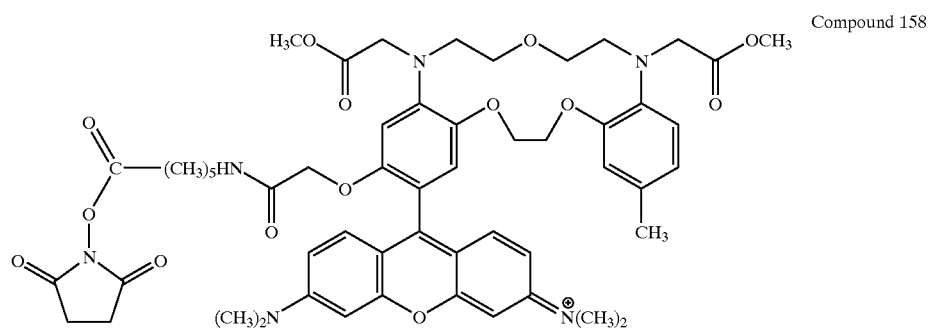

Compound 158

Example 40
Preparation of 4-carboxymethyloxy-1,18-bis(methoxycarbonylmethyl)-14-methyl-5-[TMR]-DDTCPD, dextran conjugate (160).

A solution of succinimidyl ester 155 (81 mg, 0.1 mmol) in DMF (2 mL) was added to 5 mL of aqueous aminodextran (100 mg, 0.037 eq.) and 1 M methanolic tetrabutylammonium hydroxide (1 mL, 1 mmol). The mixture was stirred for 16 h, poured into MeOH (400 mL), and the precipitated conjugate was filtered off and washed with MeOH. The crude product was dissolved in $H_2O$ (3 mL), filtered through a membrane filter and loaded onto a SEPHADEX G-15 resin column pre-equilibrated with $H_2O$. The colored fraction was eluted in a void volume and lyophylized to give labeled dextran 160, (41 mg) as a red solid.

Example 41
Preparation of 4-(N-[(4"-aminophenyl)ethyl-2')carbonylmethyloxy)-1,18-bis(methoxycarbonylmethyl)-14-methyl-5-[TMR]-DDTCPD (161).

To a stirred solution of succinimidyl ester 155 (81 mg, 0.1 mmol) in DMF (2 mL) was added $Et_3N$ (0.14 mL, 1 mmol) followed by 2-(4-aminophenyl)ethylamine (0.05 mL, 0.5 mmol). The mixture was stirred for 2 h, diluted with $CHCl_3$ (150 mL), washed with 1% AcOH then $H_2O$ then evaporated. Ether (5 mL) was added to the residue, and the solid was filtered off, washed with ether and dried to give Compound 161 as a dark red solid, pure on TLC and HPLC.

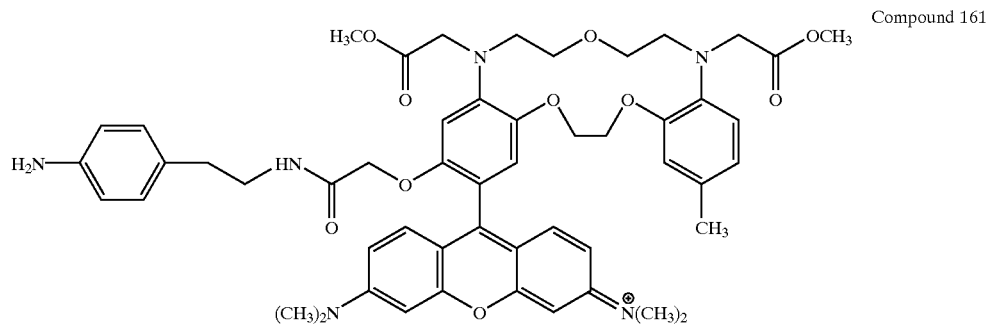

Compound 161

Example 42

Preparation of 4-(N-[(4"-isothiocyanatophenyl)ethyl-2') carbamoylmethyloxy)-1,18-bis(methoxycarbonylmethyl)-14-methyl-5-[TMR]-DDTCPD (162).

To a solution of Compound 161 (9 mg, 0.01 mmol) in AcOH (2 mL) was added a 1 M $CSCl_2$ solution in $CHCl_3$ (0.1 mL, 0.1 mmol). The mixture was stirred for 2 h then evaporated. Ether (5 mL) was added to the residue, and the precipitated solid was filtered off, washed with ether and dried to give Compound 162, 9 mg (95%) as a dark red solid. Compound 162 reacts quickly with n-BuNH2 in pre-column derivatization for HPLC analysis.

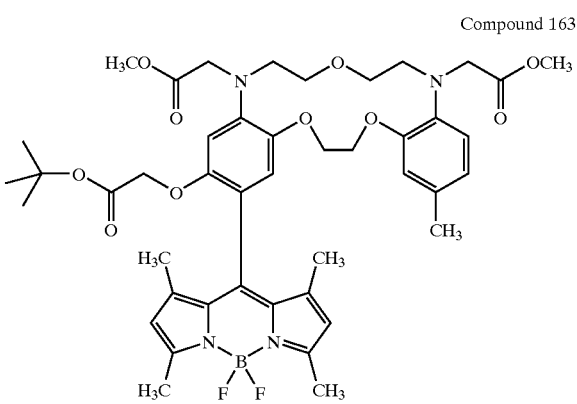

Compound 163

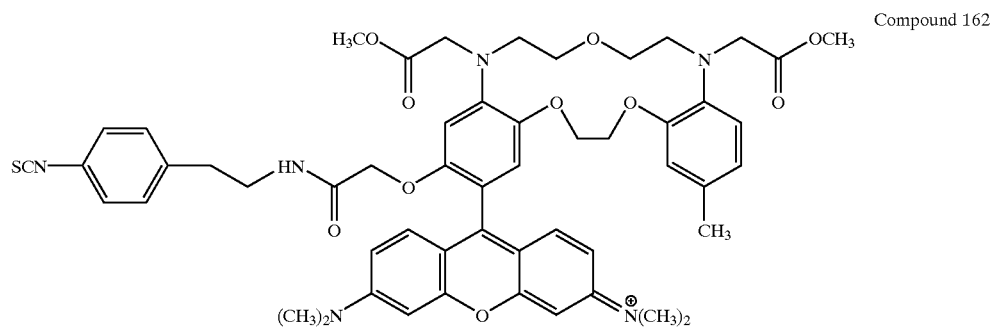

Compound 162

Example 43

Preparation of 4-(t-butoxycarbonylmethyloxy)-1,18-bis(methoxycarbonylmethyl)-14-methyl-5-[4,4-difluoro-1,3,5,7-tetramethyl-4-bora-3a,4a-diaza-s-indacen-8-yl]-DDTCPD (163).

To a stirred solution of aldehyde 119 (630 mg, 1.0 mmol) in $CH_2Cl_2$ (40 mL), 2,4-dimethylpyrrole (0.25 mL, 2.4 mmol) was added. The solution was stirred for 5 min, then TFA (0.1 mL, 1.2 mmol) was introduced. The mixture was stirred for 16 h, and diluted with $CHCl_3$ (300 mL). The chloroform solution was washed with 2% tetrabutylammonium hydroxide then $H_2O$, evaporated, and subsequently co-evaporated with toluene. The residue was dissolved in toluene (40 mL), stirred for 2 h with chloranil (296 mg, 1.2 mmol), then DIPEA (1.74 mL, 10 mmol) was introduced, followed by $BF_3$ etherate (1.04 mL, 8 mmol). The mixture was evaporated and the residue was purified by chromatography on $SiO_2$ using a gradient of 0–1% MeOH in $CHCl_3$ to give Compound 163, 280 mg (35%) as a brown solid.

Example 44

Preparation of 4-(t-butoxycarbonylmethoxy)-1,18-bis(methoxycarbonylmethyl)-14-methyl-5-[4,4-difluoro-1,3,5,7-tetramethyl-4-bora-3a,4a-diazа-s-indacen-8-yl]-DDTCPD (164).

A mixture of Compound 163 (120 mg, 0.15 mmol) in $CHCl_3$ (6 mL) and TFA (0.4 mL) was stirred for 16 h, then evaporated and co-evaporated with $CHCl_3$. The residue was purified by preparative TLC on two $SiO_2$ plates using 10% MeOH in $CHCl_3$ as eluant to give Compound 164, 82 mg (77%) as a brown solid.

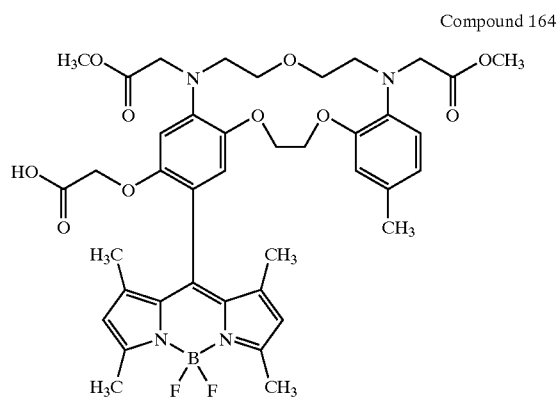

Compound 164

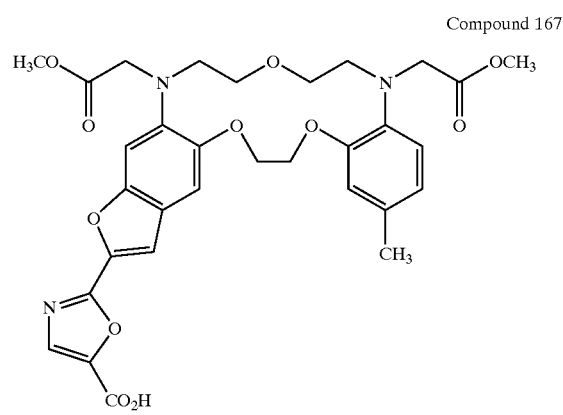

Compound 167

Example 45
Preparation of 4-acetoxymethoxycarbonylmethyloxy-1,18-bis(methoxycarbonylmethyl)-14-methyl-5-[4,4-difluoro-1,3,5,7-tetramethyl-4-bora-3a,4a-diaza-s-indacen-8-yl]-DDTCPD (165).

A mixture of Compound 164 (80 mg, 0.11 mmol), bromomethyl acetate (0.05 mL, 0.5 mmol), and DIPEA (0.17 mL, 1.0 mmol) in DMF (2 mL) was stirred for 2 h, poured into H₂O (150 mL), and extracted with CHCl₃. The extract was dried over MgSO₄ then evaporated. The residue was purified by preparative TLC on two SiO₂ plates using 3% MeOH and 0.5% AcOH in CHCl₃ to give Compound 165, 46 mg (52%) as a brown solid.

Example 47
Preparation of Compound 168.

A mixture of Compound 167 (62 mg, 0.1 mmol), bromomethyl acetate (0.05 mL, 0.5 mmol), and DIPEA (0.17 mL, 1.0 mmol) in DMF (1 mL) was stirred for 2 h, poured into 1% AcOH (100 mL), and extracted with CHCl₃. Then 3 M NaOAc (100 mL) was added to the aqueous phase and the mixture was extracted with more CHCl₃. The combined extracts were dried over MgSO₄ then evaporated. The residue was purified by preparative TLC on two SiO₂ plates using 5% MeOH in CHCl₃ to give Compound 168, 29 mg (42%) as an orange solid.

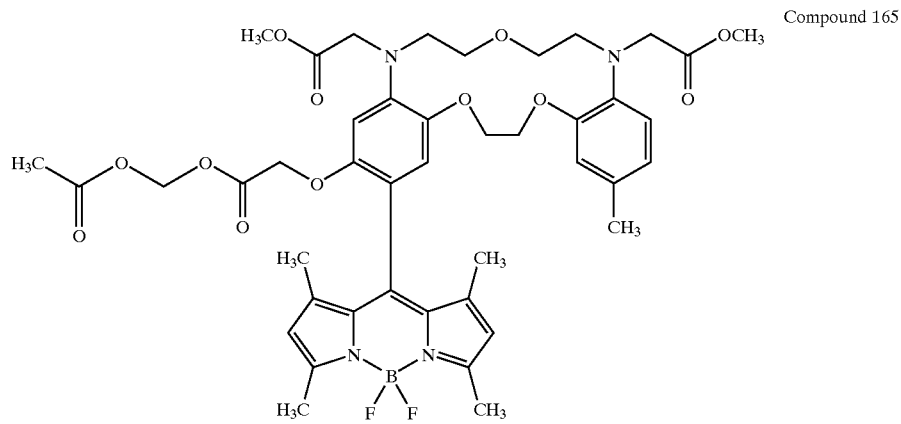

Compound 165

Example 46

Preparation of Compound 167.

A mixture of aldehyde 118 (800 mg, 1.55 mmol), 5-carboxy-2-chloromethyloxazole (300 mg, 1.86 mmol), K₂CO₃ (1.07 g, 7.75 mmol), and NaI (75 mg, 0.5 mmol; catalyst) in DMF (20 mL) was stirred at 135° C. for 4 h, then poured into H₂O. The mixture was acidified with 1 M HCl to pH 3, extracted with CHCl₃, dried over MgSO₄ then evaporated. The residue was purified by chromatography on SiO₂ using a gradient of 5–20% MeOH and 1–2% AcOH in CHCl₃ as eluant to give Compound 167, 255 mg (26%) as a yellowish solid.

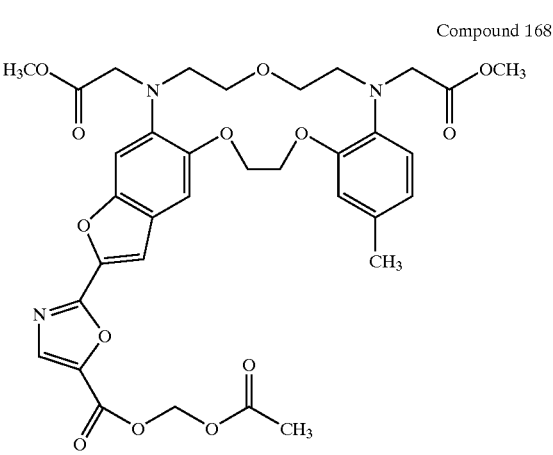

Compound 168

Example 48

Preparation of Compound 170.

A mixture of aldehyde 118 (1.40 g, 2.71 mmol), 2-chloromethyl-5-ethoxycarbonyloxazole (0.564 g, 1.86 mmol), $K_2CO_3$ (1.87 g, 13.60 mmol), and NaI (0.150 g, 1.00 mmol; catalyst) in DMF (30 mL) was stirred at 135° C. for 4 h, then poured into $H_2O$. The mixture was acidified with 1 M HCl to pH 3, extracted with $CHCl_3$ and evaporated. The residue was purified by chromatography on $SiO_2$ using 1% MeOH in $CHCl_3$ as eluant to give Compound 170, 1.260 g (71%) as a yellowish solid.

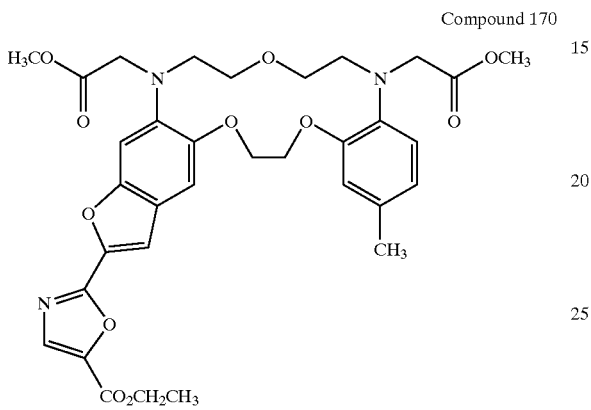

Compound 170

Example 49

Preparation of Compound 171.

A mixture of Compound 170 (376 mg, 0.5 mmol) and 1 M KOH (3 mL, 3.0 mmol) in MeOH (5 mL) was stirred for 5 h, then evaporated to 1/5 volume, and acidified with 1 M HCl to pH 2.8. The precipitated solid was filtered, washed with $H_2O$ and dried on a filter. This crude product was suspended in $H_2O$ (2 mL), then made basic with 0.1 M KOH to pH 9.5. The solution was loaded onto a SEPHADEX LH-20 resin column and chromatographed using $H_2O$ as eluant to give Compound 171, 256 mg (72%) as a yellow-greenish solid.

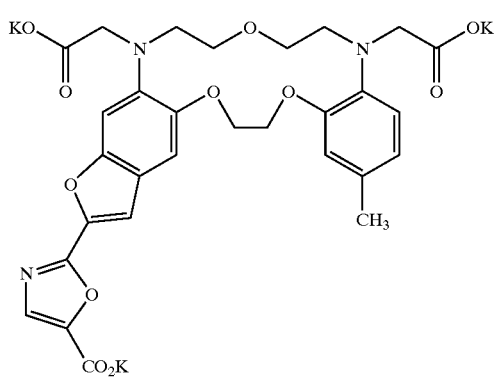

Compound 171

Example 50

Preparation of Compound 172.

A mixture of Compound 171 (71 mg, 0.1 mmol), bromomethyl acetate (0.1 mL, 1.0 mmol), and DIPEA (0.35 mL, 2.0 mmol) in DMF (2 mL) was stirred for 4 h, diluted with $CHCl_3$, then washed with 1% AcOH then $H_2O$ and evaporated. The residue was purified by preparative TLC on two $SiO_2$ plates using 5% MeOH and 0.5% AcOH in $CHCl_3$ to give compound 172, 63 mg (77%) as an orange solid.

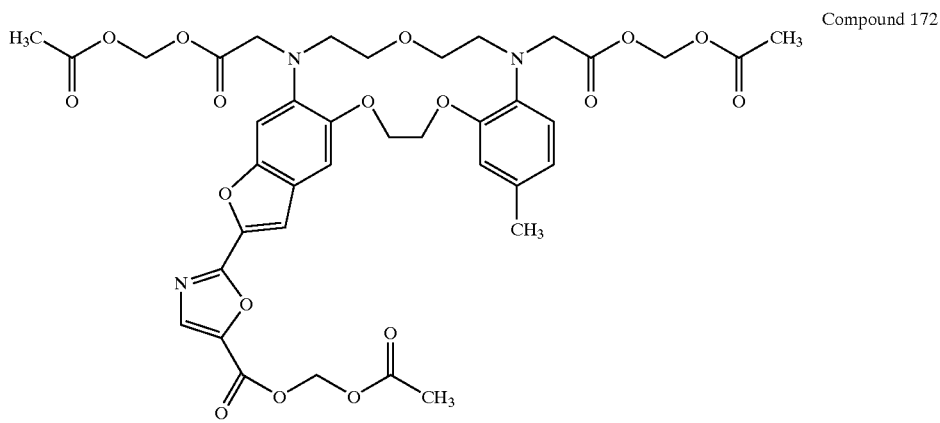

Compound 172

Example 51

Preparation of Trans 1-[4'-t-butoxycarbonylmethyloxy-1', 18'-bis-(methoxycarbonylmethyl)-14'-methyl-DDTCPD-5-yl]-2-[4"-methoxycarbonyl-2"-nitrophenyl] ethylene (173).

A mixture of aldehyde 119 (315 mg, 0.5 mmol), the Wittig base (4-methoxycarbonyl-2-nitrobenzyl)triphenylphosphonium bromide (375 mg, 0.7 mmol), and $K_2CO_3$ (345 mg, 2.5 mmol) in DMF (3 mL) was stirred for 6 h at 95° C. then cooled to room temperature and poured into $H_2O$. The solution was acidified to pH 5 with 1 M HCl and extracted with $CHCl_3$. The extract was dried over $MgSO_4$ and evaporated. The crude product was purified by chromatography on $SiO_2$ using $CHCl_3$, then 0.5% MeOH in $CHCl_3$ to give Compound 173, 339 mg (84%) as an orange solid.

Compound 173

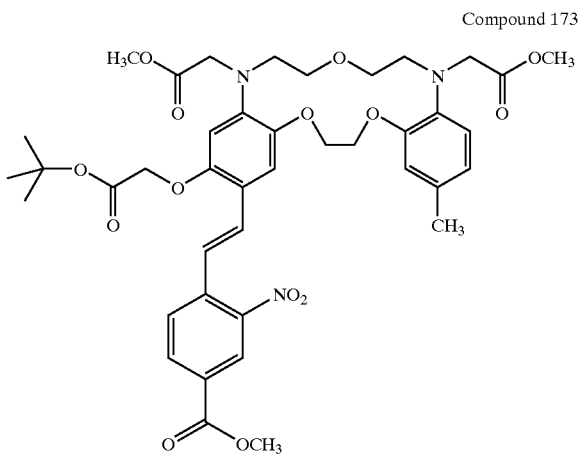

Example 52

Preparation of 4-t-butoxycarbonylmethyloxy 1,18-bis-(methoxycarbonylmethyl)-5-(6'-methoxycarbonylindolyl-2')-14-methyl-DDTCPD (174).

A mixture of the ethylene derivative 173 (338 mg, 0.42 mmol) and triethylphosphite (8 mL) was heated at 130° C. for 7 h, then evaporated and subsequently co-evaporated with DMF. The residue was first purified by chromatography on $SiO_2$ using $CHCl_3$ followed by 1% MeOH in $CHCl_3$, then by preparative TLC on two $SiO_2$ plates using 50% EtOAc in hexanes as eluant to give Compound 174, 112 mg (34%) as a slightly yellowish solid.

Compound 174

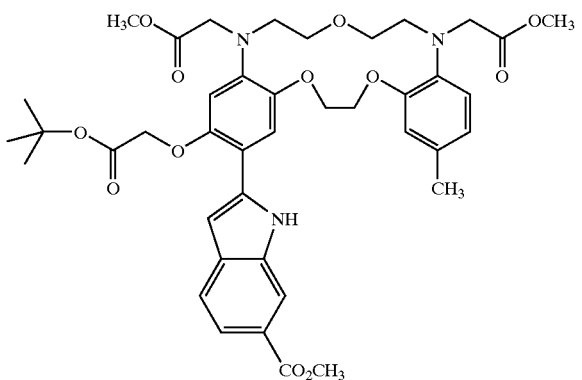

Example 53

Preparation of 4-carboxymethyloxy 1,18-bis-(methoxycarbonylmethyl)-5-(6'-methoxycarbonylindolyl-2')-14-methyl-DDTCPD (175).

A mixture of Compound 174 (104 mg, 0.13 mmol) in $CH_2Cl_2$ (2 mL) and TFA (2 mL) was stirred for 3 h, then evaporated and co-evaporated with $CHCl_3$. The residue was purified by preparative TLC on two $SiO_2$ plates using 7% MeOH and 2% AcOH in $CHCl_3$ to give Compound 175, 55 mg (57%) as a yellowish solid.

Compound 175

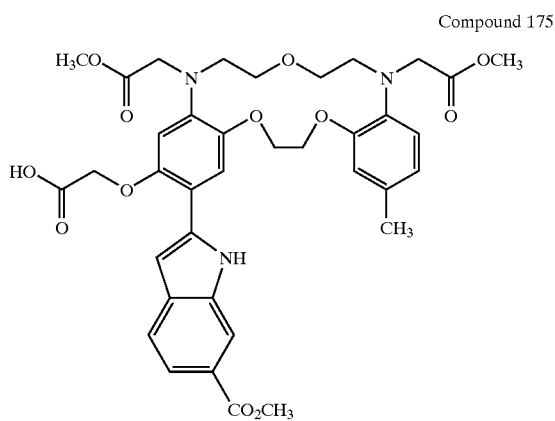

Example 54

Preparation of 4-acetoxymethylcarbonylmethyloxy 1,18-bis-(methoxycarbonylmethyl)-5-(6'-methoxycarbonylindolyl-2')-14-methyl-DDTCPD (176).

A mixture of Compound 175 (22 mg, 0.03 mmol), bromomethyl acetate (0.1 mL, 1.0 mmol), and DIPEA (0.26 mL, 1.5 mmol) in DMF (2 mL) was stirred for 16 h, then diluted with $CHCl_3$ (100 mL), washed with 1% AcOH then $H_2O$ then evaporated. The residue was purified by preparative TLC on two $SiO_2$ plates using 5% MeOH in $CHCl_3$ to give compound 176, 16 mg (67%) as an orange solid.

Compound 176

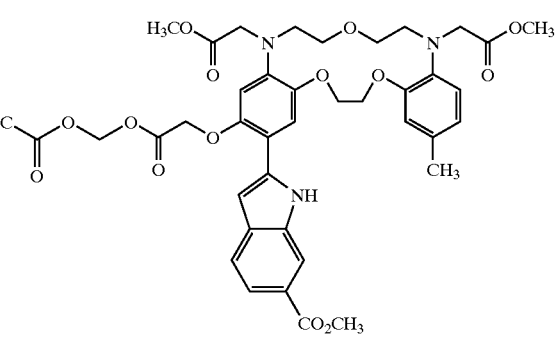

Example 55

Preparation of 4-carboxymethyloxy-1,18-bis(carboxymethyl)-14-methyl-5-[TMR]-DDTCPD (177).

A mixture of Compound 152 (87 mg, 0.1 mmol) and 1M KOH (2 mL, 2 mmol) in MeOH (5 mL) was stirred for 16 h, and evaporated. The residue was purified on SEPHADEX LH-20 resin using $H_2O$ as the eluant. The fractions containing product were collected and lyophilized to give Compound 177, 12 mg (14%) as a crimson solid.

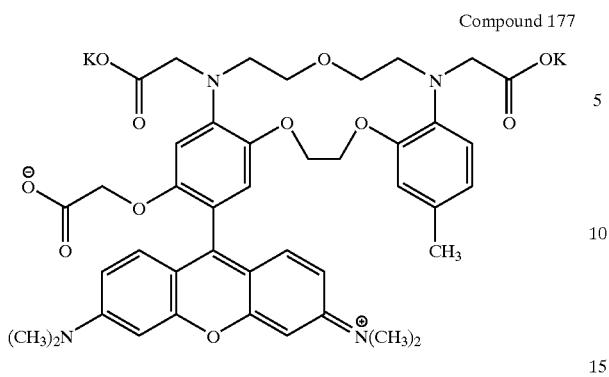

Compound 177

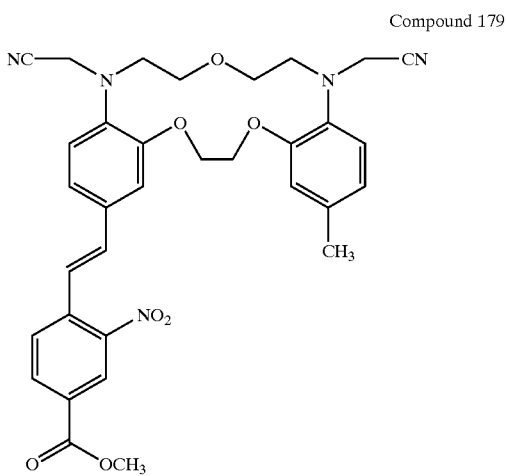

Compound 179

Example 56
Preparation of 4-acetoxymethoxycarbonylmethyloxy-1,18-bis(acetoxymethoxycarbonylmethyl)-14-methyl-5-[TMR]-DDTCPD (178).

A mixture of Compound 177 (8 mg, 0.01 mmol), bromomethyl acetate (0.025 mL, 0.25 mmol), and DIPEA (0.08 mL, 0.5 mmol) in DMF (1 mL) was stirred for 16 h, and diluted with CHCl₃ (100 mL). The solution was washed with 1% AcOH then H₂O then evaporated. Ether (5 mL) was added to the residue. The precipitated solid was filtered off and washed with ether to give Compound 178, 5 mg (50%) as a dark red solid. Compound 178 was pure on TLC and HPLC.

Example 58
Preparation of 1,18-bis(cyanomethyl)-5-(6'-methoxycarbonylindolyl-2')-14-methyl-DDTCPD (180).

A mixture of the ethylene derivative 179 (170 mg, 0.28 mmol) and triethylphosphite (4 mL) was heated at 120° C. for 16 h, then evaporated and subsequently co-evaporated with DMF. The residue was purified by preparative TLC on two SiO₂ plates using 3% MeOH in CHCl₃ as eluant, then on two SiO₂ plates using 40% EtOAc in hexanes as eluant to give Compound 180, 26 mg (16%) as a yellowish solid.

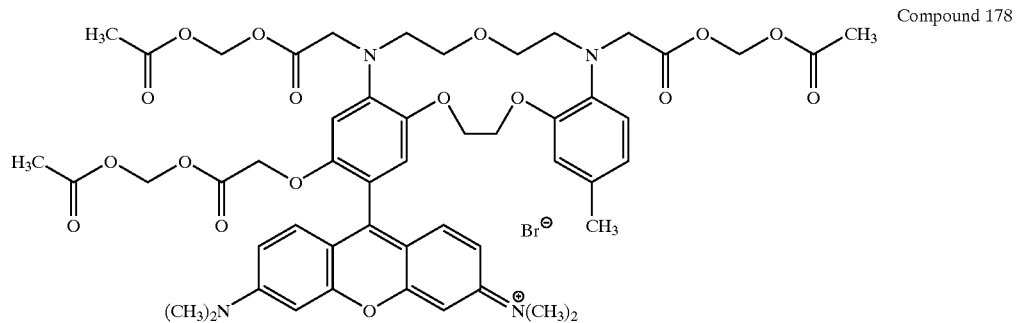

Compound 178

Example 57

Preparation of trans 1-[1',18'-bis-(cyanomethyl)-14'-methyl-DDTCPD-5-yl]-2-[4"-methoxycarbonyl-2"-nitrophenyl]ethylene (179).

A mixture of aldehyde 121 (217 mg, 0.5 mmol), the Wittig base (4-methoxycarbonyl-2-nitrobenzyl)triphenylphosphonium bromide (536 mg, 0.7 mmol), and K₂CO₃ (345 mg, 2.5 mmol) in DMF (3 mL) was stirred for 16 h at 95° C., then cooled to room temperature and poured into H₂O. The solution was acidified with 1 M HCl to pH 3, extracted with CHCl₃, dried over MgSO₄ and evaporated. The crude product was purified by chromatography on SiO₂ using CHCl₃ as eluant to give Compound 179, 171 mg (56%) as an orange solid.

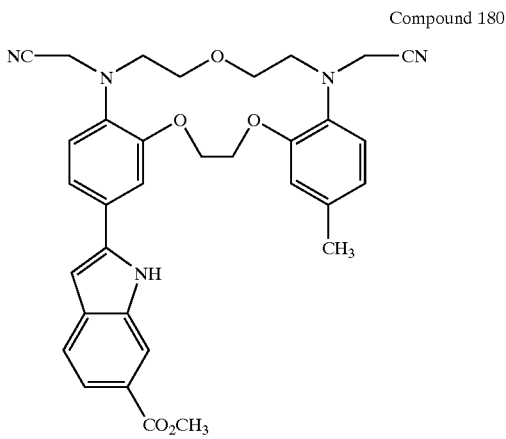

Compound 180

Example 59
Preparation of 1,18-bis(carbamoylmethyl)-14-methyl-5-[dihydrotetramethylrhodamine]-DDTCPD (181).

A mixture of aldehyde 123 (100 mg, 0.21 mmol), 3-dimethylaminophenol (55 mg, 0.40 mmol), and p-toluenesulphonic acid (5 mg, catalyst) in propionic acid (2 mL) was stirred overnight at 60° C., then cooled to room temperature and poured into 3 M NaOAc (40 mL). Precipitated solid was filtered, washed with $H_2O$ and dried to give Compound 181, 140 mg (93%) as a rose-colored solid. Compound 181 was unstable to oxidation and was used in next step without additional purification.

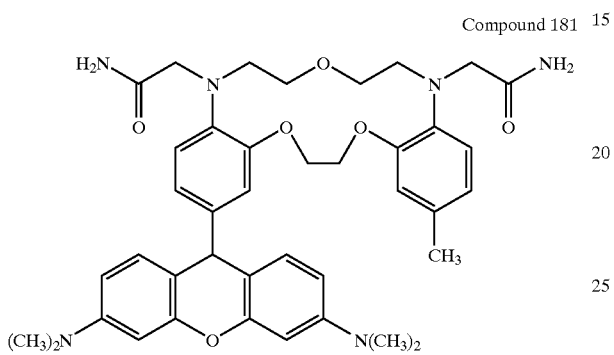

Compound 181

Example 60
Preparation of 1,18-bis(carbamoylmethyl)-14-methyl-5-[tetramethylrhodamine]-DDTCPD (182).

A mixture of Compound 181 (138 mg, 0.20 mmol) and chloranil (84 mg, 0.34 mmol) in MeOH (5 mL) and $CHCl_3$ (5 mL) was stirred for 4 h, and evaporated. The residue was purified by chromatography on $SiO_2$ using a gradient of 7–9% MeOH and 0.5–1% AcOH in $CHCl_3$ as eluant to give Compound 182, 118 mg (86%) as a dark red solid.

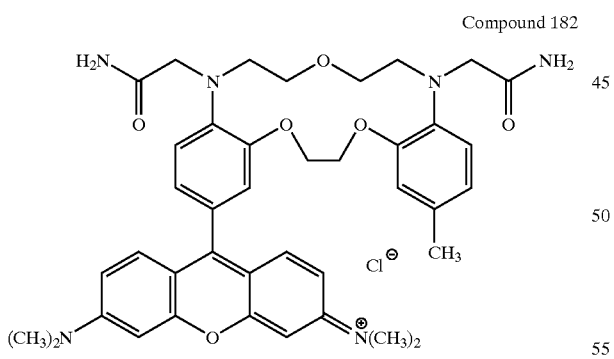

Compound 182

Example 61
Preparation of Compound 200.

To a 0.5 M solution of arene 108 in sulfuric acid is added one equivalent of potassium nitrate. The resulting solution is stirred until TLC analysis of reaction aliquots, treated with water and ether, shows full conversion to nitroarene 200. The reaction mixture is poured into excess aqueous sodium acetate, followed by extraction with ether. The extract is washed with aqueous sodium bicarbonate and brine, dried over magnesium sulfate, then concentrated to a reddish-brown oil, which is purified by trituration with ether-hexanes to give Compound 200 as a yellow powder.

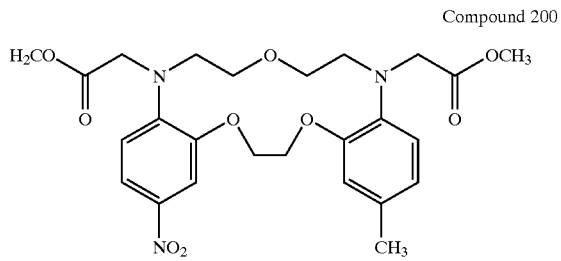

Compound 200

Example 62
Preparation of Compound 201.

A 0.5 M solution of Compound 200 in methanol is treated with 10% palladium on charcaol, at 10 wt % of Compound 200. The resulting mixture is shaken under 40 psi hydrogen until TLC analysis shows full conversion to aniline 201. The reaction mixture is filtered through diatomaceous earth, followed by concentration in vacuo. The residue is triturated with ether-hexanes to give pure Compound 201 as an off-white powder.

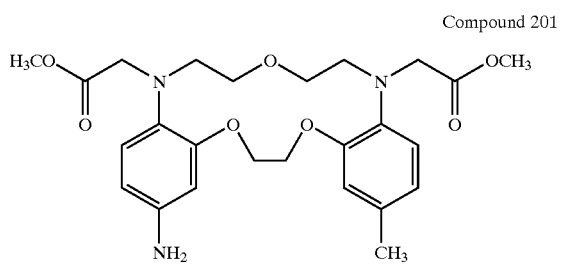

Compound 201

Example 63
Preparation of Compound 203.

A mixed anhydride of 6-carboxytetramethylrhodamine is prepared according to the procedure given in U.S. Pat. No. 5,453,517 to Kuhn et al. To a solution of the mixed anhydride and one equivalent of diisopropylethylamine in anhydrous THF under nitrogen is added slowly a 0.3 M solution of Compound 201. The resulting mixture is stirred until TLC analysis indicates consumption of Compound 201. The reaction mixture is concentrated in vacuo, and the residue partitioned between chloroform and water. The chloroform layer is washed with brine and dried over magnesium sulfate, then concentrated in vacuo. The residue is purified by flash chromatography on silica gel using increasing amounts of methanol in chloroform as eluant to give pure Compound 203 as a red powder.

Compound 203

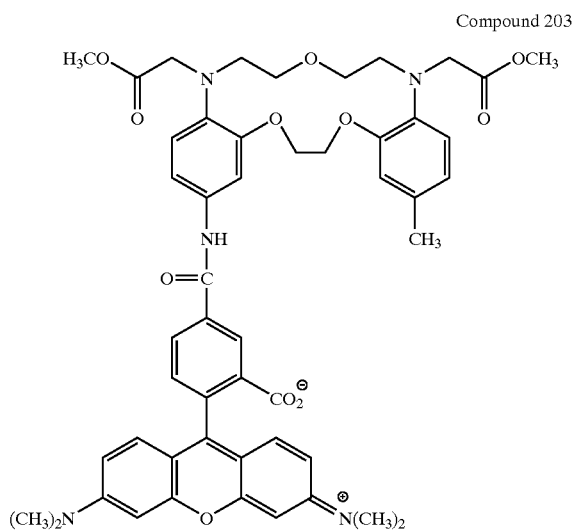

Example 64

Preparation of a tris-aza crown ether (205).

To a dilute solution (0.1 M) of diamine 105 and two equivalents of DIPEA in anhydrous THF is slowly added at room temperature a dilute solution (0.1 M) of N,N-bis(chlorocarbonylmethyl)-aniline. After stirring overnight, the volatiles are removed by evaporation, and the residue is partitioned between 5% hydrochloric acid and ethyl acetate. The organic layer is washed with brine, dried, and concentrated. The resulting residue is purified by column chromatography on silica gel using increasing amounts of methanol in chloroform to give pure Compound 205.

Compound 205

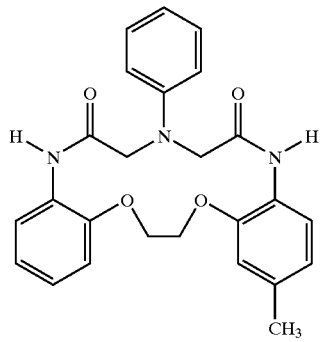

Example 65

Preparation of Compound 206.

The bisamide 205 is reduced to bisaniline 206 as described for Compound 107.

Compound 206

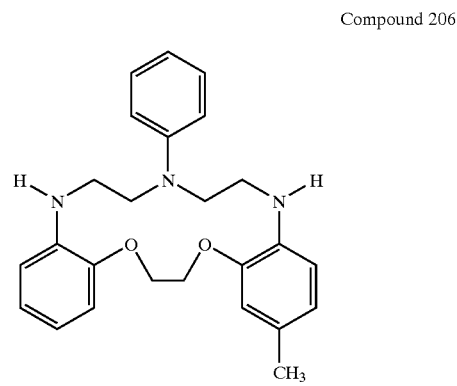

Example 66
Preparation of Compound 207.
The bisaniline 206 is alkylated to give Compound 207, as described for Compound 108.

Compound 207

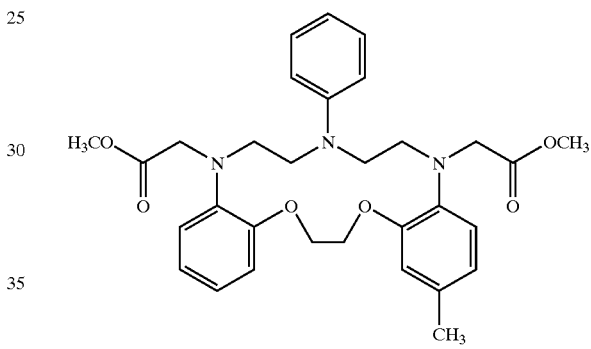

Example 67
Preparation of Compound 208.
The bisester 207 is formylated to give the aldehyde Compound 208, as described for Compound 109.

Compound 208

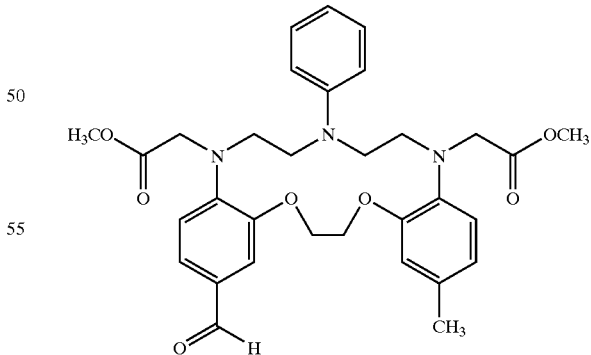

Example 68
Preparation of Compound 209.
The aldehyde 208 is condensed with two equivalent of 3-(dimethylamino)phenol as described for Compound 137 to give Compound 209.

Compound 209

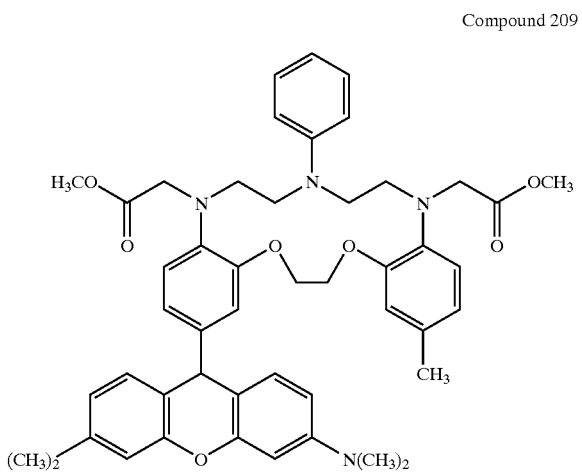

Example 69

Preparation of Compound 210.

Compound 209 is oxidized with chloranil to give the chloride salt 210 as a red powder, as described for Compound 138.

Compound 210

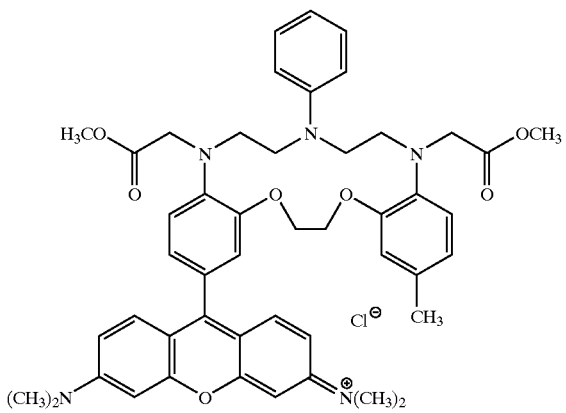

Example 70

Preparation of a thia-substituted crown ether (211).

A bis-aza crown ether that incorporates a sulfur atom in the crown is prepared using the procedures of Examples 64–69, except that in place of N,N-bis(chlorocarbonylmethyl)-aniline, the bis-acid chloride of thiodiglycolic acid is used (Cl(C=O)CH$_2$—S—CH$_2$(C=O)Cl). After preparation of the crown ether itself, condensation with 3-(N,N-dimethylamino)phenol, and oxidation, the chloride salt of the thia-crown ether, Compound 211, is isolated as a red powder.

Compound 211

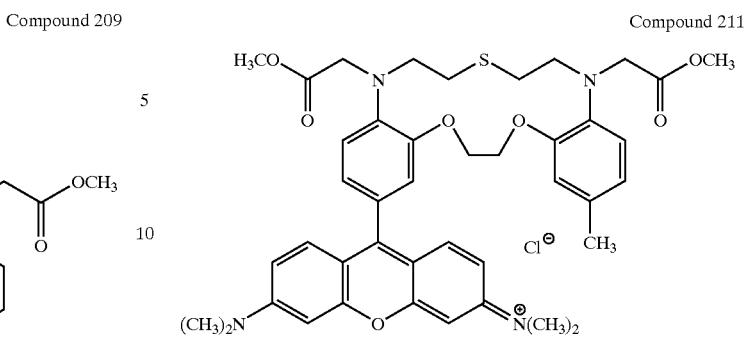

Example 71

Determination of Sodium Indicator Fluorescence Response.

The fluorescence response of a selected compound of the invention as a function of sodium ion concentration was determined by dissolving a sample of the pure compound in 3 mL of each of two solutions: solution 1 ("high Na$^+$") consists of 200 mM NaCl and 10 mM MOPS buffer at pH 7.05; solution 2 ("zero Na$^+$") consists of 10 mM MOPS buffer at pH 7.05 in deionized water. A series of curves are generated by cross dilution between the two solutions to arrive at intermediate concentrations of Na$^+$. The emission of a selected indicator in solution 2 was scanned and then was repeated to cover the entire range from zero to 200 mM Na$^+$. For example, the fluorescence emission of the chosen indicator was scanned while the sample was excited at that indicator's absorption maximum wavelength, and then $1/100$ of the sample was removed and replaced with $1/100$ of solution 1 to arrive at a Na$^+$ concentration of 2 mM. This dilution was repeated to cover the entire range from zero to 1 M Na$^+$ and the resulting emission intensities were plotted versus the ion concentrations. A least-squares fit was used to arrive at the concentration where the selected indicator was maximally sensitive to changes in Na$^+$ concentration. This corresponded to the dissociation constant of that indicator for Na$^+$ and was expressed as a concentration.

For visible wavelength probes such as Compound 132 (Example 17) and Compound 138 (Example 22) the indicator's fluorescence emission was typically scanned from 450–650 nm while the sample was excited at the absorption maximum wavelength. For UV-excitable ratiometric probes such as Compound 167 (Example 46), the excitation wavelengths of the dye in solution 2 were scanned from 260 to 450 nm while monitoring constant fluorescence emission at 510 nm (as in FIG. 1).

The binding affinity of a selected indicator for sodium ions, in the presence of potassium ions, is determined using the process above, except in the presence of 100 mM K$^+$ concentrations.

Example 72

Calibration of Sodium Indicator Fluorescence Response in Cells.

Figure 3:
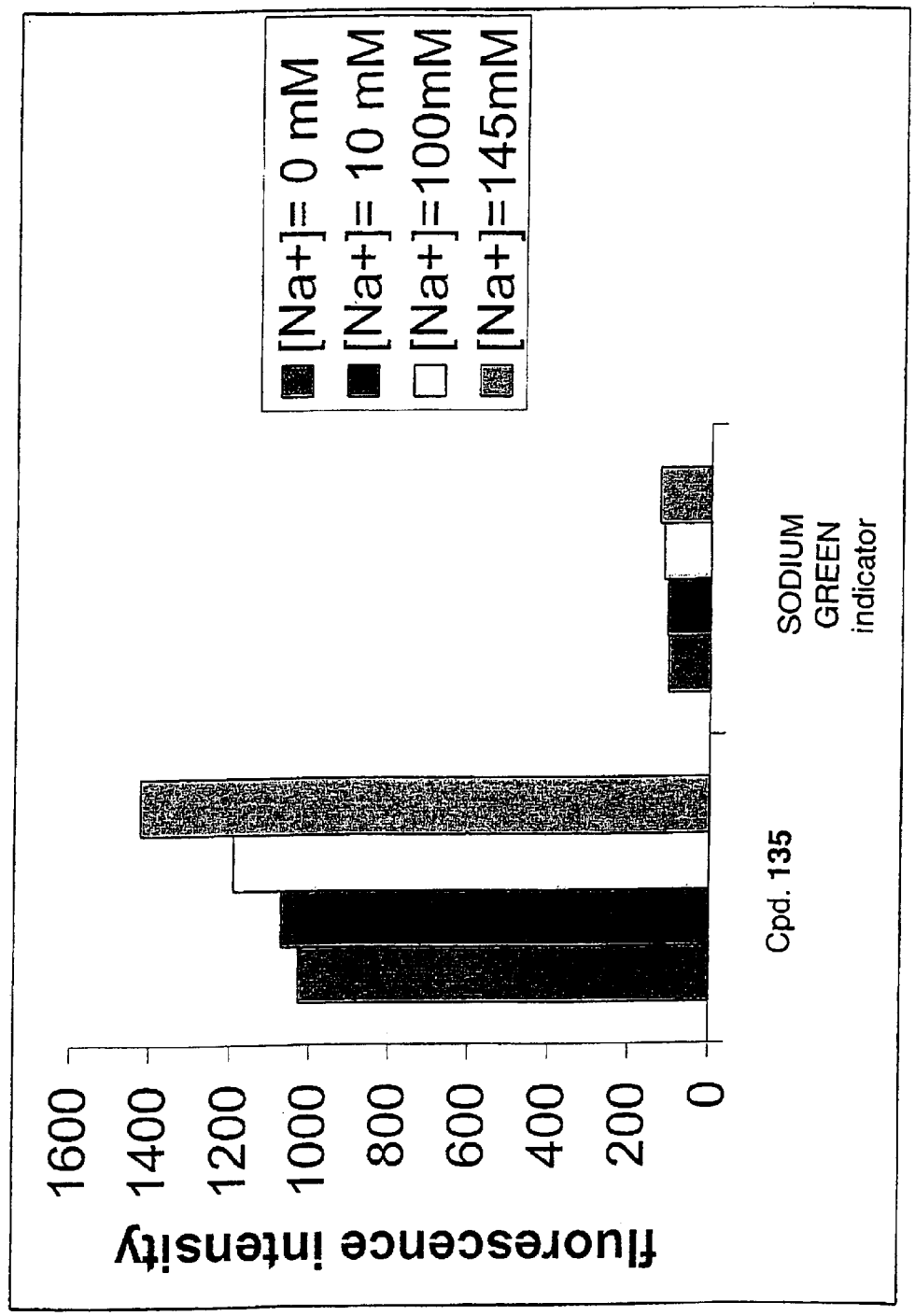
FIG. 3: A comparison of the intracellular sodium response of SODIUM GREEN tetraacetate indicator (Molecular Probes, Inc.) or Compound 134. At every intracellular $Na^+$ concentration, Compound 134 demonstrates a stronger fluorescence intensity than SODIUM GREEN sodium indicator at the same concentration (as described in Example 72).

Jurkat cells were loaded with a 5 μM solution of either Compound 135 (Example 20) or commercially available SODIUM GREEN tetraacetate indicator (Molecular Probes, Inc., Eugene, Oreg.) for 30 minutes at 37° C. The use of PLURONIC dispersing agent helped dissolve the selected indicator. Intracellular sodium concentrations were then established by varying the sodium concentration of the extracellular buffer in the presence of 2 μM gramicidin (a sodium-pore forming antibiotic). The extracellular buffer was set at 0 mM, 10 mM, 20 mM, 50 mM, 100 mM, and 145 mM, respectively. Intracellular fluorescence response of the selected indicators was measured using a FACSCAN flow cytometer and associated software, with fluorescence excitation at 488 nm. Compound 135 exhibits substantially brighter intracellular fluorescence intensity than the SODIUM GREEN indicator at comparable $Na^+$ concentrations, as shown in FIG. 3. Similarly, as intracellular $Na^+$ concentration was increased, Compound 135 exhibits a consistent increase in fluorescence intensity.

Example 73
Preparation of a Biotinylated Indicator, Compound 212.

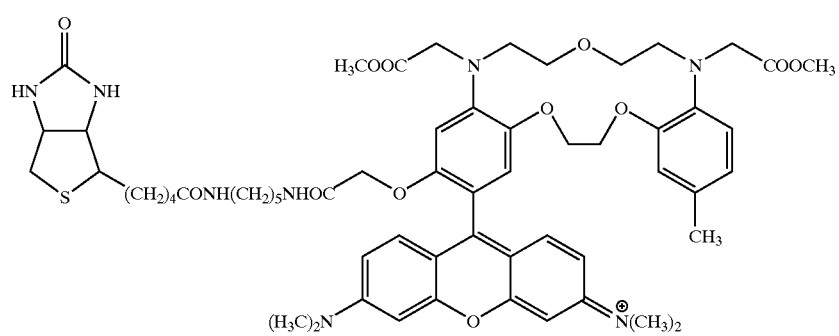

Compound 212

To a stirred solution of succinimidyl ester 155 prepared as in Example 36 from compound 153 (81 mg, 0.1 mmol) in DMF (2 mL) was added $Et_3N$ (0.27 mL, 2 mmol) followed by biotin-cadaverin trifluoracetate (66 mg, 02 mmol). The mixture was stirred for 16 h, diluted with $CHCl_3$ (100 mL), washed 1% AcOH (3×50 mL), $H_2O$ (100 mL) dried over $MgSO_4$ and evaporated. The residue was purified by preparative TLC on four C18 reverse-phase plates using 50% aqueous 2-PrOH with 0.2% TFA as eluant to give Compound 212, 25 mg (22%) as an orange solid.

Example 74
Avidin-labeling with a Biotinylated Fluorescent Crown Ether.

A 5 mg/mL solution of streptavidin in phosphate-buffered saline (PBS, pH 7.0) is treated with a 1 mg/mL solution of biotinylated indicator (e.g., Compound 212, Example 73) in 2% DMSO/PBS at a molar ratio such that two equivalents of biotinylated indicator are present for every streptavidin molecule. The resulting solution is incubated at 37° C. for 4 hours, then centrifuged. The supernatant is applied to a Sephadex G-25 gel filtration column (2 mL bed volume/mg protein) and eluted with PBS. The streptavidin-indicator complex elutes first. Fractions are analyzed by TLC to ensure that no free indicator is present in the complex. Pure product fractions are pooled and lyophilized. The complex is useful as a bridging method to apply the indicator to any biotinylated surface or substance.

All publications, patents and patent applications referred to within this document are incorporated by reference to the same extent as if each individual publication, patent or patent application was specifically and individually indicated to be incorporated by reference.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

What is claimed is:

1. A compound having the formula:

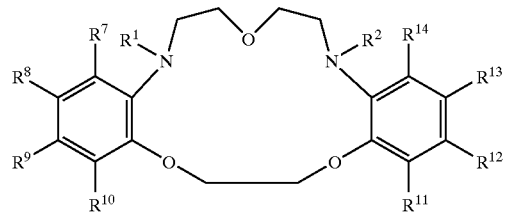

wherein $R^1$ is $-L-R_X$, $-L-S_C$, -L-DYE; $C_7-C_{18}$ alkyl or $C_1-C_{18}$ arylalkyl, each of which is optionally substituted by halogen, azido, nitro, nitroso, amino, hydroxy, cyano, or by an aryl or heteroaryl ring system; or by $-(SO_2)-R^{15}$, $-(SO_2)-O-R^{15}$, $-(C=O)-R^{15}$, $-(C=O)-O-R^{16}$, $-(C=O)-NR^{17}R^{18}$; or by $C_1-C_8$ alkylamino, $C_2-C_{12}$ dialkylamino; or by $C_1-C_6$ alkyl or $C_1-C_6$ alkoxy, each of which is itself optionally substituted by halogen, amino, hydroxy, $-(SO_2)-R^{15}$, $-(SO_2)-O-R^{15}$, $-(C=O)-R^{15}$, $-(C=O)-O-R^{16}$, $-(C=O)-NR^{17}R^{18}$;

$R^2$ is $-L-R_X$, $-L-S_C$, -L-DYE; $C_1-C_{18}$ alkyl or $C_7-C_{18}$ arylalkyl, each of which is optionally substituted by halogen, azido, nitro, nitroso, amino, hydroxy, cyano, or by an aryl or heteroaryl ring system; or by $-(SO_2)-R^{15}$, $-(SO_2)-O-R^{15}$, $-(C=O)-R^{15}$, $-(C=O)-O-R^{16}$, $-(C=O)-NR^{17}R^{18}$; or by $C_1-C_6$ alkylamino, $C_2-C_{12}$ dialkylamino; or by $C_1-C_8$ alkyl or $C_1-C_6$ alkoxy, each of which is itself optionally substituted by halogen, amino, hydroxy, $-(SO_2)-R^{15}$, $-(SO_2)-O-R^{15}$, $-(C=O)-R^{15}$, $-(C=O)-O-R^{16}$, $-(C=O)-NR^{17}R^{18}$;

wherein $R^{15}$ is H, $C_1-C_6$ alkyl, $-L-R_X$, $-L-S_C$, or -L-DYE;

$R^{16}$ is H, a $C_1-C_6$ alkyl, a benzyl, alpha-acyloxyalkyl, t-butyldimethylsilyl, a biologically compatible salt, $-L-R_X$, $-L-S_C$, or -L-DYE;

$R^{17}$ is H, $C_1$–$C_6$ alkyl, $C_1$–$C_8$ carboxyalkyl, an alpha-acyloxyalkyl, a t-butyldimethylsilyl, a biologically compatible salt, -L-$R_X$, -L-$S_C$, or -L-DYE;

$R^{18}$ is H, $C_1$–$C_6$ alkyl, $C_1$–$C_8$ carboxyalkyl, an alpha-acyloxyalkyl, a t-butyldimethylsilyl, a biologically compatible salt, -L-$R_X$, -L-$S_C$, or -L-DYE;

or $R^{17}$ and $R^{18}$ taken in combination form a 5- or 6-membered aliphatic ring that optionally incorporates an oxygen atom;

L is a covalent linkage;

Rx is an acrylamide, an activated ester of a carboxylic acid, an acyl azide, an acyl nitrile, an aldehyde, an alkyl halide, an anhydride, an aniline, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, or a thiol;

Sc is an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a biotin, a silica or a virus;

DYE is a chemical moiety with an absorption maximum of beyond 320 nm;

$R^7$ is H, halogen, azido, nitro, nitroso, amino, cyano, -L-$R_X$, -L-$S_C$, -L-DYE, $C_1$–$C_8$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^8$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^9$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^{10}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^{11}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^{12}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^{13}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^{14}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, or —(C=O)—$R^{15}$, —(C=O)—O—$R^{16}$, —(C=O)—$NR^{17}R^{18}$;

or any two adjacent substituents $R^7$–$R^{14}$, taken in combination, form a fused six-membered benzo moiety, which is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is optionally substituted by halogen, amino, hydroxy, —(C=O)—$R^{15}$, —(=O)—O—$R^{16}$, or —(C=O)—$NR^{17}R^{18}$;

or any two adjacent substituents $R^7$–$R^{14}$, taken in combination with each other, and with the aromatic ring they are bound to, form a fused DYE;

provided that the compound is substituted by at least one -L-DYE, -L-$R_X$, or -L-$S_C$ at $R^1$, $R^2$, $R^4$, $R^7$, $R^8$, $R^9$, $R^{10}$, $R^{11}$, $R^{12}$, $R^{13}$, or $R^{14}$; or at least two of $R^7$–$R^{14}$, taken in combination, form a fused DYE.

2. The compound according to claim 1, wherein the compound is substituted by only one -L-$R_X$, or -L-$S_C$, that is bound at $R^8$, $R^9$, $R^{12}$, or $R^{13}$.

3. The compound according to claim 1, wherein $R^1$ and $R^2$ are $C_1$–$C_6$ alkyl that are substituted one or more times by cyano, —(C=O)—O—$R^{15}$, or —(C=O)—$NR^{17}R^{18}$.

4. The compound according to claim 3, wherein $R^{15}$, $R^{17}$ and $R^{18}$ are independently H or $C_1$–$C_6$ alkyl.

5. The compound according to claim 1, wherein $R^8$ and $R^9$, and optionally $R^{12}$ and $R^{13}$, taken in combination, form a fused DYE that is a substituted or unsubstituted benzofuran.

6. The compound according to claim 1, wherein the compound is substituted by exactly two DYE or fused DYE moieties.

7. The compound according to claim 1, wherein the compound is substituted by exactly one -L-DYE moiety at $R^9$, and said compound is optionally substituted at a position other than $R^9$ by exactly one -L-$R_X$ or exactly one -L-$S_C$.

8. The compound according to claim 1, wherein L is independently a single covalent bond, or a covalent linkage that is linear or branched, cyclic or heterocyclic, saturated or unsaturated, having 1–20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

9. The compound according to claim 1, wherein L is a single covalent bond or has the formula —$(CH_2)_d$(CONH$(CH_2)_e)_z$— or —O$(CH_2)_d$(CONH$(CH_2)_e)_z$—, where d is an integer from 0–5, e is an integer from 1–5 and z is 0 or 1.

10. The compound according to claim 1, wherein the DYE moiety is selected from the group consisting of indole, a coumarin, a stilbene, a xanthene, an oxazine, and a polyazaindacene.

11. The compound according to claim 1, wherein the compound is substituted by exactly one $S_C$ that is a protein, a polysaccharide, a biotin, a synthetic polymer or a silica.

12. The compound according to claim 1, wherein the compound is substituted by at least one Rx selected from the group consisting of a succinimidyl ester of a carboxylic acid, a haloacetamide, a hydrazine, an isothiocyanate, a maleimide, an aliphatic amine, a silyl halide, and a psoralen.

13. A compound having the formula:

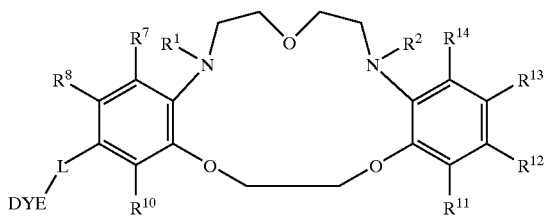

wherein $R^1$ is -L-$R_X$, -L-$S_C$, -L-DYE; $C_1$–$C_{18}$ alkyl or $C_7$–$C_{18}$ arylalkyl, each of which is optionally substituted by halogen, azido, nitro, nitroso, amino, hydroxy, cyano, or by an aryl or heteroaryl ring system; or by —($SO_2$)—$R^{15}$, —($SO_2$)—O—$R^{16}$, —(C=O)—$R^{15}$, —(C=O)—O—$R^{16}$, —(C=O)—$NR^{17}R^{18}$; or by $C_1$–$C_6$ alkylamino, $C_2$–$C_{12}$ dialkylamino; or by $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{16}$, —(C=O)—$R^{15}$, —(C=O)—O—$R^{16}$, —(C=O)—$NR^{17}R^{18}$;

$R^2$ is -L-$R_X$, -L-$S_C$, -L-DYE; $C_1$–$C_{18}$ alkyl or $C_7$–$C_{18}$ arylalkyl, each of which is optionally substituted by halogen, azido, nitro, nitroso, amino, hydroxy, cyano, or by an aryl or heteroaryl ring system; or by —($SO_2$)—$R^{15}$, —($SO_2$)—O—$R^{15}$, —(C=O)—$R^{15}$, —(C=O)—O—$R^{16}$, —(C=O)—$NR^{17}R^{18}$; or by $C_1$–$C_6$ alkylamino, $C_2$–$C_{12}$ dialkylamino; or by $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

wherein $R^{15}$ is H, $C_1$–$C_6$ alkyl, -L-$R_X$, -L-$S_C$, or -L-DYE;

$R^{16}$ is H, a $C_1$–$C_6$ alkyl, a benzyl, alpha-acyloxyalkyl, t-butyldimethylsilyl, a biologically compatible salt, -L-$R_X$, -L-$S_C$, or -L-DYE;

$R^{17}$ is H, $C_1$–$C_6$ alkyl, $C_1$–$C_8$ carboxyalkyl, an alpha-acyloxyalkyl, a t-butyldimethylsilyl, a biologically compatible salt, -L-$R_X$, -L-$S_C$, or -L-DYE;

$R^{18}$ is H, $C_1$–$C_6$ alkyl, $C_1$–$C_8$ carboxyalkyl, an alpha-acyloxyalkyl, a t-butyldimethylsilyl, a biologically compatible salt, -L-$R_X$, -L-$S_C$, or -L-DYE;

or $R^{17}$ and $R^{18}$ taken in combination form a 5- or 6-membered aliphatic ring that optionally incorporates an oxygen atom;

L is a covalent linkage;

Rx is selected from the group consisting of an acrylamide, an activated ester of a carboxylic acid, an acyl azide, an acyl nitrile, an aldehyde, an alkyl halide, an anhydride, an aniline, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, or a thiol;

Sc is selected from the group consisting of an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a biotin, a silica and a virus;

DYE is selected from the group consisting of indole, a coumarin, a stilbene, a xanthene, an oxazine, a polyazaindacene, a benzofuran, a pyrene, an anthracene, a naphthalene, an acridine, a benzindole, an oxazole, a benzoxazole, a thiazole, a benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a benzoxazine, a carbazine a phenalenone and a benzphenalenone;

$R^7$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^8$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{10}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^{11}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^{12}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, or —(C=O)—$R^{15}$, —(C=O)—O—$R^{16}$, —(C=O)—$NR^{17}R^{18}$;

$R^{13}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, or —(C=O)—$R^{15}$, —(C=O)—O—$R^{16}$, —(C=O)—$NR^{17}R^{18}$; and $R^{14}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$.

14. The compound according to claim 13, wherein DYE is an indole, a coumarin, a stilbene, a xanthene, an oxazine, or a polyazaindacene.

15. The compound according to claim 13, wherein the xanthene is selected from the group consisting of a fluorescein, a rhodamine, a rhodol, a 3H-xanthen-6-ol-3-one, a 6-amino-3H-xanthen-3-one, and a 6-amino-3H-xanthen-3-imine; wherein L is a single covalent bond.

16. The compound according to claim 13, wherein $R^1$ and $R^2$ are $C_1$–$C_6$ alkyl that are substituted one or more times by —(C=O)—O—$R^{16}$ or —(C=O)—$NR^{17}R^{18}$.

17. The compound according to claim 13, wherein $R^1$ and $R^2$ are $C_1$–$C_6$ alkyl that are substituted one or more times by —(C=O)—O—$R^{16}$, where each $R^{16}$ is H, $C_1$–$C_8$ alkyl, an alpha-acyloxymethyl, a t-butyldimethyldimethylsilyl, or a biologically compatible salt.

18. The compound according to claim 13, wherein the compound is

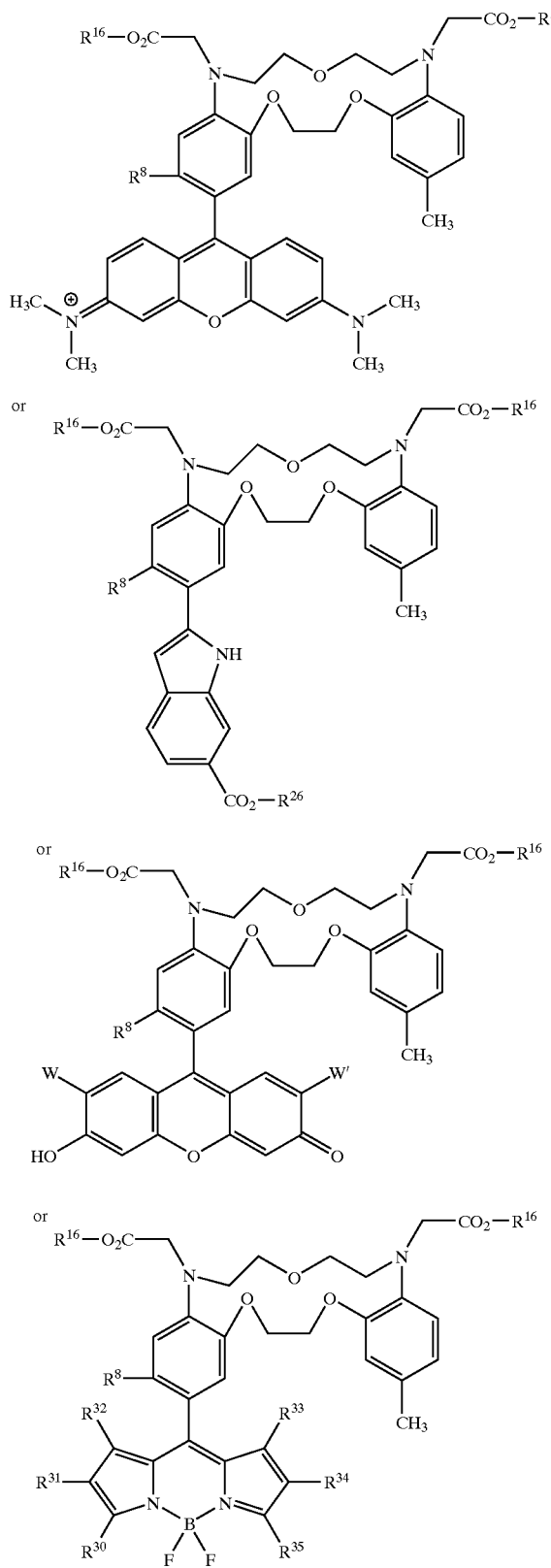

or wherein

R⁸, where present, is independently H or a $C_1$–$C_6$ alkoxy, which is optionally substituted by —(C=O)—O—$R^{16}$ or —(C=O)—$NR^{17}R^{18}$;

$R^{16}$ and $R^{26}$, where present, are independently H, a $C_1$–$C_6$ alkyl, a benzyl, an alpha-acyloxyalkyl, a t-butyldimethylsilyl, or a biologically compatible salt;

$R^{17}$ and $R^{18}$, where present, are independently H, a $C_1$–$C_6$ alkyl, $C_{1-C6}$ carboxyalkyl, or a biologically compatible salt;

W and W', where present, are independently F or Cl;

$R^{30}$–$R^{35}$, where present, are independently H, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons; or an aryl or heteroaryl ring system; or adjacent substituents $R^{31}$ and $R^{32}$, and adjacent substituents $R^{33}$ and $R^{34}$, when taken in combination form a fused benzo ring that is optionally substituted by hydrogen, halogen, nitro, sulfo, cyano, alkyl, perfluoroalkyl, alkoxy, alkenyl, alkynyl, cycloalkyl, alkylthio, alkylamido, amino, monoalkylamino or dialkylamino wherein the alkyl portions of each contain fewer than 20 carbons.

19. A compound having the formula

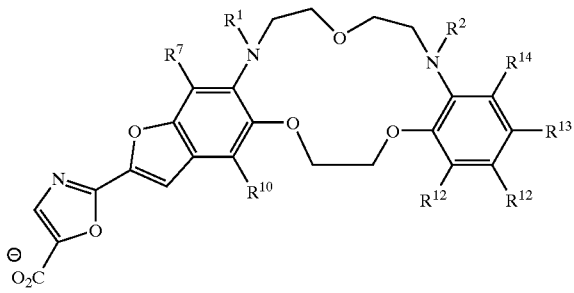

wherein $R^1$ is -L-$R_X$, -L-$S_C$, -L-DYE; $C_1$–$C_{18}$ alkyl or $C_7$–$C_{18}$ arylalkyl, each of which is optionally substituted by halogen, azido, nitro, nitroso, amino, hydroxy, cyano, or by an aryl or heteroaryl ring system; or by —(SO₂)—$R^{15}$, —(SO₂)—O—$R^{15}$, —(C=O)—$R^{15}$, —(C=O)—O—$R^{18}$, —(C=O)—$NR^{17}R^{18}$; or by $C_1$–$C_6$ alkylamino, $C_2$–$C_{12}$ dialkylamino; or by $C_{1-C6}$ alkyl or $C_1$–$C_6$ alkoxy, each of which is itself optionally substituted by halogen, amino, hydroxy, —(SO₂)—$R^{15}$, —(SO₂)—O—$R^{15}$, —(C=O)—$R^{15}$, —(C=O)—O—$R^{16}$, —(C=O)—$NR^{17}R^{18}$;

$R^2$ is -L-$R_X$, -L-$S_C$, -L-DYE; $C_1$–$C_{18}$ alkyl or $C_7$–$C_{16}$ arylalkyl, each of which is optionally substituted by halogen, azido, nitro, nitroso, amino, hydroxy, cyano, or by an aryl or heteroaryl ring system; or by —(SO₂)—$R^{15}$, —(SO₂)—O—$R^{15}$, —(C=O)—$R^{15}$, —(C=O)—O—$R^{16}$, —(C=O)—$NR^{17}R^{18}$; or by $C_1$–$C_6$ alkylamino, $C_2$–$C_{12}$ dialkylamino; or by $C_1$–$C_6$ alkyl or $C_1$–$C_6$ alkoxy, each of which is itself optionally substituted by halogen, amino, hydroxy, —(SO₂)—$R^{15}$, —(SO₂)—O—$R^{15}$, —(C=O)—$R^{15}$, —(C=O)—O—$R^{16}$, —(C=O)—$NR^{17}R^{18}$;

wherein $R^{15}$ is H, $C_1$–$C_6$ alkyl, -L-$R_X$, -L-$S_C$, or -L-DYE;

R[16] is H, a $C_1$–$C_6$ alkyl, a benzyl, alpha-acyloxyalkyl, t-butyldimethylsilyl, a biologically compatible salt, -L-$R_X$, -L-$S_C$, or -L-DYE;

R[17] is H, $C_1$–$C_6$ alkyl, $C_1$–$C_8$ carboxyalkyl, an alpha-acyloxyalkyl, a t-butyldimethylsilyl, a biologically compatible salt, -L-$R_X$, -L-$S_C$, or -L-DYE;

R[18] is H, $C_1$–$C_6$ alkyl, $C_1$–$C_8$ carboxyalkyl, an alpha-acyloxyalkyl, a t-butyldimethylsilyl, a biologically compatible salt, -L-$R_X$, -L-$S_C$, or -L-DYE;

or R[17] and R[18] taken in combination form a 5- or 6-membered aliphatic ring that optionally incorporates an oxygen atom;

L is a covalent linkage;

Rx is selected from the group consisting of an acrylamide, an activated ester of a carboxylic acid, an acyl azide, an acyl nitrile, an aldehyde, an alkyl halide, an anhydride, an aniline, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, or a thiol;

Sc is selected from the group consisting of an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a biotin, a silica and a virus;

DYE is selected from the group consisting of indole, a coumarin, a stilbene, a xanthene, an oxazine, a polyazaindacene, a benzofuran, a pyrene, an anthracene, a naphthalene, an acridine, a benzindole, an oxazole, a benzoxazole, a thiazole, a benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a benzoxazine, a carbazine a phenalenone and a benzphenalenone;

R[7] is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —(SO$_2$)—R[15], —(SO$_2$)—O—R[15], or —(C=O)—R[15], —(C=O)—O—R[16], —(C=O)—NR[17]R[18];

R[10] is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —(SO$_2$)—R[15], —(SO$_2$)—O—R[15], or —(C=O)—R[15], —(C=O)—O—R[16], —(C=O)—NR[17]R[18];

R[11] is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —(SO$_2$)—R[15], —(SO$_2$)—O—R[15], —(C=O)—R[15], or —(C=O)—O—R[16], —(C=O)—NR[17]R[18];

R[12] is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —(SO$_2$)—R[15], —(SO$_2$)—O—R[15], —(C=O)—R[15], —(C=O)—O—R[16], —(C=O)—NR[17]R[18];

R[13] is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —(SO$_2$)—R[15], —(SO$_2$)—O—R[15], —(C=O)—R[15], —(C=O)—O—R[16], —(C=O)—NR[17]R[18];

R[14] is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —(SO$_2$)—R[15], —(SO$_2$)—O—R[15], —(C=O)—R[15], —(C=O)—O—R[16], or —(C=O)—NR[17]R[18].

20. The compound according to claim 19, wherein R[1] and R[2] are $C_1$–$C_8$ alkyl that are substituted one or more times by —(C=O)—O—R[16] or —(C=O)—NR[17]R[18].

21. The compound according to claim 19, wherein R[1] and R[2] are $C_1$–$C_8$ alkyl that are substituted one or more times by —(C=O)—O—R[16], where each R[16] is H, $C_1$–$C_6$ alkyl, an alpha-acyloxymethyl, a t-butyldimethyldimethylsilyl, or a biologically compatible salt.

22. The compound according to claim 19, wherein the compound is

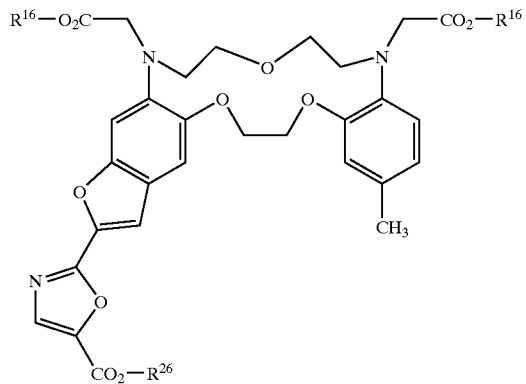

wherein R[16] and R[26], are independently H, a $C_1$–$C_6$ alkyl, a benzyl, an alpha-acytoxyalkyl, a t-butyldimethylsilyl, or a biologically compatible salt.

23. A compound having the formula:

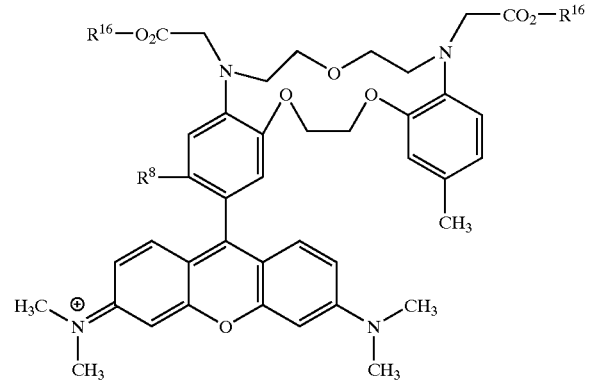

and its salts, wherein

R[8], is H or a $C_1$–$C_6$ alkoxy which is optionally substituted by —(C=O)—O—R[16] or —(C=O)—NR[17]R[18];

R[16] is independently H, a $C_1$–$C_6$ alkyl, a benzyl, an alpha-acyloxyalkyl, a t-butyldimethylsilyl, or a biologically compatible salt; and, R[17] and R[18], where present, are independently H, a $C_1$–$C_6$ alkyl, $C_1$–$C_6$ carboxyalkyl, or a biologically compatible salt.

24. A composition comprising a metal ion and a compound having the formula:

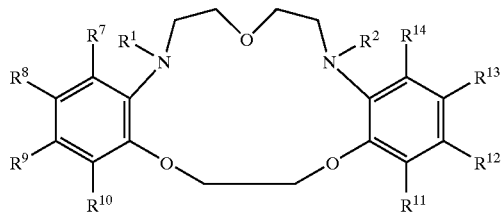

wherein $R^1$ is -L-$R_X$, -L-$S_C$, -L-DYE $C_1$–$C_{18}$ alkyl or $C_7$–$C_{18}$ arylalkyl, each of which is optionally substituted by halogen, azido, nitro, nitroso, amino, hydroxy, cyano, or by an aryl or heteroaryl ring system; or by —($SO_2$)—$R^{15}$, —($SO_2$)—O—$R^{15}$, —(C=O)—$R^{15}$, —(C=O)—O—$R^{16}$, —(C=O)—$NR^{17}R^{18}$; or by $C_1$–$C_6$ alkylamino, $C_2$–$C_{12}$ dialkylamino; or by $C_1$–$C_6$ alkyl or $C_1$–$C_6$ alkoxy, each of which is itself optionally substituted by halogen, amino, hydroxy. —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

$R^2$ is -L-$R_X$, -L-$S_C$, -L-DYE; $C_1$–$C_{18}$ alkyl or $C_1$–$C_{18}$ arylalkyl, each of which is optionally substituted by halogen, azido, nitro, nitroso, amino, hydroxy, cyano, or by an aryl or heteroaryl ring system; or by —($SO_2$)—$R^{15}$, —($SO_2$)—O—$R^{15}$, —(C=O)—$R^{15}$, —(C=O)—O—$R^{16}$, —(C=O)—$NR^{17}R^{18}$; or by $C_1$–$C_6$ alkylamino, $C_2$–$C_{12}$ dialkylamino; or by $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, —(C=O)—$NR^{17}R^{18}$;

wherein $R^{15}$ is H, $C_1$–$C_8$ alkyl, -L-$R_X$, -L-$S_C$, or -L-DYE;

$R^{16}$ is H, a $C_1$–$C_6$ alkyl, a benzyl, alpha-acyloxyalkyl, t-butyldimethylsilyl, a biologically compatible salt, -L-$R_X$, -L-$S_C$, or -L-DYE;

$R^{17}$ is H, $C_1$–$C_6$ alkyl, $C_1$–$C_6$ carboxyalkyl, an alpha-acyloxyalkyl, a t-butyldimethylsilyl, a biologically compatible salt, -L-$R_X$, -L-$S_C$, or -L-DYE;

$R^{18}$ is H, $C_1$–$C_6$ alkyl, $C_1$–$C_6$ carboxyalkyl, an alpha-acyloxyalkyl, a t-butyldimethylsilyl, a biologically compatible salt, -L-$R_X$, -L-$S_C$, or -L-DYE;

or $R^{17}$ and $R^{18}$ taken in combination form a 5- or 6-membered aliphatic ring that optionally incorporates an oxygen atom;

L is a covalent linkage;

Rx is an acrylamide, an activated ester of a carboxylic acid, an acyl azide, an acyl nitrile, an aldehyde, an alkyl halide, an anhydride, an aniline, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, or a thiol;

Sc is an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a biotin, a silica or a virus;

DYE is a chemical moiety with an absorption maximum beyond 320 nm;

$R^7$ is H, halogen, azido, nitro, nitroso, amino, cyano, -L-$R_X$, -L-$S_C$, -L-DYE, $C_1$–$C_8$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^8$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^9$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{10}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

R is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{12}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{13}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{14}$ is H, halogen, azido, nitro, nitroso, amino, cyano, -L-$R_X$, -L-$S_C$, -L-DYE, $C_1$–$C_6$ alkyl or $C_1$–$C_8$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

or any two adjacent substituents $R^7$–$R^{14}$, taken in combination, form a fused six-membered benzo moiety, which is optionally substituted by halogen, azido, nitro, nitroso, amino, cyano, -L-$R_X$, -L-$S_C$, -L-DYE, $C_1$–$C_6$ alkyl or $C_1$–$C_8$ alkoxy, each of which is optionally substituted by halogen, amino, hydroxy, —(C=O)—$R^{15}$, —(C=O)—O—$R^{16}$, or —(C=O)—$NR^{17}R^{18}$;

or any two adjacent substituents $R^7$–$R^{14}$, taken in combination with each other, and with the aromatic ring they are bound to, form a fused DYE;

provided that the compound is substituted by at least one -L-DYE, -L-$R_X$, or -L-$S_C$ at $R^1$, $R^2$, $R^4$, $R^7$, $R^8$, $R^9$, $R^{10}$, $R^{11}$, $R^{12}$, $R^{13}$, or $R^{14}$; or at least two of $R^7$–$R^{14}$, taken in combination, form a fused DYE.

25. The composition according to claim 24, wherein the metal ion is $Na^+$, $K^+$, $Ca^{2+}$, or $Zn^{2+}$.

26. The composition according to claim 24, wherein DYE is an indole, a coumarin, a stilbene, a xanthene, an oxazine, a polyazaindacene, a benzofuran, a pyrene, an anthracene, a naphthalene, an acridine, a benzindole, an oxazole, a benzoxazole, a thiazole, a benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a benzoxazine, a carbazine a phenalenone or a benzphenalenone.

27. A method of detecting a target cationic metal ion in a sample, comprising:
a) adding to the sample, in an amount sufficient to generate a detectable optical response when the target ion is present, a compound having the formula:

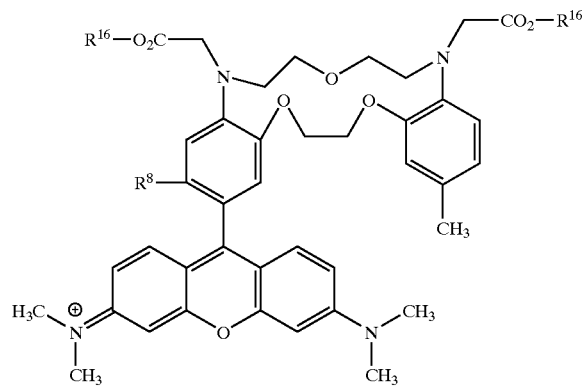

and its salts, wherein
$R^8$, is H or a $C_1$–$C_6$ alkoxy, which is optionally substituted by —(C=O)—O—$R^{16}$ or —(C=O)—$NR^{17}R^{18}$;
$R^{16}$ is independently H, a $C_1$–$C_6$ alkyl, a benzyl, an alpha-acyloxyalkyl, a t-butyldimethylsilyl, or a biologically compatible salt; and,
$R^{17}$ and $R^{18}$, where present, are independently H, a $C_1$–$C_6$ alkyl, $C_1$–$C_6$ carboxyalkyl, or a biologically compatible salt;
b) illuminating the sample to generate the detectable optical response whereby said target ion is detected.

28. The composition according to claim 25, wherein said compound is substituted by only one -L-$R_X$, or -L-$S_C$, that is bound at $R^8$, $R^9$, $R^{12}$, or $R^{13}$.

29. The composition according to claim 25, wherein $R^1$ and $R^2$ are $C_1$–$C_6$ alkyl that are substituted one or more times by cyano, —(C=O)—O—$R^{16}$, or —(C=O)—$NR^{17}R^{18}$.

30. The composition according to claim 25, wherein $R^8$ and $R^9$, and optionally $R^{12}$ and $R^{13}$, taken in combination, form a fused DYE that is a substituted or unsubstituted benzofuran.

31. The composition according to claim 25, wherein said compound is substituted by exactly two DYE or fused DYE moieties.

32. The composition according to claim 25, wherein said compound is substituted by exactly one -L-DYE moiety at $R^9$, and said compound is optionally substituted by exactly one -L-$R_X$ or exactly one -L-$S_C$ at a position other than $R^9$.

33. The composition according to claim 25, wherein each L of the compound is independently a single covalent bond, or a covalent linkage that is linear or branched, cyclic or heterocyclic, saturated or unsaturated, having 1–20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

34. The composition according to claim 25, wherein each L of the compound is a single covalent bond or has the formula —$(CH_2)_d(CONH(CH_2)_e)_z$— or —$O(CH_2)_d(CONH(CH_2)_e)_z$—, where d is an integer from 0–5, e is an integer from 1–5 and z is 0 or 1.

35. The composition according to claim 25, wherein said compound is substituted by exactly one $S_C$ that is a protein, a polysaccharide, a biotin, or a silica.

36. The composition according to claim 25, wherein said compound is substituted by exactly one $R_X$ selected from the group consisting of a succinimidyl ester of a carboxylic acid, a haloacetamide, a hydrazine, an isothiocyanate, a maleimide, an aliphatic amine, a silyl halide, and a psoralen.

37. The composition according to claim 25, where the compound has the formula:

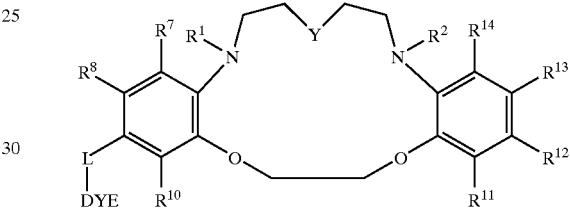

wherein Y is O.

38. The composition according to claim 37, wherein each DYE on the compound is a fluorescein, a rhodamine, a rhodol, a polyazaindacene, an oxazine, a 3H-xanthen-6-ol-3-one, a 6-amino-3H-xanthen-3-one, or a 6-amino-3H-xanthen-3-imine.

39. The composition according to claim 38, wherein $R^1$ and $R^2$ are $C_1$–$C_6$ alkyl that are substituted one or more times by —(C=O)—O—$R^{16}$ or —(C=O)—$NR^{17}R^{18}$.

40. The composition according to claim 39, wherein $R^1$ and $R^2$ are $C_1$–$C_6$ alkyl that are substituted one or more times by —(C=O)—O—$R^{16}$, where each $R^{16}$ is H, an alpha-acyloxymethyl, a t-butyldimethyldimethylsilyl, or a biologically compatible salt.

41. The composition according to claim 37, wherein the metal ion that is $Ca^{2+}$, $Na^+$, $K^+$, or $Zn^{2+}$.

42. A method of detecting a target cationic metal ion in a sample, comprising:
a) adding to said sample, in an amount sufficient to generate a detectable optical response when said target ion is present, a compound having the formula:

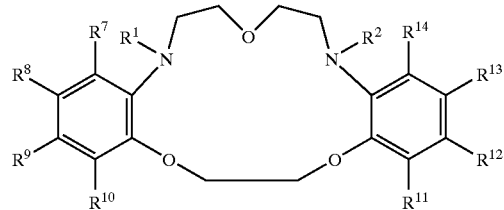

wherein $R^1$ is -L-$R_X$, -L-$S_C$, -L-DYE; $C_1$–$C_{18}$ alkyl or $C_1$–$C_{18}$ arylalkyl, each of which is optionally substituted by halogen, azido, nitro, nitroso, amino, hydroxy, cyano, or by an aryl or heteroaryl ring system; or by —$(SO_2)$—$R^{15}$, —$(SO_2)$—O—$R^{16}$, —$(C=O)$—$R^{15}$, —$(C=O)$—O—$R^{16}$, —$(C=O)$—$NR^{17}R^{18}$; or by $C_1$–$C_6$ alkylamino, $C_2$–$C_{12}$ dialkylamino; or by $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{16}$, —$(C=O)$—$R^{15}$, —$(C=O)$—O—$R^{16}$, —$(C=O)$—$NR^{17}R^{18}$;

$R^2$ is -L-$R_X$, -L-$S_C$, -L-DYE; $C_1$–$C_{18}$ alkyl or $C_7$–$C_{18}$ arylalkyl, each of which is optionally substituted by halogen, azido, nitro, nitroso, amino, hydroxy, cyano, or by an aryl or heteroaryl ring system; or by —$(SO_2)$—$R^{15}$, —$(SO_2)$—O—$R^{15}$, —$(C=O)$—$R^{15}$, —$(C=O)$—O—$R^{16}$, —$(C=O)$—$NR^{17}R^{18}$; or by $C_1$–$C_6$ alkylamino, $C_2$–$C_{12}$ dialkylamino; or by $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, —$(C=O)$—$NR^{17}R^{18}$;

wherein $R^{15}$ is H, $C_1$–$C_6$ alkyl, -L-$R_X$, -L-$S_C$, or -L-DYE;

$R^{16}$ is H, a $C_1$–$C_6$ alkyl, a benzyl, alpha-acyloxyalkyl, t-butyldimethylsilyl, a biologically compatible salt, -L-$R_X$, -L-$S_C$, or -L-DYE;

$R^{17}$ is H, $C_1$–$C_6$ alkyl, $C_1$–$C_8$ carboxyalkyl, an alpha-acyloxyalkyl, a t-butyldimethylsilyl, a biologically compatible salt, -L-$R_X$, -L-$S_C$, or -L-DYE;

$R^{18}$ is H, $C_1$–$C_6$ alkyl, $C_1$–$C_8$ carboxyalkyl, an alpha-acyloxyalkyl, a t-butyldimethylsilyl, a biologically compatible salt, -L-$R_X$, -L-$S_C$, or -L-DYE;

or $R^{17}$ and $R^{18}$ taken in combination form a 5- or 6-membered aliphatic ring that optionally incorporates an oxygen atom;

L is a covalent linkage;

Rx is an acrylamide, an activated ester of a carboxylic acid, an acyl azide, an acyl nitrile, an aldehyde, an alkyl halide, an anhydride, an aniline, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, or a thiol;

Sc is an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a biotin, a silica or a virus;

DYE is a chemical moiety with an absorption maximum beyond 320 nm;

$R^7$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, —$(C=O)$—$NR^{17}R^{18}$;

$R^8$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, or —$(C=O)$—$NR^{17}R^{18}$;

$R^9$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, or —$(C=O)$—$NR^{17}R^{18}$;

$R^{10}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, or —$(C=O)$—$NR^{17}R^{18}$;

$R^{11}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, or —$(C=O)$—$NR^{17}R^{18}$;

$R^{12}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, or —$(C=O)$—$NR^{17}R^{18}$;

$R^{13}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, or —$(C=O)$—$NR^{17}R^{18}$;

$R^{14}$ is H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —$(SO_2)$—$R^{15}$, —$(SO_2)$—O—$R^{15}$, —$(C=O)$—$R^{15}$, —$(C=O)$—O—$R^{16}$, or —$(C=O)$—$NR^{17}R^{18}$;

or any two adjacent substituents $R^7$–$R^{14}$, taken in combination, form a fused six-membered benzo moiety, which is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is optionally substituted by halogen, amino, hydroxy, —$(C=O)$—$R^{15}$, —$(C=O)$—O—$R^{16}$, or —$(C=O)$—$NR^{17}R^{18}$;

or any two adjacent substituents $R^7$–$R^{14}$, taken in combination with each other, and with the aromatic ring they are bound to, form a fused DYE;

provided that the compound is substituted by at least one -L-DYE, -L-$R_X$, or -L-$S_C$ at $R^1$, $R^2$, $R^4$, $R^7$, $R^8$, $R^9$, $R^{10}$, $R^{11}$, $R^{12}$, $R^{13}$, or $R^{14}$; or at least two of $R^7$–$R^{14}$, taken in combination, form a fused DYE;

b) illuminating said sample to generate said detectable optical response whereby said target ion is present.

43. A method, as claimed in claim 42, wherein said detectable optical response is a fluorescence response.

44. A method, as claimed in claim 43, wherein said illuminating is performed in conjunction with a fluorometer, fluorescence microscope, laser scanner, flow cytometer, a microfluidic device, or a fiber optic probe.

45. A method, as claimed in claim 42, wherein said target metal ion is $Na^+$, $K^+$, $Ca^{2+}$, or $Zn^{2+}$.

46. A method, as claimed in claim 42, wherein said compound has the formula:

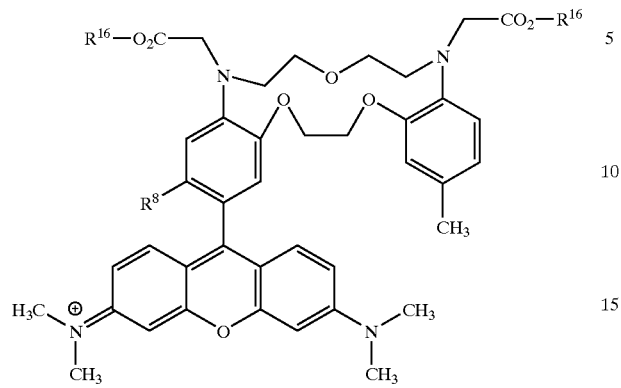

or the formula:

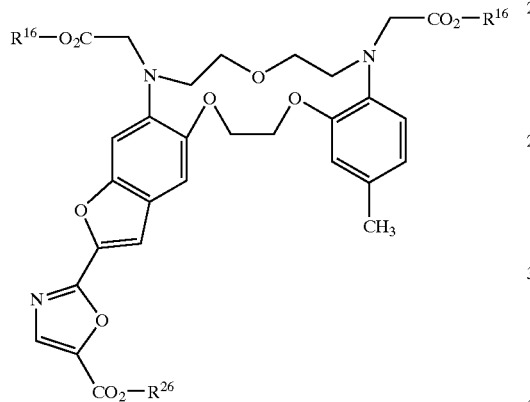

or the formula:

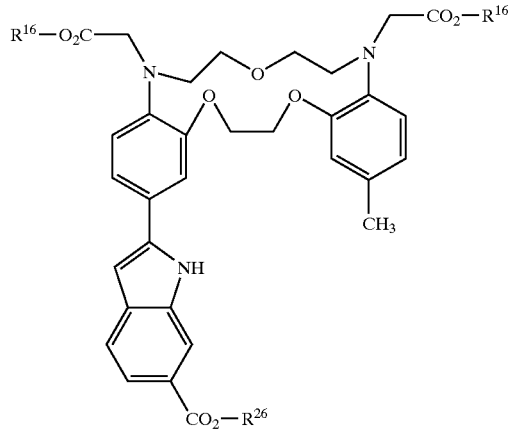

or the formula:

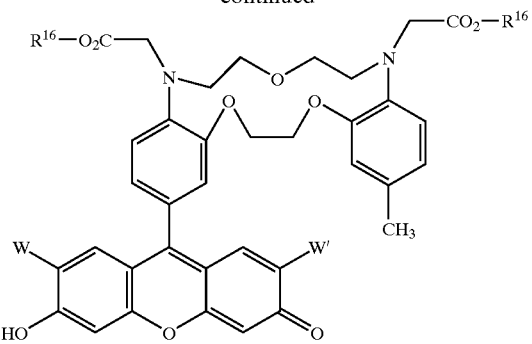

or the formula:

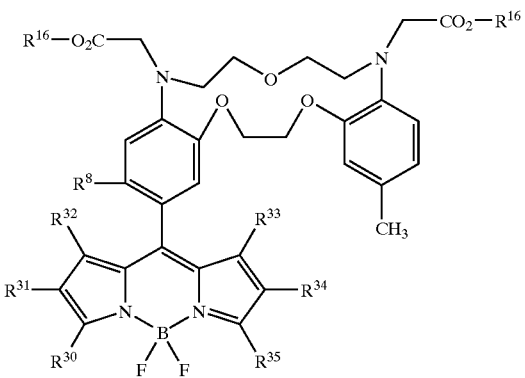

wherein $R^8$, where present, is independently H or a $C_1$–$C_6$ alkyoxy, which is optionally substituted by —(C=O)—O—$R^{16}$ or —(C=O)—$NR^{17}R^{18}$;

$R^{16}$ and $R^{26}$, where present, are independently H, a $C_1$–$C_6$ alkyl, a benzyl, an alpha-acyloxyalkyl, a t-butyldimethylsilyl, or a biologically compatible salt;

$R^{17}$ and $R^{18}$, where present, are independently H, a $C_1$–$C_6$ alkyl, $C_1$–$C_6$ carboxyalkyl, or a biologically compatible salt;

W and W', where present, are independently F or Cl;

$R^{30}$–$R^{35}$, where present, are independently H, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons; or an aryl or heteroaryl ring system.

47. A method, as claimed in claim 46, wherein said target metal ion is $Na^+$ or $K^+$.

48. A method, as claimed in claim 42, wherein said sample comprises living cells or biological fluids.

\* \* \* \* \*